US010906957B2

(12) United States Patent
Larson et al.

(10) Patent No.: US 10,906,957 B2
(45) Date of Patent: Feb. 2, 2021

(54) IMMUNOMODULATORY FUSION PROTEINS

(71) Applicant: EpicentRx, Inc., San Diego, CA (US)

(72) Inventors: Christopher Larson, San Diego, CA (US); Tony R. Reid, San Diego, CA (US); Bryan T. Oronsky, Los Altos Hills, CA (US)

(73) Assignee: EpicentRx, Inc., San Diego, CA (US)

( * ) Notice: Subject to any disclaimer, the term of this patent is extended or adjusted under 35 U.S.C. 154(b) by 0 days.

(21) Appl. No.: 15/717,199

(22) Filed: Sep. 27, 2017

(65) Prior Publication Data
US 2018/0134766 A1 May 17, 2018

Related U.S. Application Data

(60) Provisional application No. 62/484,841, filed on Apr. 12, 2017, provisional application No. 62/400,338, filed on Sep. 27, 2016.

(51) Int. Cl.
| | |
|---|---|
| *C07K 14/71* | (2006.01) |
| *C12N 7/00* | (2006.01) |
| *A61P 35/00* | (2006.01) |
| *C07K 16/00* | (2006.01) |
| *C12N 15/86* | (2006.01) |
| *A61K 48/00* | (2006.01) |
| *A61K 35/768* | (2015.01) |
| *A61K 38/00* | (2006.01) |

(52) U.S. Cl.
CPC ............ *C07K 14/71* (2013.01); *A61P 35/00* (2018.01); *C07K 16/00* (2013.01); *C12N 7/00* (2013.01); *C12N 15/86* (2013.01); *A61K 35/768* (2013.01); *A61K 38/00* (2013.01); *A61K 48/00* (2013.01); *C07K 2317/522* (2013.01); *C07K 2317/524* (2013.01); *C07K 2317/53* (2013.01); *C07K 2317/76* (2013.01); *C07K 2319/01* (2013.01); *C07K 2319/30* (2013.01); *C12N 2710/10332* (2013.01); *C12N 2710/10333* (2013.01); *C12N 2710/10343* (2013.01); *C12N 2710/10371* (2013.01)

(58) Field of Classification Search
CPC ............ C07K 14/715; C07K 2317/76; C07K 2317/53; C07K 2317/524; C07K 2317/522; C07K 2319/30; C12N 15/86; C12N 2710/10332; C12N 2710/10343; A61K 35/768; A61K 48/00; A61P 35/00
See application file for complete search history.

(56) References Cited

U.S. PATENT DOCUMENTS

| | | | |
|---|---|---|---|
| 4,816,567 A | 3/1989 | Cabilly et al. | |
| 4,946,778 A | 8/1990 | Ladner et al. | |
| 4,980,286 A | 12/1990 | Morgan et al. | |
| 5,482,858 A | 1/1996 | Huston et al. | |
| 5,525,491 A | 6/1996 | Huston et al. | |
| 6,472,179 B2 | 10/2002 | Stahl et al. | |
| 7,083,950 B2 | 8/2006 | Stahl et al. | |
| 9,073,980 B2 | 7/2015 | Reid et al. | |
| 2002/0004037 A1* | 1/2002 | Koteliansky | C07K 14/71 424/85.1 |
| 2003/0125251 A1 | 7/2003 | Wakefield et al. | |
| 2005/0042220 A1 | 2/2005 | Li et al. | |
| 2007/0184052 A1 | 8/2007 | Lin et al. | |
| 2009/0111146 A1 | 4/2009 | Ohtsuka et al. | |
| 2009/0175819 A1 | 7/2009 | Priest et al. | |
| 2015/0225483 A1 | 8/2015 | Lo | |
| 2020/0223901 A1 | 7/2020 | Larson et al. | |

FOREIGN PATENT DOCUMENTS

| | | |
|---|---|---|
| EP | 2326670 A1 | 6/2011 |
| WO | WO-1993/010151 A1 | 5/1993 |
| WO | WO-1996/011213 A1 | 4/1996 |
| WO | WO-1997/006826 A1 | 2/1997 |
| WO | WO-1998/027216 A1 | 6/1998 |
| WO | WO-1998/040498 A2 | 9/1998 |
| WO | WO-1998/048024 A1 | 10/1998 |
| WO | WO-2001/003737 A1 | 1/2001 |
| WO | WO-2001/010912 A1 | 2/2001 |
| WO | WO-2003066002 A2 | 8/2003 |
| WO | WO-2005/005638 | 1/2005 |
| WO | WO-2006084327 A1 | 8/2006 |
| WO | WO-2008/024188 A2 | 2/2008 |
| WO | WO-2008/157367 A1 | 12/2008 |

(Continued)

OTHER PUBLICATIONS

Chung et al. (2002) "Catheter-based adenovirus-mediated local intravascular gene delivery of a soluble TGF-β type II receptor using an Infiltrator in porcine coronary arteries: efficacy and complications," Exp. Molecular Med., 34(4):299-307.

Connolly et al. (2012) "Complexities of TGF-β targeted cancer therapy," Int. J. Biol. Sci., 8(7):964-78.

George et al. (2003) "An analysis of protein domain linkers: their classification and role in protein folding," Protein Engineering, 15:871-879.

Hu et al. (2010) "A modified hTERT Promoter-directed Oncolytic Adenovirus Replication with Concurrent Inhibition of TGFβ Signaling for Breast Cancer Therapy," Cancer Gene Ther., 17(4):235-43.

(Continued)

*Primary Examiner* — Ruixiang Li
(74) *Attorney, Agent, or Firm* — Morrison & Foerster LLP

(57) ABSTRACT

Provided is a fusion protein, e.g., a cytokine receptor fusion protein, e.g., a TGFβ trap, with a novel linker sequence to permit the fusion protein to functionally optimally, e.g., to permit a cytokine receptor portion of a cytokine receptor fusion protein to bind optimally to its target cytokine. The fusion proteins, or expression vectors encoding for the fusion proteins, e.g., oncolytic adenoviral expression vectors, can be used to treat cell proliferative diseases and disorders, including certain forms of cancer and inflammatory disorders.

8 Claims, 7 Drawing Sheets

Specification includes a Sequence Listing.

(56) References Cited

FOREIGN PATENT DOCUMENTS

| WO | WO-2009154995 A2 | 12/2009 | |
|---|---|---|---|
| WO | WO-2010/031168 A1 | 3/2010 | |
| WO | WO-2015027082 A1 | 2/2015 | |
| WO | WO-2015/077540 A2 | 5/2015 | |
| WO | WO-2016/100788 A1 | 6/2016 | |
| WO | WO-2016174575 A1 | 11/2016 | |
| WO | WO-2017037634 A1 * | 3/2017 | ............. C07K 14/71 |
| WO | WO-2018126282 A1 | 7/2018 | |

OTHER PUBLICATIONS

Hu et al. (2010) "Systemic delivery of an oncolytic adenovirus expressing soluble transforming growth factor-β receptor II-Fc fusion protein can inhibit breast cancer bone metastasis in a mouse model," Hum. Gene Ther., 21(11):1623-9.

International Search Report for PCT/US2017/053765, dated Feb. 21, 2018 (12 pages).

Isaka et al. (1999) "Gene therapy by transforming growth factor-β receptor-IgG Fc chimera suppressed extracellular matrix accumulation in experimental glomerulonephritis," Kidney Int., 55(2):465-75.

Linderholm et al. (2014) "Immunoglobulin Fc-Fusion Proteins Part 1: Their Design and Manufacture," BioProcess International, 12(9):30-35.

Tatsis et al. (2004) "Adenoviruses as vaccine vectors," Mol Ther., 10(4):616-29.

Taylor (2009) "Review of the activation of TGF-beta in immunity," J. Leukoc. Biol., 85(1):29-33.

Written Opinion for PCT/US2017/053765, dated Feb. 21, 2018 (8 pages).

Zhang et al. (2015) "A novel immunocompetent murine model for replicating oncolytic adenoviral therapy," Cancer Gene Ther., 22(1):17-22.

Howard et al. (1989) *J. Neurosurg.*, 71:105-112.

Joliot et al. (1991) *Proc. Natl. Acad. Sci. USA*, 88: 1864-1868.

Wu et al. (1987) *J. Biol. Chem.*, 262: 4429-4432.

Fiorentino et al., (1989). "Two types of mouse T helper cell. IV. Th2 clones secrete a factor that inhibits cytokine production by Th1 clones," J. Exp. Med., 170(6):2081-2095.

George et al., (2003). "An analysis of protein domain linkers: their classification and role in protein folding," Protein Engineering, Design and Selection, 15:871-879.

Henikoff et al., (1992). "Amino acid substitution matrices from protein blocks," PNAS USA, 89:10915-10919.

International Search Report for PCT/US2018/053197 dated Jan. 7, 2019, 10 pages.

Karlin et al., (1990). "Methods for assessing the statistical significance of molecular sequence features by using general scoring schemes," PNAS, 87:2264-2268.

Written Opinion for PCT/US2018/053197 dated Jan. 7, 2019, 9 pages.

* cited by examiner

```
Human CH1 domains

IgA1   PKVFPLS.....LCSTQPDGNV-.....VIACLVQGf.....fPQEPLSVTWSESGQgv.....taRNFPPSQDASGDL.....YTTSSQLELPA.....TCCLAGKSVTCHVNH.......YTNPSQDVT
IgA2   PKVPPLS.....LDSTPQDGNV-.....VVACLVQGf.....fPQEPLSVTWSESGQnv.....taRNFPPSQDASGDL.....YTTSSQLELPA.....TQCPDGKSVTCHVKH.......YTNPSQDVT
IgD    PTVFPIIs....GCRHPKDNSPV.....VLACLIIGY.....HPTSVTVTWMGTQSq.....pQRTTPEIQRRDSY.....YMTSSQLSTP-.....LQQWRQGEYKCVVQH......TASKKKEIF
IgE    PSVFPLTr....cCKNIPSNATSV....TLGCLATGy.....FPEPVMVTWDTGSLn.......GTTMTLPATTLTLsg..hYATISLLFVSG......AWAKQMFTCRVAHt....pSSTDWVDNKTFS
IgG1   PSVFPLA.....PSSKSTSGGTA....ALGCLVKDy.....FPEPVTVSWNSGALts.....gVHTFPAVLQSSGL.....YSLSSVVTVPS......SSLGTQTYICNVNH......KPSNTKVDKKVE
IgG2   PSVFPLA.....PCSRSTSESTA....ALGCLVKDy.....FPEPVTVSWNSGALts.....gVHTFPAVLQSSGL.....YSLSSVVTVPS......SNFGTQTYTCNVDH......KPSNTKVDKTVE
IgG3   PSVFPLA.....PCSRSTSGGTA....ALGCLVKDy.....FPEPVTVSWNSGALts.....gVHTFPAVLQSSGL.....YSLSSVVTVPS......SSLGTQTYTCNVNH......KPSNTKVDKRVE
IgG4   PSVFPLA.....PCSRSTSESTA....ALGCLVKDy.....FPEPVTVSWNSGALts.....gVHTFPAVLQSSGL.....YSLSSVVTVPS......SSLGTKYTCNVDH......KPSNTKVDKRVE
IgM    PTLFPLVs....CENSPSDTSSV....AVGCLAQDf.....LPDSITLSWKYKNN.......SDISSTRGFPSVLrg..gkYAATSQVLLPSk..dVMQGTDEHVCKVQH......PNGNKEKNVP

Human CH2 domains

IgA1   PRLSLHRp....ALEDLLLGSEA.....NLTCTLTGl.....rDASGVTFTWTPSSG.......KSAVQGPPERDLCg.....CYSVSSVLPGCA.....EPWNHGKTFTCTAAY.....PESKTPLTATLS
IgA2   PRLSLHRp....ALEDLLLGSEA.....NLTCTLTGl.....rDASGATTWTPSSG........KSAVQGPPERDLCg.....CYSVSSVLPGCA.....QPWNHGETFTCTAAH......PELKTPLTANTT
IgD    PAVQDL-.....---WLRDKA--.....TFTCFVVGs.....DLKDAHLTWEVAGKVpt.....ggVEEGLLERHSNGS-......QSQHSRITLPR.....SLWNAGTSVTCTLNH......PSLPPQRLMA
IgE    PTVKIL-.....-QSSCDGGGHFpp..HiQLLCLVSGy....TPGTINITWLEDGQvm......dvDLSTASTTQEGEL.....ASTQSELTLSQ......KHWLSDRTYTCQVTYq....GHTFEDSTKKCA
IgG1   PSVFLFPp....KPKDTLMISRTP....EVTCVVVDvs....hEDPEVKFNWYVDGVe......hnAKTKPREEQYNST.....YRVVSVLTVLH.......QDWLNGKEYKCKVSN......KALPAPIEKTIS
IgG2   PSVFLFPp....kPKDTLMISRTP....EVTCVVVDvs....hEDPEVQFNWYVDGVe......VHNAKTKPREEQFns..tFRVVSVLTVVH.......QDWLNGKEYKCKVSN......KGLPAPIEKTIS
IgG3   PSVFLFPp....kPKDTLMISRTP....EVTCVVVDvs....hEDPEVQFKWYVDGVe......hnAKTKPREEQYNST.....FRVVSVLTVLH.......QDWLNGKEYKCKVSN......KALPAPIEKTIS
IgG4   PSVFLFPp....KPKDTLMISRTP....EVTCVVVDvs....qEDPEVQFNWYVDGVe......VHNAKTKPREEQFns..tKRVVSVLTVLH.......QDWLNGKEYKCKVSN......KGLPSSIEKTIS
IgM    PKVSVFV.....PPRDGFFGNPRk...SKLICQATGf....SPRQIQVSWLREGKQvysg..vttdQVQAEAKESGPTT......YKVTSTLTIKE.....SDWLSGSMFTCRVDH.......RGLTFQQNAS
```

FIGURE 2

SEQUENCE LISTING

<160> NUMBER OF SEQ ID NOS: 63

<210> SEQ ID NO 1
<211> LENGTH: 12
<212> TYPE: PRT
<213> ORGANISM: Homo sapiens

<400> SEQUENCE: 1

Lys Pro Ser Asn Thr Lys Val Asp Lys Lys Val Glu
1               5                   10

<210> SEQ ID NO 2
<211> LENGTH: 12
<212> TYPE: PRT
<213> ORGANISM: Homo sapiens

<400> SEQUENCE: 2

Lys Pro Ser Asn Thr Lys Val Asp Lys Thr Val Glu
1               5                   10

<210> SEQ ID NO 3
<211> LENGTH: 12
<212> TYPE: PRT
<213> ORGANISM: Homo sapiens

<400> SEQUENCE: 3

Lys Pro Ser Asn Thr Lys Val Asp Lys Arg Val Glu
1               5                   10

<210> SEQ ID NO 4
<211> LENGTH: 12
<212> TYPE: PRT
<213> ORGANISM: Homo sapiens

<400> SEQUENCE: 4

Lys Pro Ser Asn Thr Lys Val Asp Lys Arg Val Glu
1               5                   10

<210> SEQ ID NO 5
<211> LENGTH: 12
<212> TYPE: PRT
<213> ORGANISM: Homo sapiens

<400> SEQUENCE: 5

Val Lys His Tyr Thr Asn Pro Ser Gln Asp Val Thr
1               5                   10

<210> SEQ ID NO 6
<211> LENGTH: 12
<212> TYPE: PRT
<213> ORGANISM: Homo sapiens

<400> SEQUENCE: 6

Val Lys His Tyr Thr Asn Pro Ser Gln Asp Val Thr
1               5                   10

<210> SEQ ID NO 7
<211> LENGTH: 10
<212> TYPE: PRT
<213> ORGANISM: Homo sapiens

<400> SEQUENCE: 7

Thr Ala Ser Lys Ser Lys Lys Glu Ile Phe
1               5                   10

<210> SEQ ID NO 8
<211> LENGTH: 14
<212> TYPE: PRT
<213> ORGANISM: Homo sapiens

<400> SEQUENCE: 8

Thr Pro Ser Ser Thr Asp Trp Val Asp Asn Lys Thr Phe Ser
1               5                   10

<210> SEQ ID NO 9
<211> LENGTH: 13
<212> TYPE: PRT
<213> ORGANISM: Homo sapiens

<400> SEQUENCE: 9

Val Gln His Pro Asn Gly Asn Lys Glu Lys Asn Val Pro
1               5                   10

<210> SEQ ID NO 10
<211> LENGTH: 13
<212> TYPE: PRT
<213> ORGANISM: Homo sapiens

<400> SEQUENCE: 10

Val Gln His Pro Asn Gly Asn Lys Glu Lys Asn Val Pro
1               5                   10

<210> SEQ ID NO 11
<211> LENGTH: 12
<212> TYPE: PRT
<213> ORGANISM: Homo sapiens

<400> SEQUENCE: 11

Arg Glu Lys Gln Thr Asp Glu Ile Lys Asp Thr Arg
1               5                   10

<210> SEQ ID NO 12
<211> LENGTH: 159
<212> TYPE: PRT
<213> ORGANISM: Homo sapiens

<400> SEQUENCE: 12

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

-continued

```
Asp Asn Ile Ile Phe Ser Glu Glu Tyr Asn Thr Ser Asn Pro Asp
145                 150                 155
```

<210> SEQ ID NO 13
<211> LENGTH: 231
<212> TYPE: PRT
<213> ORGANISM: Homo sapiens

<400> SEQUENCE: 13

```
Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

<210> SEQ ID NO 14
<211> LENGTH: 227
<212> TYPE: PRT
<213> ORGANISM: Homo sapiens

<400> SEQUENCE: 14

```
Arg Lys Cys Cys Val Glu Cys Pro Pro Cys Pro Ala Pro Pro Val Ala
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Gln Phe Asn Trp Tyr Val Asp Gly Val Glu Val
    50                  55                  60

His Asn Ala Lys Thr Lys Pro Arg Glu Glu Gln Phe Asn Ser Thr Phe
65                  70                  75                  80
```

```
Arg Val Val Ser Val Leu Thr Val Val His Gln Asp Trp Leu Asn Gly
                85                  90                  95

Lys Glu Tyr Lys Cys Lys Val Ser Asn Lys Gly Leu Pro Ala Pro Ile
            100                 105                 110

Glu Lys Thr Ile Ser Lys Thr Lys Gly Gln Pro Arg Glu Pro Gln Val
            115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ser Val Glu
145                 150                 155                 160

Trp Glu Ser Asn Gly Gln Pro Glu Asn Asn Tyr Lys Thr Thr Pro Pro
                165                 170                 175

Met Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 15
<211> LENGTH: 278
<212> TYPE: PRT
<213> ORGANISM: Homo sapiens

<400> SEQUENCE: 15

Leu Lys Thr Pro Leu Gly Asp Thr Thr His Thr Cys Pro Arg Cys Pro
1               5                   10                  15

Glu Pro Lys Ser Cys Asp Thr Pro Pro Cys Pro Arg Cys Pro Glu
            20                  25                  30

Pro Lys Ser Cys Asp Thr Pro Pro Cys Pro Arg Cys Pro Glu Pro
            35                  40                  45

Lys Ser Cys Asp Thr Pro Pro Cys Pro Arg Cys Pro Ala Pro Glu
50                  55                  60

Leu Leu Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser His Glu Asp Pro Glu Val Gln Phe Lys Trp Tyr Val Asp Gly
            100                 105                 110

Val Glu Val His Asn Ala Lys Thr Lys Pro Arg Glu Glu Gln Tyr Asn
            115                 120                 125

Ser Thr Phe Arg Val Val Ser Val Leu Thr Val Leu His Gln Asp Trp
    130                 135                 140

Leu Asn Gly Lys Glu Tyr Lys Cys Lys Val Ser Asn Lys Ala Leu Pro
145                 150                 155                 160

Ala Pro Ile Glu Lys Thr Ile Ser Lys Thr Lys Gly Gln Pro Arg Glu
                165                 170                 175

Pro Gln Val Tyr Thr Leu Pro Pro Ser Arg Glu Glu Met Thr Lys Asn
            180                 185                 190

Gln Val Ser Leu Thr Cys Leu Val Lys Gly Phe Tyr Pro Ser Asp Ile
            195                 200                 205

Ala Val Glu Trp Glu Ser Ser Gly Gln Pro Glu Asn Asn Tyr Asn Thr
    210                 215                 220
```

```
Thr Pro Pro Met Leu Asp Ser Asp Gly Ser Phe Phe Leu Tyr Ser Lys
225                 230                 235                 240

Leu Thr Val Asp Lys Ser Arg Trp Gln Gln Gly Asn Ile Phe Ser Cys
            245                 250                 255

Ser Val Met His Glu Ala Leu His Asn Arg Phe Thr Gln Lys Ser Leu
        260                 265                 270

Ser Leu Ser Pro Gly Lys
        275

<210> SEQ ID NO 16
<211> LENGTH: 228
<212> TYPE: PRT
<213> ORGANISM: Homo sapiens

<400> SEQUENCE: 16

Ser Lys Tyr Gly Pro Pro Cys Pro Ser Cys Pro Ala Pro Glu Phe Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225

<210> SEQ ID NO 17
<211> LENGTH: 255
<212> TYPE: PRT
<213> ORGANISM: Homo sapiens

<400> SEQUENCE: 17

Val Pro Cys Pro Val Pro Ser Thr Pro Pro Thr Pro Ser Pro Ser Thr
1               5                   10                  15

Pro Pro Thr Pro Ser Pro Ser Cys Cys His Pro Arg Leu Ser Leu His
            20                  25                  30
```

```
Arg Pro Ala Leu Glu Asp Leu Leu Gly Ser Glu Ala Asn Leu Thr
    35                  40                  45

Cys Thr Leu Thr Gly Leu Arg Asp Ala Ser Gly Val Thr Phe Thr Trp
50                  55                  60

Thr Pro Ser Ser Gly Lys Ser Ala Val Gln Gly Pro Pro Glu Arg Asp
65                  70                  75                  80

Leu Cys Gly Cys Tyr Ser Val Ser Ser Val Leu Pro Gly Cys Ala Glu
                85                  90                  95

Pro Trp Asn His Gly Lys Thr Phe Thr Cys Thr Ala Ala Tyr Pro Glu
            100                 105                 110

Ser Lys Thr Pro Leu Thr Ala Thr Leu Ser Lys Ser Gly Asn Thr Phe
        115                 120                 125

Arg Pro Glu Val His Leu Leu Pro Pro Ser Glu Glu Leu Ala Leu
    130                 135                 140

Asn Glu Leu Val Thr Leu Thr Cys Leu Ala Arg Gly Phe Ser Pro Lys
145                 150                 155                 160

Asp Val Leu Val Arg Trp Leu Gln Gly Ser Gln Glu Leu Pro Arg Glu
                165                 170                 175

Lys Tyr Leu Thr Trp Ala Ser Arg Gln Glu Pro Ser Gln Gly Thr Thr
            180                 185                 190

Thr Phe Ala Val Thr Ser Ile Leu Arg Val Ala Ala Glu Asp Trp Lys
        195                 200                 205

Lys Gly Asp Thr Phe Ser Cys Met Val Gly His Glu Ala Leu Pro Leu
210                 215                 220

Ala Phe Thr Gln Lys Thr Ile Asp Arg Leu Ala Gly Lys Pro Thr His
225                 230                 235                 240

Val Asn Val Ser Val Val Met Ala Glu Val Asp Gly Thr Cys Tyr
                245                 250                 255

<210> SEQ ID NO 18
<211> LENGTH: 242
<212> TYPE: PRT
<213> ORGANISM: Homo sapiens

<400> SEQUENCE: 18

Val Pro Cys Pro Val Pro Pro Pro Pro Cys Cys His Pro Arg Leu
1               5                   10                  15

Ser Leu His Arg Pro Ala Leu Glu Asp Leu Leu Gly Ser Glu Ala
            20                  25                  30

Asn Leu Thr Cys Thr Leu Thr Gly Leu Arg Asp Ala Ser Gly Ala Thr
        35                  40                  45

Phe Thr Trp Thr Pro Ser Ser Gly Lys Ser Ala Val Gln Gly Pro Pro
50                  55                  60

Glu Arg Asp Leu Cys Gly Cys Tyr Ser Val Ser Ser Val Leu Pro Gly
65                  70                  75                  80

Cys Ala Gln Pro Trp Asn His Gly Glu Thr Phe Thr Cys Thr Ala Ala
                85                  90                  95

His Pro Glu Leu Lys Thr Pro Leu Thr Ala Asn Ile Thr Lys Ser Gly
            100                 105                 110

Asn Thr Phe Arg Pro Glu Val His Leu Leu Pro Pro Ser Glu Glu
        115                 120                 125

Leu Ala Leu Asn Glu Leu Val Thr Leu Thr Cys Leu Ala Arg Gly Phe
130                 135                 140

Ser Pro Lys Asp Val Leu Val Arg Trp Leu Gln Gly Ser Gln Glu Leu
```

```
            145                 150                 155                 160
Pro Arg Glu Lys Tyr Leu Thr Trp Ala Ser Arg Gln Glu Pro Ser Gln
                165                 170                 175

Gly Thr Thr Thr Phe Ala Val Thr Ser Ile Leu Arg Val Ala Ala Glu
                180                 185                 190

Asp Trp Lys Lys Gly Asp Thr Phe Ser Cys Met Val Gly His Glu Ala
                195                 200                 205

Leu Pro Leu Ala Phe Thr Gln Lys Thr Ile Asp Arg Met Ala Gly Lys
210                 215                 220

Pro Thr His Val Asn Val Ser Val Val Met Ala Glu Val Asp Gly Thr
225                 230                 235                 240

Cys Tyr

<210> SEQ ID NO 19
<211> LENGTH: 286
<212> TYPE: PRT
<213> ORGANISM: Homo sapiens

<400> SEQUENCE: 19

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
                20                  25                  30

Thr Thr Arg Asn Thr Gly Arg Gly Gly Glu Glu Lys Lys Lys Glu Lys
                35                  40                  45

Glu Lys Glu Glu Gln Glu Glu Arg Glu Thr Lys Thr Pro Glu Cys Pro
50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
                100                 105                 110

Pro Thr Gly Gly Val Glu Glu Gly Leu Leu Glu Arg His Ser Asn Gly
                115                 120                 125

Ser Gln Ser Gln His Ser Arg Leu Thr Leu Pro Arg Ser Leu Trp Asn
130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
                180                 185                 190

Trp Leu Leu Cys Glu Val Ser Gly Phe Ser Pro Pro Asn Ile Leu Leu
                195                 200                 205

Met Trp Leu Glu Asp Gln Arg Glu Val Asn Thr Ser Gly Phe Ala Pro
210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
                260                 265                 270

Ser Leu Glu Val Ser Tyr Val Thr Asp His Gly Pro Met Lys
```

```
                    275                 280                 285

<210> SEQ ID NO 20
<211> LENGTH: 325
<212> TYPE: PRT
<213> ORGANISM: Homo sapiens

<400> SEQUENCE: 20

Val Cys Ser Arg Asp Phe Thr Pro Pro Thr Val Lys Ile Leu Gln Ser
1               5                   10                  15

Ser Cys Asp Gly Gly His Phe Pro Pro Thr Ile Gln Leu Leu Cys
            20                  25                  30

Leu Val Ser Gly Tyr Thr Pro Gly Thr Ile Asn Ile Thr Trp Leu Glu
        35                  40                  45

Asp Gly Gln Val Met Asp Val Asp Leu Ser Thr Ala Ser Thr Thr Gln
    50                  55                  60

Glu Gly Glu Leu Ala Ser Thr Gln Ser Glu Leu Thr Leu Ser Gln Lys
65                  70                  75                  80

His Trp Leu Ser Asp Arg Thr Tyr Thr Cys Gln Val Thr Tyr Gln Gly
                85                  90                  95

His Thr Phe Glu Asp Ser Thr Lys Lys Cys Ala Asp Ser Asn Pro Arg
            100                 105                 110

Gly Val Ser Ala Tyr Leu Ser Arg Pro Ser Pro Phe Asp Leu Phe Ile
        115                 120                 125

Arg Lys Ser Pro Thr Ile Thr Cys Leu Val Val Asp Leu Ala Pro Ser
130                 135                 140

Lys Gly Thr Val Asn Leu Thr Trp Ser Arg Ala Ser Gly Lys Pro Val
145                 150                 155                 160

Asn His Ser Thr Arg Lys Glu Glu Lys Gln Arg Asn Gly Thr Leu Thr
                165                 170                 175

Val Thr Ser Thr Leu Pro Val Gly Thr Arg Asp Trp Ile Glu Gly Glu
            180                 185                 190

Thr Tyr Gln Cys Arg Val Thr His Pro His Leu Pro Arg Ala Leu Met
        195                 200                 205

Arg Ser Thr Thr Lys Thr Ser Gly Pro Arg Ala Ala Pro Glu Val Tyr
210                 215                 220

Ala Phe Ala Thr Pro Glu Trp Pro Gly Ser Arg Asp Lys Arg Thr Leu
225                 230                 235                 240

Ala Cys Leu Ile Gln Asn Phe Met Pro Glu Asp Ile Ser Val Gln Trp
                245                 250                 255

Leu His Asn Glu Val Gln Leu Pro Asp Ala Arg His Ser Thr Thr Gln
            260                 265                 270

Pro Arg Lys Thr Lys Gly Ser Gly Phe Phe Val Phe Ser Arg Leu Glu
        275                 280                 285

Val Thr Arg Ala Glu Trp Glu Gln Lys Asp Glu Phe Ile Cys Arg Ala
    290                 295                 300

Val His Glu Ala Ala Ser Pro Ser Gln Thr Val Gln Arg Ala Val Ser
305                 310                 315                 320

Val Asn Pro Gly Lys
                325

<210> SEQ ID NO 21
<211> LENGTH: 351
<212> TYPE: PRT
<213> ORGANISM: Homo sapiens
```

<400> SEQUENCE: 21

| Leu | Pro | Val | Ile | Ala | Glu | Leu | Pro | Pro | Lys | Val | Ser | Val | Phe | Val | Pro |
|---|---|---|---|---|---|---|---|---|---|---|---|---|---|---|---|
| 1 | | | | 5 | | | | | 10 | | | | | 15 | |

| Pro | Arg | Asp | Gly | Phe | Phe | Gly | Asn | Pro | Arg | Lys | Ser | Lys | Leu | Ile | Cys |
| | | | 20 | | | | | 25 | | | | | 30 | | |

| Gln | Ala | Thr | Gly | Phe | Ser | Pro | Arg | Gln | Ile | Gln | Val | Ser | Trp | Leu | Arg |
| | | 35 | | | | | 40 | | | | | 45 | | | |

| Glu | Gly | Lys | Gln | Val | Gly | Ser | Gly | Val | Thr | Thr | Asp | Gln | Val | Gln | Ala |
| | 50 | | | | | 55 | | | | | 60 | | | | |

| Glu | Ala | Lys | Glu | Ser | Gly | Pro | Thr | Thr | Tyr | Lys | Val | Thr | Ser | Thr | Leu |
| 65 | | | | | 70 | | | | | 75 | | | | | 80 |

| Thr | Ile | Lys | Glu | Ser | Asp | Trp | Leu | Ser | Gln | Ser | Met | Phe | Thr | Cys | Arg |
| | | | | 85 | | | | | 90 | | | | | 95 | |

| Val | Asp | His | Arg | Gly | Leu | Thr | Phe | Gln | Gln | Asn | Ala | Ser | Ser | Met | Cys |
| | | | 100 | | | | | 105 | | | | | 110 | | |

| Val | Pro | Asp | Gln | Asp | Thr | Ala | Ile | Arg | Val | Phe | Ala | Ile | Pro | Pro | Ser |
| | | 115 | | | | | 120 | | | | | 125 | | | |

| Phe | Ala | Ser | Ile | Phe | Leu | Thr | Lys | Ser | Thr | Lys | Leu | Thr | Cys | Leu | Val |
| | 130 | | | | | 135 | | | | | 140 | | | | |

| Thr | Asp | Leu | Thr | Thr | Tyr | Asp | Ser | Val | Thr | Ile | Ser | Trp | Thr | Arg | Gln |
| 145 | | | | | 150 | | | | | 155 | | | | | 160 |

| Asn | Gly | Glu | Ala | Val | Lys | Thr | His | Thr | Asn | Ile | Ser | Glu | Ser | His | Pro |
| | | | | 165 | | | | | 170 | | | | | 175 | |

| Asn | Ala | Thr | Phe | Ser | Ala | Val | Gly | Glu | Ala | Ser | Ile | Cys | Glu | Asp | Asp |
| | | | 180 | | | | | 185 | | | | | 190 | | |

| Trp | Asn | Ser | Gly | Glu | Arg | Phe | Thr | Cys | Thr | Val | Thr | His | Thr | Asp | Leu |
| | | 195 | | | | | 200 | | | | | 205 | | | |

| Pro | Ser | Pro | Leu | Lys | Gln | Thr | Ile | Ser | Arg | Pro | Lys | Gly | Val | Ala | Leu |
| | 210 | | | | | 215 | | | | | 220 | | | | |

| His | Arg | Pro | Asp | Val | Tyr | Leu | Leu | Pro | Pro | Ala | Arg | Glu | Gln | Leu | Asn |
| 225 | | | | | 230 | | | | | 235 | | | | | 240 |

| Leu | Arg | Glu | Ser | Ala | Thr | Ile | Thr | Cys | Leu | Val | Thr | Gly | Phe | Ser | Pro |
| | | | | 245 | | | | | 250 | | | | | 255 | |

| Ala | Asp | Val | Phe | Val | Gln | Trp | Met | Gln | Arg | Gly | Gln | Pro | Leu | Ser | Pro |
| | | | 260 | | | | | 265 | | | | | 270 | | |

| Glu | Lys | Tyr | Val | Thr | Ser | Ala | Pro | Met | Pro | Glu | Pro | Gln | Ala | Pro | Gly |
| | | 275 | | | | | 280 | | | | | 285 | | | |

| Arg | Tyr | Phe | Ala | His | Ser | Ile | Leu | Thr | Val | Ser | Glu | Glu | Glu | Trp | Asn |
| | 290 | | | | | 295 | | | | | 300 | | | | |

| Thr | Gly | Glu | Thr | Tyr | Thr | Cys | Val | Val | Ala | His | Glu | Ala | Leu | Pro | Asn |
| 305 | | | | | 310 | | | | | 315 | | | | | 320 |

| Arg | Val | Thr | Glu | Arg | Thr | Val | Asp | Lys | Ser | Thr | Gly | Lys | Pro | Thr | Leu |
| | | | | 325 | | | | | 330 | | | | | 335 | |

| Tyr | Asn | Val | Ser | Leu | Val | Met | Ser | Asp | Thr | Ala | Gly | Thr | Cys | Tyr |
| | | | 340 | | | | | 345 | | | | | 350 | |

<210> SEQ ID NO 22
<211> LENGTH: 402
<212> TYPE: PRT
<213> ORGANISM: Artificial Sequence
<220> FEATURE:
<223> OTHER INFORMATION: Synthetic

<400> SEQUENCE: 22

Met Gly Arg Gly Leu Leu Arg Gly Leu Trp Pro Leu His Ile Val Leu

```
1               5                    10                   15
Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys
            115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Lys
145                 150                 155                 160

Pro Ser Asn Thr Lys Val Asp Lys Arg Val Glu Pro Lys Ser Cys Asp
                165                 170                 175

Lys Thr His Thr Cys Pro Pro Cys Pro Ala Pro Glu Leu Leu Gly Gly
            180                 185                 190

Pro Ser Val Phe Leu Phe Pro Pro Lys Pro Lys Asp Thr Leu Met Ile
        195                 200                 205

Ser Arg Thr Pro Glu Val Thr Cys Val Val Val Asp Val Ser His Glu
    210                 215                 220

Asp Pro Glu Val Lys Phe Asn Trp Tyr Val Asp Gly Val Glu Val His
225                 230                 235                 240

Asn Ala Lys Thr Lys Pro Arg Glu Glu Gln Tyr Asn Ser Thr Tyr Arg
                245                 250                 255

Val Val Ser Val Leu Thr Val Leu His Gln Asp Trp Leu Asn Gly Lys
            260                 265                 270

Glu Tyr Lys Cys Lys Val Ser Asn Lys Ala Leu Pro Ala Pro Ile Glu
        275                 280                 285

Lys Thr Ile Ser Lys Ala Lys Gly Gln Pro Arg Glu Pro Gln Val Tyr
    290                 295                 300

Thr Leu Pro Pro Ser Arg Asp Glu Leu Thr Lys Asn Gln Val Ser Leu
305                 310                 315                 320

Thr Cys Leu Val Lys Gly Phe Tyr Pro Ser Asp Ile Ala Val Glu Trp
                325                 330                 335

Glu Ser Asn Gly Gln Pro Glu Asn Asn Tyr Lys Thr Thr Pro Pro Val
            340                 345                 350

Leu Asp Ser Asp Gly Ser Phe Phe Leu Tyr Ser Lys Leu Thr Val Asp
        355                 360                 365

Lys Ser Arg Trp Gln Gln Gly Asn Val Phe Ser Cys Ser Val Met His
    370                 375                 380

Glu Ala Leu His Asn His Tyr Thr Gln Lys Ser Leu Ser Leu Ser Pro
385                 390                 395                 400

Gly Lys

<210> SEQ ID NO 23
<211> LENGTH: 398
```

<212> TYPE: PRT
<213> ORGANISM: Artificial Sequence
<220> FEATURE:
<223> OTHER INFORMATION: Synthetic

<400> SEQUENCE: 23

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Lys
145                 150                 155                 160

Pro Ser Asn Thr Lys Val Asp Lys Thr Val Glu Arg Lys Cys Cys Val
                165                 170                 175

Glu Cys Pro Pro Cys Pro Ala Pro Pro Val Ala Gly Pro Ser Val Phe
            180                 185                 190

Leu Phe Pro Pro Lys Pro Lys Asp Thr Leu Met Ile Ser Arg Thr Pro
            195                 200                 205

Glu Val Thr Cys Val Val Val Asp Val Ser His Glu Asp Pro Glu Val
210                 215                 220

Gln Phe Asn Trp Tyr Val Asp Gly Val Glu Val His Asn Ala Lys Thr
225                 230                 235                 240

Lys Pro Arg Glu Glu Gln Phe Asn Ser Thr Phe Arg Val Val Ser Val
                245                 250                 255

Leu Thr Val Val His Gln Asp Trp Leu Asn Gly Lys Glu Tyr Lys Cys
            260                 265                 270

Lys Val Ser Asn Lys Gly Leu Pro Ala Pro Ile Glu Lys Thr Ile Ser
            275                 280                 285

Lys Thr Lys Gly Gln Pro Arg Glu Pro Gln Val Tyr Thr Leu Pro Pro
290                 295                 300

Ser Arg Glu Glu Met Thr Lys Asn Gln Val Ser Leu Thr Cys Leu Val
305                 310                 315                 320

Lys Gly Phe Tyr Pro Ser Asp Ile Ser Val Glu Trp Glu Ser Asn Gly
                325                 330                 335

Gln Pro Glu Asn Asn Tyr Lys Thr Thr Pro Pro Met Leu Asp Ser Asp
            340                 345                 350

Gly Ser Phe Phe Leu Tyr Ser Lys Leu Thr Val Asp Lys Ser Arg Trp
            355                 360                 365

Gln Gln Gly Asn Val Phe Ser Cys Ser Val Met His Glu Ala Leu His
370                 375                 380
```

```
Asn His Tyr Thr Gln Lys Ser Leu Ser Leu Ser Pro Gly Lys
385                 390                 395
```

```
<210> SEQ ID NO 24
<211> LENGTH: 449
<212> TYPE: PRT
<213> ORGANISM: Artificial Sequence
<220> FEATURE:
<223> OTHER INFORMATION: Synthetic

<400> SEQUENCE: 24

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Lys
145                 150                 155                 160

Pro Ser Asn Thr Lys Val Asp Lys Arg Val Glu Leu Lys Thr Pro Leu
                165                 170                 175

Gly Asp Thr Thr His Thr Cys Pro Arg Cys Pro Glu Pro Lys Ser Cys
            180                 185                 190

Asp Thr Pro Pro Pro Cys Pro Arg Cys Pro Glu Pro Lys Ser Cys Asp
        195                 200                 205

Thr Pro Pro Pro Cys Pro Arg Cys Pro Glu Pro Lys Ser Cys Asp Thr
210                 215                 220

Pro Pro Pro Cys Pro Arg Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Lys Trp Tyr Val Asp Gly Val Glu Val His Asn
        275                 280                 285

Ala Lys Thr Lys Pro Arg Glu Glu Gln Tyr Asn Ser Thr Phe Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Thr Lys Gly Gln Pro Arg Glu Pro Gln Val Tyr Thr
            340                 345                 350
```

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Ser Gly Gln Pro Glu Asn Asn Tyr Asn Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Ile Phe Ser Cys Ser Val Met His Glu
            420                 425                 430

Ala Leu His Asn Arg Phe Thr Gln Lys Ser Leu Ser Leu Ser Pro Gly
        435                 440                 445

Lys

<210> SEQ ID NO 25
<211> LENGTH: 399
<212> TYPE: PRT
<213> ORGANISM: Artificial Sequence
<220> FEATURE:
<223> OTHER INFORMATION: Synthetic

<400> SEQUENCE: 25

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Lys
145                 150                 155                 160

Pro Ser Asn Thr Lys Val Asp Lys Arg Val Glu Ser Lys Tyr Gly Pro
                165                 170                 175

Pro Cys Pro Ser Cys Pro Ala Pro Glu Phe Leu Gly Gly Pro Ser Val
            180                 185                 190

Phe Leu Phe Pro Pro Lys Pro Lys Asp Thr Leu Met Ile Ser Arg Thr
        195                 200                 205

Pro Glu Val Thr Cys Val Val Val Asp Val Ser Gln Glu Asp Pro Glu
    210                 215                 220

Val Gln Phe Asn Trp Tyr Val Asp Gly Val Glu Val His Asn Ala Lys
225                 230                 235                 240

Thr Lys Pro Arg Glu Glu Gln Phe Asn Ser Thr Tyr Arg Val Val Ser
                245                 250                 255

Val Leu Thr Val Leu His Gln Asp Trp Leu Asn Gly Lys Glu Tyr Lys

```
            260                 265                 270
Cys Lys Val Ser Asn Lys Gly Leu Pro Ser Ser Ile Glu Lys Thr Ile
        275                 280                 285

Ser Lys Ala Lys Gly Gln Pro Arg Glu Pro Gln Val Tyr Thr Leu Pro
    290                 295                 300

Pro Ser Gln Glu Glu Met Thr Lys Asn Gln Val Ser Leu Thr Cys Leu
305                 310                 315                 320

Val Lys Gly Phe Tyr Pro Ser Asp Ile Ala Val Glu Trp Ser Asn
                325                 330                 335

Gly Gln Pro Glu Asn Asn Tyr Lys Thr Thr Pro Val Leu Asp Ser
            340                 345                 350

Asp Gly Ser Phe Phe Leu Tyr Ser Arg Leu Thr Val Asp Lys Ser Arg
        355                 360                 365

Trp Gln Glu Gly Asn Val Phe Ser Cys Ser Val Met His Glu Ala Leu
        370                 375                 380

His Asn His Tyr Thr Gln Lys Ser Leu Ser Leu Ser Leu Gly Lys
385                 390                 395

<210> SEQ ID NO 26
<211> LENGTH: 426
<212> TYPE: PRT
<213> ORGANISM: Artificial Sequence
<220> FEATURE:
<223> OTHER INFORMATION: Synthetic

<400> SEQUENCE: 26

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Val
145                 150                 155                 160

Lys His Tyr Thr Asn Pro Ser Gln Asp Val Thr Val Pro Cys Pro Val
                165                 170                 175

Pro Ser Thr Pro Pro Thr Pro Ser Pro Ser Thr Pro Pro Thr Pro Ser
            180                 185                 190

Pro Ser Cys Cys His Pro Arg Leu Ser Leu His Arg Pro Ala Leu Glu
        195                 200                 205

Asp Leu Leu Leu Gly Ser Glu Ala Asn Leu Thr Cys Thr Leu Thr Gly
    210                 215                 220

Leu Arg Asp Ala Ser Gly Val Thr Phe Thr Trp Thr Pro Ser Ser Gly
```

```
            225                 230                 235                 240

Lys Ser Ala Val Gln Gly Pro Pro Glu Arg Asp Leu Cys Gly Cys Tyr
                245                 250                 255

Ser Val Ser Val Leu Pro Gly Cys Ala Glu Pro Trp Asn His Gly
            260                 265                 270

Lys Thr Phe Thr Cys Thr Ala Ala Tyr Pro Glu Ser Lys Thr Pro Leu
            275                 280                 285

Thr Ala Thr Leu Ser Lys Ser Gly Asn Thr Phe Arg Pro Glu Val His
        290                 295                 300

Leu Leu Pro Pro Ser Glu Glu Leu Ala Leu Asn Glu Leu Val Thr
305                 310                 315                 320

Leu Thr Cys Leu Ala Arg Gly Phe Ser Pro Lys Asp Val Leu Val Arg
                325                 330                 335

Trp Leu Gln Gly Ser Gln Glu Leu Pro Arg Glu Lys Tyr Leu Thr Trp
            340                 345                 350

Ala Ser Arg Gln Glu Pro Ser Gln Gly Thr Thr Thr Phe Ala Val Thr
        355                 360                 365

Ser Ile Leu Arg Val Ala Ala Glu Asp Trp Lys Lys Gly Asp Thr Phe
370                 375                 380

Ser Cys Met Val Gly His Glu Ala Leu Pro Leu Ala Phe Thr Gln Lys
385                 390                 395                 400

Thr Ile Asp Arg Leu Ala Gly Lys Pro Thr His Val Asn Val Ser Val
                405                 410                 415

Val Met Ala Glu Val Asp Gly Thr Cys Tyr
                420                 425

<210> SEQ ID NO 27
<211> LENGTH: 413
<212> TYPE: PRT
<213> ORGANISM: Artificial Sequence
<220> FEATURE:
<223> OTHER INFORMATION: Synthetic

<400> SEQUENCE: 27

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Val
145                 150                 155                 160

Lys His Tyr Thr Asn Pro Ser Gln Asp Val Thr Val Pro Cys Pro Val
```

```
                    165                 170                 175
Pro Pro Pro Pro Pro Cys Cys His Pro Arg Leu Ser Leu His Arg Pro
                180                 185                 190

Ala Leu Glu Asp Leu Leu Leu Gly Ser Glu Ala Asn Leu Thr Cys Thr
            195                 200                 205

Leu Thr Gly Leu Arg Asp Ala Ser Gly Ala Thr Phe Thr Trp Thr Pro
        210                 215                 220

Ser Ser Gly Lys Ser Ala Val Gln Gly Pro Glu Arg Asp Leu Cys
225                 230                 235                 240

Gly Cys Tyr Ser Val Ser Ser Val Leu Pro Gly Cys Ala Gln Pro Trp
                245                 250                 255

Asn His Gly Glu Thr Phe Thr Cys Thr Ala Ala His Pro Glu Leu Lys
            260                 265                 270

Thr Pro Leu Thr Ala Asn Ile Thr Lys Ser Gly Asn Thr Phe Arg Pro
        275                 280                 285

Glu Val His Leu Leu Pro Pro Pro Ser Glu Glu Leu Ala Leu Asn Glu
    290                 295                 300

Leu Val Thr Leu Thr Cys Leu Ala Arg Gly Phe Ser Pro Lys Asp Val
305                 310                 315                 320

Leu Val Arg Trp Leu Gln Gly Ser Gln Glu Leu Pro Arg Glu Lys Tyr
                325                 330                 335

Leu Thr Trp Ala Ser Arg Gln Glu Pro Ser Gln Gly Thr Thr Thr Phe
            340                 345                 350

Ala Val Thr Ser Ile Leu Arg Val Ala Ala Glu Asp Trp Lys Lys Gly
        355                 360                 365

Asp Thr Phe Ser Cys Met Val Gly His Glu Ala Leu Pro Leu Ala Phe
    370                 375                 380

Thr Gln Lys Thr Ile Asp Arg Met Ala Gly Lys Pro Thr His Val Asn
385                 390                 395                 400

Val Ser Val Val Met Ala Glu Val Asp Gly Thr Cys Tyr
                405                 410

<210> SEQ ID NO 28
<211> LENGTH: 455
<212> TYPE: PRT
<213> ORGANISM: Artificial Sequence
<220> FEATURE:
<223> OTHER INFORMATION: Synthetic

<400> SEQUENCE: 28

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
```

```
                115                 120                 125
Pro Gly Glu Thr Phe Phe Met Cys Ser Cys Ser Ser Asp Glu Cys Asn
            130                 135                 140

Asp Asn Ile Ile Phe Ser Glu Glu Tyr Asn Thr Ser Asn Pro Asp Thr
145                 150                 155                 160

Ala Ser Lys Ser Lys Lys Glu Ile Phe Arg Trp Pro Glu Ser Pro Lys
                165                 170                 175

Ala Gln Ala Ser Ser Val Pro Thr Ala Gln Pro Gln Ala Glu Gly Ser
            180                 185                 190

Leu Ala Lys Ala Thr Thr Ala Pro Ala Thr Thr Arg Asn Thr Gly Arg
        195                 200                 205

Gly Gly Glu Glu Lys Lys Lys Glu Lys Lys Glu Glu Gln Glu Glu
    210                 215                 220

Arg Glu Thr Lys Thr Pro Glu Cys Pro Ser His Thr Gln Pro Leu Gly
225                 230                 235                 240

Val Tyr Leu Leu Thr Pro Ala Val Gln Asp Leu Trp Leu Arg Asp Lys
                245                 250                 255

Ala Thr Phe Thr Cys Phe Val Val Gly Ser Asp Leu Lys Asp Ala His
            260                 265                 270

Leu Thr Trp Glu Val Ala Gly Lys Val Pro Thr Gly Gly Val Glu Glu
        275                 280                 285

Gly Leu Leu Glu Arg His Ser Asn Gly Ser Gln Ser Gln His Ser Arg
    290                 295                 300

Leu Thr Leu Pro Arg Ser Leu Trp Asn Ala Gly Thr Ser Val Thr Cys
305                 310                 315                 320

Thr Leu Asn His Pro Ser Leu Pro Pro Gln Arg Leu Met Ala Leu Arg
                325                 330                 335

Glu Pro Ala Ala Gln Ala Pro Val Lys Leu Ser Leu Asn Leu Leu Ala
            340                 345                 350

Ser Ser Asp Pro Pro Glu Ala Ala Ser Trp Leu Leu Cys Glu Val Ser
        355                 360                 365

Gly Phe Ser Pro Pro Asn Ile Leu Leu Met Trp Leu Glu Asp Gln Arg
    370                 375                 380

Glu Val Asn Thr Ser Gly Phe Ala Pro Ala Arg Pro Pro Gln Pro
385                 390                 395                 400

Gly Ser Thr Thr Phe Trp Ala Trp Ser Val Leu Arg Val Pro Ala Pro
                405                 410                 415

Pro Ser Pro Gln Pro Ala Thr Tyr Thr Cys Val Val Ser His Glu Asp
            420                 425                 430

Ser Arg Thr Leu Leu Asn Ala Ser Arg Ser Leu Glu Val Ser Tyr Val
        435                 440                 445

Thr Asp His Gly Pro Met Lys
    450                 455

<210> SEQ ID NO 29
<211> LENGTH: 498
<212> TYPE: PRT
<213> ORGANISM: Artificial Sequence
<220> FEATURE:
<223> OTHER INFORMATION: Synthetic

<400> SEQUENCE: 29

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
```

```
            20                  25                  30
Asn Asn Asp Met Ile Val Thr Asp Asn Asn Gly Ala Val Lys Phe Pro
             35                  40                  45
Gln Leu Cys Lys Phe Cys Asp Val Arg Phe Ser Thr Cys Asp Asn Gln
 50                  55                  60
Lys Ser Cys Met Ser Asn Cys Ser Ile Thr Ser Ile Cys Glu Lys Pro
 65                  70                  75                  80
Gln Glu Val Cys Val Ala Val Trp Arg Lys Asn Asp Glu Asn Ile Thr
                     85                  90                  95
Leu Glu Thr Val Cys His Asp Pro Lys Leu Pro Tyr His Asp Phe Ile
                100                 105                 110
Leu Glu Asp Ala Ala Ser Pro Lys Cys Ile Met Lys Glu Lys Lys Lys
                115                 120                 125
Pro Gly Glu Thr Phe Phe Met Cys Ser Cys Ser Ser Asp Glu Cys Asn
                130                 135                 140
Asp Asn Ile Ile Phe Ser Glu Glu Tyr Asn Thr Ser Asn Pro Asp Thr
145                 150                 155                 160
Pro Ser Ser Thr Asp Trp Val Asp Asn Lys Thr Phe Ser Val Cys Ser
                165                 170                 175
Arg Asp Phe Thr Pro Pro Thr Val Lys Ile Leu Gln Ser Ser Cys Asp
                180                 185                 190
Gly Gly Gly His Phe Pro Pro Thr Ile Gln Leu Leu Cys Leu Val Ser
                195                 200                 205
Gly Tyr Thr Pro Gly Thr Ile Asn Ile Thr Trp Leu Glu Asp Gly Gln
                210                 215                 220
Val Met Asp Val Asp Leu Ser Thr Ala Ser Thr Thr Gln Glu Gly Glu
225                 230                 235                 240
Leu Ala Ser Thr Gln Ser Glu Leu Thr Leu Ser Gln Lys His Trp Leu
                245                 250                 255
Ser Asp Arg Thr Tyr Thr Cys Gln Val Thr Tyr Gln Gly His Thr Phe
                260                 265                 270
Glu Asp Ser Thr Lys Lys Cys Ala Asp Ser Asn Pro Arg Gly Val Ser
                275                 280                 285
Ala Tyr Leu Ser Arg Pro Ser Pro Phe Asp Leu Phe Ile Arg Lys Ser
                290                 295                 300
Pro Thr Ile Thr Cys Leu Val Val Asp Leu Ala Pro Ser Lys Gly Thr
305                 310                 315                 320
Val Asn Leu Thr Trp Ser Arg Ala Ser Gly Lys Pro Val Asn His Ser
                325                 330                 335
Thr Arg Lys Glu Glu Lys Gln Arg Asn Gly Thr Leu Thr Val Thr Ser
                340                 345                 350
Thr Leu Pro Val Gly Thr Arg Asp Trp Ile Glu Gly Thr Tyr Gln
                355                 360                 365
Cys Arg Val Thr His Pro His Leu Pro Arg Ala Leu Met Arg Ser Thr
                370                 375                 380
Thr Lys Thr Ser Gly Pro Arg Ala Ala Pro Glu Val Tyr Ala Phe Ala
385                 390                 395                 400
Thr Pro Glu Trp Pro Gly Ser Arg Asp Lys Arg Thr Leu Ala Cys Leu
                405                 410                 415
Ile Gln Asn Phe Met Pro Glu Asp Ile Ser Val Gln Trp Leu His Asn
                420                 425                 430
Glu Val Gln Leu Pro Asp Ala Arg His Ser Thr Thr Gln Pro Arg Lys
                435                 440                 445
```

Thr Lys Gly Ser Gly Phe Phe Val Phe Ser Arg Leu Glu Val Thr Arg
    450                 455                 460

Ala Glu Trp Glu Gln Lys Asp Glu Phe Ile Cys Arg Ala Val His Glu
465                 470                 475                 480

Ala Ala Ser Pro Ser Gln Thr Val Gln Arg Ala Val Ser Val Asn Pro
                485                 490                 495

Gly Lys

<210> SEQ ID NO 30
<211> LENGTH: 523
<212> TYPE: PRT
<213> ORGANISM: Artificial Sequence
<220> FEATURE:
<223> OTHER INFORMATION: Synthetic

<400> SEQUENCE: 30

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Val
145                 150                 155                 160

Gln His Pro Asn Gly Asn Lys Glu Lys Asn Val Pro Leu Pro Val Ile
                165                 170                 175

Ala Glu Leu Pro Pro Lys Val Ser Val Phe Val Pro Pro Arg Asp Gly
            180                 185                 190

Phe Phe Gly Asn Pro Arg Lys Ser Lys Leu Ile Cys Gln Ala Thr Gly
        195                 200                 205

Phe Ser Pro Arg Gln Ile Gln Val Ser Trp Leu Arg Glu Gly Lys Gln
    210                 215                 220

Val Gly Ser Gly Val Thr Thr Asp Gln Val Gln Ala Glu Ala Lys Glu
225                 230                 235                 240

Ser Gly Pro Thr Thr Tyr Lys Val Thr Ser Thr Leu Thr Ile Lys Glu
                245                 250                 255

Ser Asp Trp Leu Ser Gln Ser Met Phe Thr Cys Arg Val Asp His Arg
            260                 265                 270

Gly Leu Thr Phe Gln Gln Asn Ala Ser Ser Met Cys Val Pro Asp Gln
        275                 280                 285

Asp Thr Ala Ile Arg Val Phe Ala Ile Pro Pro Ser Phe Ala Ser Ile
    290                 295                 300

```
Phe Leu Thr Lys Ser Thr Lys Leu Thr Cys Leu Val Thr Asp Leu Thr
305                 310                 315                 320

Thr Tyr Asp Ser Val Thr Ile Ser Trp Thr Arg Gln Asn Gly Glu Ala
            325                 330                 335

Val Lys Thr His Thr Asn Ile Ser Glu Ser His Pro Asn Ala Thr Phe
            340                 345                 350

Ser Ala Val Gly Glu Ala Ser Ile Cys Glu Asp Asp Trp Asn Ser Gly
            355                 360                 365

Glu Arg Phe Thr Cys Thr Val Thr His Thr Asp Leu Pro Ser Pro Leu
        370                 375                 380

Lys Gln Thr Ile Ser Arg Pro Lys Gly Val Ala Leu His Arg Pro Asp
385                 390                 395                 400

Val Tyr Leu Leu Pro Pro Ala Arg Glu Gln Leu Asn Leu Arg Glu Ser
                405                 410                 415

Ala Thr Ile Thr Cys Leu Val Thr Gly Phe Ser Pro Ala Asp Val Phe
            420                 425                 430

Val Gln Trp Met Gln Arg Gly Gln Pro Leu Ser Pro Glu Lys Tyr Val
            435                 440                 445

Thr Ser Ala Pro Met Pro Glu Pro Gln Ala Pro Gly Arg Tyr Phe Ala
450                 455                 460

His Ser Ile Leu Thr Val Ser Glu Glu Glu Trp Asn Thr Gly Glu Thr
465                 470                 475                 480

Tyr Thr Cys Val Val Ala His Glu Ala Leu Pro Asn Arg Val Thr Glu
                485                 490                 495

Arg Thr Val Asp Lys Ser Thr Gly Lys Pro Thr Leu Tyr Asn Val Ser
            500                 505                 510

Leu Val Met Ser Asp Thr Ala Gly Thr Cys Tyr
            515                 520

<210> SEQ ID NO 31
<211> LENGTH: 402
<212> TYPE: PRT
<213> ORGANISM: Artificial Sequence
<220> FEATURE:
<223> OTHER INFORMATION: Synthetic

<400> SEQUENCE: 31

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140
```

```
Asp Asn Ile Ile Phe Ser Glu Glu Tyr Asn Thr Ser Asn Pro Asp Tyr
145                 150                 155                 160

Val Pro Lys Glu Phe Asn Ala Glu Thr Phe Thr Pro Lys Ser Cys Asp
                165                 170                 175

Lys Thr His Thr Cys Pro Pro Cys Pro Ala Pro Glu Leu Leu Gly Gly
            180                 185                 190

Pro Ser Val Phe Leu Phe Pro Pro Lys Pro Lys Asp Thr Leu Met Ile
        195                 200                 205

Ser Arg Thr Pro Glu Val Thr Cys Val Val Val Asp Val Ser His Glu
210                 215                 220

Asp Pro Glu Val Lys Phe Asn Trp Tyr Val Asp Gly Val Glu Val His
225                 230                 235                 240

Asn Ala Lys Thr Lys Pro Arg Glu Glu Gln Tyr Asn Ser Thr Tyr Arg
                245                 250                 255

Val Val Ser Val Leu Thr Val Leu His Gln Asp Trp Leu Asn Gly Lys
            260                 265                 270

Glu Tyr Lys Cys Lys Val Ser Asn Lys Ala Leu Pro Ala Pro Ile Glu
        275                 280                 285

Lys Thr Ile Ser Lys Ala Lys Gly Gln Pro Arg Glu Pro Gln Val Tyr
290                 295                 300

Thr Leu Pro Pro Ser Arg Asp Glu Leu Thr Lys Asn Gln Val Ser Leu
305                 310                 315                 320

Thr Cys Leu Val Lys Gly Phe Tyr Pro Ser Asp Ile Ala Val Glu Trp
                325                 330                 335

Glu Ser Asn Gly Gln Pro Glu Asn Asn Tyr Lys Thr Thr Pro Pro Val
            340                 345                 350

Leu Asp Ser Asp Gly Ser Phe Phe Leu Tyr Ser Lys Leu Thr Val Asp
        355                 360                 365

Lys Ser Arg Trp Gln Gln Gly Asn Val Phe Ser Cys Ser Val Met His
370                 375                 380

Glu Ala Leu His Asn His Tyr Thr Gln Lys Ser Leu Ser Leu Ser Pro
385                 390                 395                 400

Gly Lys

<210> SEQ ID NO 32
<211> LENGTH: 402
<212> TYPE: PRT
<213> ORGANISM: Artificial Sequence
<220> FEATURE:
<223> OTHER INFORMATION: Synthetic

<400> SEQUENCE: 32

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
```

Leu Glu Asp Ala Ala Ser Pro Lys Cys Ile Met Lys Glu Lys Lys
            115                 120                 125

Pro Gly Glu Thr Phe Phe Met Cys Ser Cys Ser Ser Asp Glu Cys Asn
        130                 135                 140

Asp Asn Ile Ile Phe Ser Glu Glu Tyr Asn Thr Ser Asn Pro Asp Arg
145                 150                 155                 160

Glu Lys Gln Thr Asp Glu Ile Lys Asp Thr Arg Pro Lys Ser Cys Asp
                165                 170                 175

Lys Thr His Thr Cys Pro Pro Cys Pro Ala Pro Glu Leu Leu Gly Gly
            180                 185                 190

Pro Ser Val Phe Leu Phe Pro Pro Lys Pro Lys Asp Thr Leu Met Ile
        195                 200                 205

Ser Arg Thr Pro Glu Val Thr Cys Val Val Val Asp Val Ser His Glu
    210                 215                 220

Asp Pro Glu Val Lys Phe Asn Trp Tyr Val Asp Gly Val Glu Val His
225                 230                 235                 240

Asn Ala Lys Thr Lys Pro Arg Glu Glu Gln Tyr Asn Ser Thr Tyr Arg
                245                 250                 255

Val Val Ser Val Leu Thr Val Leu His Gln Asp Trp Leu Asn Gly Lys
            260                 265                 270

Glu Tyr Lys Cys Lys Val Ser Asn Lys Ala Leu Pro Ala Pro Ile Glu
        275                 280                 285

Lys Thr Ile Ser Lys Ala Lys Gly Gln Pro Arg Glu Pro Gln Val Tyr
    290                 295                 300

Thr Leu Pro Pro Ser Arg Asp Glu Leu Thr Lys Asn Gln Val Ser Leu
305                 310                 315                 320

Thr Cys Leu Val Lys Gly Phe Tyr Pro Ser Asp Ile Ala Val Glu Trp
                325                 330                 335

Glu Ser Asn Gly Gln Pro Glu Asn Asn Tyr Lys Thr Thr Pro Pro Val
            340                 345                 350

Leu Asp Ser Asp Gly Ser Phe Phe Leu Tyr Ser Lys Leu Thr Val Asp
        355                 360                 365

Lys Ser Arg Trp Gln Gln Gly Asn Val Phe Ser Cys Ser Val Met His
    370                 375                 380

Glu Ala Leu His Asn His Tyr Thr Gln Lys Ser Leu Ser Leu Ser Pro
385                 390                 395                 400

Gly Lys

<210> SEQ ID NO 33
<211> LENGTH: 394
<212> TYPE: PRT
<213> ORGANISM: Artificial Sequence
<220> FEATURE:
<223> OTHER INFORMATION: Synthetic

<400> SEQUENCE: 33

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Pro Lys Ser Val
            20                  25                  30

Asn Ser Asp Val Met Ala Ser Asp Asn Gly Gly Ala Val Lys Leu Pro
        35                  40                  45

Gln Leu Cys Lys Phe Cys Asp Val Arg Leu Ser Thr Cys Asp Asn Gln
    50                  55                  60

Lys Ser Cys Met Ser Asn Cys Ser Ile Thr Ala Ile Cys Glu Lys Pro
65                  70                  75                  80

His Glu Val Cys Val Ala Val Trp Arg Lys Asn Asp Lys Asn Ile Thr
                85                  90                  95

Leu Glu Thr Val Cys His Asp Pro Lys Leu Thr Tyr His Gly Phe Thr
            100                 105                 110

Leu Glu Asp Ala Ala Ser Pro Lys Cys Val Met Lys Glu Lys Lys Arg
        115                 120                 125

Ala Gly Glu Thr Phe Phe Met Cys Ala Cys Asn Met Glu Glu Cys Asn
    130                 135                 140

Asp Tyr Ile Ile Phe Ser Glu Glu Tyr Thr Thr Ser Ser Pro Asp Ser
145                 150                 155                 160

Thr Lys Val Asp Lys Lys Ile Val Pro Arg Asp Cys Gly Cys Lys Pro
                165                 170                 175

Cys Ile Cys Thr Val Pro Glu Val Ser Ser Val Phe Ile Phe Pro Pro
            180                 185                 190

Lys Pro Lys Asp Val Leu Thr Ile Thr Leu Thr Pro Lys Val Thr Cys
        195                 200                 205

Val Val Val Asp Ile Ser Lys Asp Asp Pro Glu Val Gln Phe Ser Trp
    210                 215                 220

Phe Val Asp Asp Val Glu Val His Thr Ala Gln Thr Gln Pro Arg Glu
225                 230                 235                 240

Glu Gln Phe Asn Ser Thr Phe Arg Ser Val Ser Glu Leu Pro Ile Met
                245                 250                 255

His Gln Asp Trp Leu Asn Gly Lys Glu Phe Lys Cys Arg Val Asn Ser
            260                 265                 270

Ala Ala Phe Pro Ala Pro Ile Glu Lys Thr Ile Ser Lys Thr Lys Gly
        275                 280                 285

Arg Pro Lys Ala Pro Gln Val Tyr Thr Ile Pro Pro Pro Lys Glu Gln
    290                 295                 300

Met Ala Lys Asp Lys Val Ser Leu Thr Cys Met Ile Thr Asp Phe Phe
305                 310                 315                 320

Pro Glu Asp Ile Thr Val Glu Trp Gln Trp Asn Gly Gln Pro Ala Glu
                325                 330                 335

Asn Tyr Lys Asn Thr Gln Pro Ile Met Asp Thr Asp Gly Ser Tyr Phe
            340                 345                 350

Val Tyr Ser Lys Leu Asn Val Gln Lys Ser Asn Trp Glu Ala Gly Asn
        355                 360                 365

Thr Phe Thr Cys Ser Val Leu His Glu Gly Leu His Asn His His Thr
    370                 375                 380

Glu Lys Ser Leu Ser His Ser Pro Gly Lys
385                 390

<210> SEQ ID NO 34
<211> LENGTH: 159
<212> TYPE: PRT
<213> ORGANISM: Mus musculus

<400> SEQUENCE: 34

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Pro Lys Ser Val
            20                  25                  30

Asn Ser Asp Val Met Ala Ser Asp Asn Gly Gly Ala Val Lys Leu Pro

```
                35                  40                  45
Gln Leu Cys Lys Phe Cys Asp Val Arg Leu Ser Thr Cys Asp Asn Gln
 50                  55                  60
Lys Ser Cys Met Ser Asn Cys Ser Ile Thr Ala Ile Cys Glu Lys Pro
 65                  70                  75                  80
His Glu Val Cys Val Ala Val Trp Arg Lys Asn Asp Lys Asn Ile Thr
                 85                  90                  95
Leu Glu Thr Val Cys His Asp Pro Lys Leu Thr Tyr His Gly Phe Thr
                100                 105                 110
Leu Glu Asp Ala Ala Ser Pro Lys Cys Val Met Lys Glu Lys Lys Arg
            115                 120                 125
Ala Gly Glu Thr Phe Phe Met Cys Ala Cys Asn Met Glu Glu Cys Asn
        130                 135                 140
Asp Tyr Ile Ile Phe Ser Glu Glu Tyr Thr Thr Ser Ser Pro Asp
145                 150                 155

<210> SEQ ID NO 35
<211> LENGTH: 12
<212> TYPE: PRT
<213> ORGANISM: Mus musculus

<400> SEQUENCE: 35

Ser Thr Lys Val Asp Lys Lys Ile Val Pro Arg Asp
1               5                   10

<210> SEQ ID NO 36
<211> LENGTH: 223
<212> TYPE: PRT
<213> ORGANISM: Mus musculus

<400> SEQUENCE: 36

Cys Gly Cys Lys Pro Cys Ile Cys Thr Val Pro Glu Val Ser Ser Val
1               5                   10                  15
Phe Ile Phe Pro Pro Lys Pro Lys Asp Val Leu Thr Ile Thr Leu Thr
             20                  25                  30
Pro Lys Val Thr Cys Val Val Val Asp Ile Ser Lys Asp Asp Pro Glu
         35                  40                  45
Val Gln Phe Ser Trp Phe Val Asp Asp Val Glu Val His Thr Ala Gln
 50                  55                  60
Thr Gln Pro Arg Glu Glu Gln Phe Asn Ser Thr Phe Arg Ser Val Ser
 65                  70                  75                  80
Glu Leu Pro Ile Met His Gln Asp Trp Leu Asn Gly Lys Glu Phe Lys
                 85                  90                  95
Cys Arg Val Asn Ser Ala Ala Phe Pro Ala Pro Ile Glu Lys Thr Ile
                100                 105                 110
Ser Lys Thr Lys Gly Arg Pro Lys Ala Pro Gln Val Tyr Thr Ile Pro
            115                 120                 125
Pro Pro Lys Glu Gln Met Ala Lys Asp Lys Val Ser Leu Thr Cys Met
        130                 135                 140
Ile Thr Asp Phe Phe Pro Glu Asp Ile Thr Val Glu Trp Gln Trp Asn
145                 150                 155                 160
Gly Gln Pro Ala Glu Asn Tyr Lys Asn Thr Gln Pro Ile Met Asp Thr
                165                 170                 175
Asp Gly Ser Tyr Phe Val Tyr Ser Lys Leu Asn Val Gln Lys Ser Asn
            180                 185                 190
Trp Glu Ala Gly Asn Thr Phe Thr Cys Ser Val Leu His Glu Gly Leu
```

```
                195                 200                 205
His Asn His His Thr Glu Lys Ser Leu Ser His Ser Pro Gly Lys
    210                 215                 220
```

<210> SEQ ID NO 37
<211> LENGTH: 1209
<212> TYPE: DNA
<213> ORGANISM: Artificial Sequence
<220> FEATURE:
<223> OTHER INFORMATION: Synthetic

<400> SEQUENCE: 37

| | | | | | |
|---|---|---|---|---|---|
| atgggtcggg | ggctgctcag | gggcctgtgg | ccgctgcaca | tcgtcctgtg | gacgcgtatc | 60 |
| gccagcacga | tcccaccgca | cgttcagaag | tcggttaata | acgacatgat | agtcactgac | 120 |
| aacaacggtg | cagtcaagtt | tccacaactg | tgtaaatttt | gtgatgtgag | attttccacc | 180 |
| tgtgacaacc | agaaatcctg | catgagcaac | tgcagcatca | cctccatctg | tgagaagcca | 240 |
| caggaagtct | gtgtggctgt | atggagaaag | aatgacgaga | acataacact | agagacagtt | 300 |
| tgccatgacc | ccaagctccc | ctaccatgac | tttattctgg | aagatgctgc | ttctccaaag | 360 |
| tgcattatga | aggaaaaaaa | aaagcctggt | gagactttct | tcatgtgttc | ctgtagctct | 420 |
| gatgagtgca | atgacaacat | catcttctca | gaagaatata | caccagcaa | tcctgacaag | 480 |
| cccagcaaca | ccaaggtgga | caagagagtt | gagcccaaat | cttgtgacaa | aactcacaca | 540 |
| tgcccaccgt | gcccagcacc | tgaactcctg | ggggaccgt | cagtcttcct | cttcccccca | 600 |
| aaacccaagg | acaccctcat | gatctcccgg | acccctgagg | tcacatgcgt | ggtggtggac | 660 |
| gtgagccacg | aagaccctga | ggtcaagttc | aactggtacg | tggacggcgt | ggaggtgcat | 720 |
| aatgccaaga | caaagccgcg | ggaggagcag | tacaacagca | cgtaccgtgt | ggtcagcgtc | 780 |
| ctcaccgtcc | tgcaccagga | ctggctgaat | ggcaaggagt | acaagtgcaa | ggtctccaac | 840 |
| aaagccctcc | cagcccccat | cgagaaaacc | atctccaaag | ccaaagggca | gccccgagaa | 900 |
| ccacaggtgt | acaccctgcc | cccatcccgg | gatgagctga | ccaagaacca | ggtcagcctg | 960 |
| acctgcctgg | tcaaaggctt | ctatcccagc | gacatcgccg | tggagtggga | gagcaatggg | 1020 |
| cagccggaga | acaactacaa | gaccacgcct | cccgtgctgg | actccgacgg | ctccttcttc | 1080 |
| ctctacagca | agctcaccgt | ggacaagagc | aggtggcagc | aggggaacgt | cttctcatgc | 1140 |
| tccgtgatgc | atgaggctct | gcacaaccac | tacacgcaga | agagcctctc | cctgtctccg | 1200 |
| ggtaaatga | | | | | | 1209 |

<210> SEQ ID NO 38
<211> LENGTH: 1194
<212> TYPE: DNA
<213> ORGANISM: Artificial Sequence
<220> FEATURE:
<223> OTHER INFORMATION: Synthetic

<400> SEQUENCE: 38

| | | | | | |
|---|---|---|---|---|---|
| atgggtcggg | ggctgctcag | gggcctgtgg | ccgctgcaca | tcgtcctgtg | gacgcgtatc | 60 |
| gccagcacga | tcccaccgca | cgttcagaag | tcggttaata | acgacatgat | agtcactgac | 120 |
| aacaacggtg | cagtcaagtt | tccacaactg | tgtaaatttt | gtgatgtgag | attttccacc | 180 |
| tgtgacaacc | agaaatcctg | catgagcaac | tgcagcatca | cctccatctg | tgagaagcca | 240 |
| caggaagtct | gtgtggctgt | atggagaaag | aatgacgaga | acataacact | agagacagtt | 300 |
| tgccatgacc | ccaagctccc | ctaccatgac | tttattctgg | aagatgctgc | ttctccaaag | 360 |

```
tgcattatga aggaaaaaaa aaagcctggt gagactttct tcatgtgttc ctgtagctct    420
gatgagtgca atgacaacat catcttctca gaagaatata acaccagcaa tcctgacaag    480
cccagcaaca ccaaggtgga caagacagtt gagcgcaaat gttgtgtcga gtgcccaccg    540
tgcccagcac cacctgtggc aggaccgtca gtcttcctct tccccccaaa acccaaggac    600
accctcatga tctcccggac ccctgaggtc acgtgcgtgg tggtggacgt gagccacgaa    660
gaccccgagg tccagttcaa ctggtacgtg gacggcgtgg aggtgcataa tgccaagaca    720
aagccacggg aggagcagtt caacagcacg ttccgtgtgg tcagcgtcct caccgttgtg    780
caccaggact ggctgaacgg caaggagtac aagtgcaagg tctccaacaa aggcctccca    840
gcccccatcg agaaaaccat ctccaaaacc aaagggcagc cccgagaacc acaggtgtac    900
accctgcccc catcccggga ggagatgacc aagaaccagg tcagcctgac ctgcctggtc    960
aaaggcttct accccagcga catctccgtg gagtgggaga gcaatgggca gccggagaac   1020
aactacaaga ccacacctcc catgctggac tccgacggct ccttcttcct ctacagcaag   1080
ctcaccgtgg acaagagcag gtggcagcag gggaacgtct tctcatgctc cgtgatgcat   1140
gaggctctgc acaaccacta cacgcagaag agcctctccc tgtctccggg taaa         1194
```

<210> SEQ ID NO 39
<211> LENGTH: 1347
<212> TYPE: DNA
<213> ORGANISM: Artificial Sequence
<220> FEATURE:
<223> OTHER INFORMATION: Synthetic

<400> SEQUENCE: 39

```
atgggtcggg ggctgctcag gggcctgtgg ccgctgcaca tcgtcctgtg gacgcgtatc      60
gccagcacga tcccaccgca cgttcagaag tcggttaata cgacatgat agtcactgac     120 aacaacggtg cagtcaagtt tccacaactg tgtaaatttt gtgatgtgag attttccacc    180
tgtgacaacc agaaatcctg catgagcaac tgcagcatca cctccatctg tgagaagcca    240
caggaagtct gtgtggctgt atggagaaag aatgacgaga acataacact agagacagtt    300
tgccatgacc ccaagctccc ctaccatgac tttattctgg aagatgctgc ttctccaaag    360
tgcattatga aggaaaaaaa aaagcctggt gagactttct tcatgtgttc ctgtagctct    420
gatgagtgca atgacaacat catcttctca gaagaatata acaccagcaa tcctgacaag    480
cccagcaaca ccaaggtgga caagagagtt gagctcaaaa ccccacttgg tgacacaact    540
cacacatgcc cacggtgccc agagcccaaa tcttgtgaca cacctccccc gtgcccacgg    600
tgcccagagc ccaaatcttg tgacacacct ccccatgcc cacggtgccc agagcccaaa    660
tcttgtgaca cacctccccc gtgcccaagg tgcccagcac ctgaactcct gggaggaccg    720
tcagtcttcc tcttcccccc aaaacccaag gataccctta tgatttcccg gacccctgag    780
gtcacgtgcg tggtggtgga cgtgagccac gaagaccccg aggtccagtt caagtggtac    840
gtggacggcg tggaggtgca taatgccaag acaaagccgc gggaggagca gtacaacagc    900
acgttccgtg tggtcagcgt cctcaccgtc ctgcaccagg actggctgaa cggcaaggag    960
tacaagtgca aggtctccaa caaagccctc ccagccccca tcgagaaaac catctccaaa   1020
accaaaggac agccccgaga accacaggtg tacaccctgc cccatcccg ggaggagatg    1080 accaagaacc aggtcagcct gacctgcctg gtcaaaggct tctacccag cgacatcgcc    1140 gtggagtggg agagcagcgg gcagccggag aacaactaca acaccacgcc tcccatgctg    1200
gactccgacg gctccttctt cctctacagc aagctcaccg tggacaagag caggtggcag   1260
```

| | |
|---|---|
| caggggaaca tcttctcatg ctccgtgatg catgaggctc tgcacaaccg cttcacgcag | 1320 |
| aagagcctct ccctgtctcc gggtaaa | 1347 |

<210> SEQ ID NO 40
<211> LENGTH: 1197
<212> TYPE: DNA
<213> ORGANISM: Artificial Sequence
<220> FEATURE:
<223> OTHER INFORMATION: Synthetic

<400> SEQUENCE: 40

| | |
|---|---|
| atgggtcggg ggctgctcag gggcctgtgg ccgctgcaca tcgtcctgtg gacgcgtatc | 60 |
| gccagcacga tcccaccgca cgttcagaag tcggttaata acgacatgat agtcactgac | 120 |
| aacaacggtg cagtcaagtt tccacaactg tgtaaatttt gtgatgtgag attttccacc | 180 |
| tgtgacaacc agaaatcctg catgagcaac tgcagcatca cctccatctg tgagaagcca | 240 |
| caggaagtct gtgtggctgt atggagaaag aatgacgaga acataacact agagacagtt | 300 |
| tgccatgacc ccaagctccc ctaccatgac tttattctgg aagatgctgc ttctccaaag | 360 |
| tgcattatga aggaaaaaaa aaagcctggt gagactttct tcatgtgttc ctgtagctct | 420 |
| gatgagtgca atgacaacat catcttctca gaagaatata acaccagcaa tcctgacaag | 480 |
| cccagcaaca ccaaggtgga caagagagtt gagtccaaat atggtccccc atgcccatca | 540 |
| tgcccagcac ctgagttcct gggggggacca tcagtcttcc tgttcccccc aaaacccaag | 600 |
| gacactctca tgatctcccg gacccctgag gtcacgtgcg tggtggtgga cgtgagccag | 660 |
| gaagaccccg aggtccagtt caactggtac gtggatggcg tggaggtgca taatgccaag | 720 |
| acaaagccgc gggaggagca gttcaacagc acgtaccgtg tggtcagcgt cctcaccgtc | 780 |
| ctgcaccagg actggctgaa cggcaaggag tacaagtgca aggtctccaa caaaggcctc | 840 |
| ccgtcctcca tcgagaaaac catctccaaa gccaaagggc agccccgaga gccacaggtg | 900 |
| tacaccctgc ccccatccca ggaggagatg accaagaacc aggtcagcct gacctgcctg | 960 |
| gtcaaaggct tctaccccag cgacatcgcc gtggagtggg agagcaatgg gcagccggag | 1020 |
| aacaactaca agaccacgcc tcccgtgctg gactccgacg gctccttctt cctctacagc | 1080 |
| aggctaaccg tggacaagag caggtggcag gaggggaatg tcttctcatg ctccgtgatg | 1140 |
| catgaggctc tgcacaacca ctacacacag aagagcctct ccctgtctct gggtaaa | 1197 |

<210> SEQ ID NO 41
<211> LENGTH: 1278
<212> TYPE: DNA
<213> ORGANISM: Artificial Sequence
<220> FEATURE:
<223> OTHER INFORMATION: Synthetic

<400> SEQUENCE: 41

| | |
|---|---|
| atgggtcggg ggctgctcag gggcctgtgg ccgctgcaca tcgtcctgtg gacgcgtatc | 60 |
| gccagcacga tcccaccgca cgttcagaag tcggttaata acgacatgat agtcactgac | 120 |
| aacaacggtg cagtcaagtt tccacaactg tgtaaatttt gtgatgtgag attttccacc | 180 |
| tgtgacaacc agaaatcctg catgagcaac tgcagcatca cctccatctg tgagaagcca | 240 |
| caggaagtct gtgtggctgt atggagaaag aatgacgaga acataacact agagacagtt | 300 |
| tgccatgacc ccaagctccc ctaccatgac tttattctgg aagatgctgc ttctccaaag | 360 |
| tgcattatga aggaaaaaaa aaagcctggt gagactttct tcatgtgttc ctgtagctct | 420 |

```
gatgagtgca atgacaacat catcttctca aagaatata  acaccagcaa tcctgacgtg    480
aagcactaca cgaatcccag ccaggatgtg actgtgccct gcccagttcc ctcaactcca    540
cctaccccat ctccctcaac tccacctacc ccatctccct catgctgcca ccccgactg     600 tcactgcacc gaccggccct cgaggacctg ctcttaggtt cagaagcgaa cctcacgtgc    660
acactgaccg gcctgagaga tgcctcaggt gtcaccttca cctggacgcc ctcaagtggg    720
aagagcgctg ttcaaggacc acctgagcgt gacctctgtg gctgctacag cgtgtccagt    780
gtcctgccgg gctgtgccga gccatggaac catgggaaga ccttcacttg cactgctgcc    840
taccccgagt ccaagacccc gctaaccgcc accctctcaa aatccggaaa acattccgg     900 cccgaggtcc acctgctgcc gccgccgtcg gaggagctgg ccctgaacga gctggtgacg    960
ctgacgtgcc tggcacgtgg cttcagcccc aaggatgtgc tggttcgctg gctgcagggg   1020
tcacaggagc tgccccgcga aagtacctg  acttgggcat cccggcagga gcccagccag   1080
ggcaccacca ccttcgctgt gaccagcata ctgcgcgtgg cagccgagga ctggaagaag   1140
ggggacacct tctcctgcat ggtgggccac gaggccctgc cgctggcctt cacacagaag   1200
accatcgacc gcttggcggg taaacccacc catgtcaatg tgtctgttgt catggcggag   1260
gtggacggca cctgctac                                                 1278

<210> SEQ ID NO 42
<211> LENGTH: 1239
<212> TYPE: DNA
<213> ORGANISM: Artificial Sequence
<220> FEATURE:
<223> OTHER INFORMATION: Synthetic

<400> SEQUENCE: 42
atgggtcggg ggctgctcag gggcctgtgg ccgctgcaca tcgtcctgtg gacgcgtatc     60
gccagcacga tcccaccgca cgttcagaag tcggttaata cgacatgat  agtcactgac    120 aacaacggtg cagtcaagtt tccacaactg tgtaaatttt gtgatgtgag attttccacc    180
tgtgacaacc agaaatcctg catgagcaac tgcagcatca cctccatctg tgagaagcca    240
caggaagtct gtgtggctgt atggagaaag aatgacgaga acataacact agagacagtt    300
tgccatgacc ccaagctccc ctaccatgac tttattctgg aagatgctgc ttctccaaag    360
tgcattatga aggaaaaaaa aaagcctggt gagactttct tcatgtgttc ctgtagctct    420
gatgagtgca atgacaacat catcttctca aagaatata  acaccagcaa tcctgacgtg    480
aagcactaca cgaatcccag ccaggatgtg actgtgccct gcccagttcc cccacctccc    540
ccatgctgcc accccgact  gtcgctgcac cgaccggccc tcgaggacct gctcttaggt    600
tcagaagcga acctcacgtg cacactgacc ggcctgagag atgcctctgg tgccaccttc    660
acctggacgc cctcaagtgg gaagagcgct gttcaaggac cacctgagcg tgacctctgt    720
ggctgctaca gcgtgtccag tgtcctgcct ggctgtgccc agccatggaa ccatggggag    780
accttcacct gcactgctgc ccaccccgag ttgaagaccc actaaccgc  caacatcaca    840 aaatccggaa acacattccg gcccgaggtc cacctgctgc cgccgccgtc ggaggagctg    900
gccctgaacg agctggtgac gctgacgtgc ctggcacgtg gcttcagccc caaggatgtg    960
ctggttcgct ggctgcaggg gtcacaggag ctgccccgcg agaagtacct gacttgggca   1020
tcccggcagg agcccagcca gggcaccacc accttcgctg tgaccagcat actgcgcgtg   1080
gcagccgagg actggaagaa gggggacacc ttctcctgca tggtgggcca cgaggccctg   1140
ccgctggcct tcacacagaa gaccatcgac cgcatggcgg gtaaacccac ccatgtcaat   1200
```

```
gtgtctgttg tcatggcgga ggtggacggc acctgctac                           1239
```

<210> SEQ ID NO 43
<211> LENGTH: 1365
<212> TYPE: DNA
<213> ORGANISM: Artificial Sequence
<220> FEATURE:
<223> OTHER INFORMATION: Synthetic

<400> SEQUENCE: 43

```
atgggtcggg ggctgctcag gggcctgtgg ccgctgcaca tcgtcctgtg gacgcgtatc     60
gccagcacga tcccaccgca cgttcagaag tcggttaata cgacatgat  agtcactgac    120
aacaacggtg cagtcaagtt tccacaactg tgtaaatttt gtgatgtgag attttccacc    180
tgtgacaacc agaaatcctg catgagcaac tgcagcatca cctccatctg tgagaagcca    240
caggaagtct gtgtggctgt atggagaaag aatgacgaga acataacact agagacagtt    300
tgccatgacc ccaagctccc ctaccatgac tttattctgg aagatgctgc ttctccaaag    360
tgcattatga aggaaaaaaa aaagcctggt gagactttct tcatgtgttc ctgtagctct    420
gatgagtgca atgacaacat catcttctca gaagaatata acaccagcaa tcctgacacc    480
gccagcaaga gtaagaagga gatcttccgc tggccagagt ctccaaaggc acaggcctcc    540
tcagtgccca ctgcacaacc ccaagcgagg ggcagcctcg ccaaggcaac cacagcccca    600
gccaccaccc gtaacacagg aaggaggagga gaagagaaga gaaggagaa ggagaaagag    660
gaacaagaag agagagagac aaagacacca gagtgtccga ccacacccca gcctcttggc    720
gtctacctgc taaccctgc agtgcaggac ctgtggctcc gggacaaagc caccttcacc    780
tgcttcgtgg tgggcagtga cctgaaggat gctcacctga cctggaggt  ggccgggaag    840
gtccccacag ggggcgtgga ggaagggctg ctggagcggc acagcaacgg ctcccagagc    900
cagcacagcc gtctgacccT gcccaggtcc ttgtggaacg cggggacctc cgtcacctgc    960
acactgaacc atcccagcct cccaccccag aggttgatgg cgctgagaga cccgctgcg    1020
caggcacccg tcaagctttc cctgaacctg ctggcctcgt ctgaccctcc cgaggcggcc   1080
tcgtggctcc tgtgtgaggt gtctggcttc tcgcccccca acatcctcct gatgtggctg   1140
gaggaccagc gtgaggtgaa cacttctggg tttgcccccg cacgcccccc tccacagccc   1200
gggagcacca cgttctgggc ctggagtgtg ctgcgtgtcc cagccccgcc cagccctcag   1260
ccagccacct acacgtgtgt ggtcagccac gaggactccc ggactctgct caacgccagc   1320
cggagcctag aagtcagcta tgtaacagac catggcccca tgaaa                  1365
```

<210> SEQ ID NO 44
<211> LENGTH: 1494
<212> TYPE: DNA
<213> ORGANISM: Artificial Sequence
<220> FEATURE:
<223> OTHER INFORMATION: Synthetic

<400> SEQUENCE: 44

```
atgggtcggg ggctgctcag gggcctgtgg ccgctgcaca tcgtcctgtg gacgcgtatc     60
gccagcacga tcccaccgca cgttcagaag tcggttaata cgacatgat  agtcactgac    120
aacaacggtg cagtcaagtt tccacaactg tgtaaatttt gtgatgtgag attttccacc    180
tgtgacaacc agaaatcctg catgagcaac tgcagcatca cctccatctg tgagaagcca    240
caggaagtct gtgtggctgt atggagaaag aatgacgaga acataacact agagacagtt    300
```

```
tgccatgacc ccaagctccc ctaccatgac tttattctgg aagatgctgc ttctccaaag      360
tgcattatga aggaaaaaaa aaagcctggt gagactttct tcatgtgttc ctgtagctct      420
gatgagtgca atgacaacat catcttctca gaagaatata acaccagcaa tcctgacact      480
ccatcgtcca cagactgggt cgacaacaaa accttcagcg tctgctccag ggacttcacc      540
ccgcccaccg tgaagatctt acagtcgtcc tgcgacggcg gcgggcactt cccccgacc      600 atccagctcc tgtgcctcgt ctctgggtac accccaggga ctatcaacat cacctggctg      660
gaggacgggc aggtcatgga cgtggacttg tccaccgcct ctaccacgca ggagggtgag      720
ctggcctcca cacaaagcga gctcaccctc agccagaagc actggctgtc agaccgcacc      780
tacacctgcc aggtcaccta tcaaggtcac acctttgagg acagcaccaa gaagtgtgca      840
gattccaacc cgagaggggt gagcgcctac ctaagccggc ccagcccgtt cgacctgttc      900
atccgcaagt cgcccacgat cacctgtctg gtggtggacc tggcacccag caaggggacc      960
gtgaacctga cctggtcccg ggccagtggg aagcctgtga accactccac cagaaaggag     1020
gagaagcagc gcaatggcac gttaaccgtc acgtccaccc tgccggtggg cacccgagac     1080
tggatcgagg gggagaccta ccagtgcagg gtgacccacc cccacctgcc caggccctc      1140 atgcggtcca cgaccaagac cagcggcccg cgtgctgccc cggaagtcta tgcgtttgcg     1200
acgccggagt ggccgggag ccgggacaag cgcaccctcg cctgcctgat ccagaacttc     1260
atgcctgagg acatctcggt gcagtggctg cacaacgagg tgcagctccc ggacgccgg      1320 cacagcacga cgcagccccg caagaccaag ggctccggct tcttcgtctt cagccgcctg     1380
gaggtgacca gggccgaatg ggagcagaaa atgagttca tctgccgtgc agtccatgag      1440
gcagcgagcc cctcacagac cgtccagcga gcggtgtctg taaatcccgg taaa           1494

<210> SEQ ID NO 45
<211> LENGTH: 1569
<212> TYPE: DNA
<213> ORGANISM: Artificial Sequence
<220> FEATURE:
<223> OTHER INFORMATION: Synthetic

<400> SEQUENCE: 45
atgggtcggg ggctgctcag gggcctgtgg ccgctgcaca tcgtcctgtg gacgcgtatc        60
gccagcacga tcccaccgca cgttcagaag tcggttaata cgacatgat agtcactgac       120 aacaacggtg cagtcaagtt tccacaactg tgtaaatttt gtgatgtgag attttccacc       180
tgtgacaacc agaaatcctg catgagcaac tgcagcatca cctccatctg tgagaagcca       240
caggaagtct gtgtggctgt atggagaaag aatgacgaga acataacact agagacagtt       300
tgccatgacc ccaagctccc ctaccatgac tttattctgg aagatgctgc ttctccaaag       360
tgcattatga aggaaaaaaa aaagcctggt gagactttct tcatgtgttc ctgtagctct       420
gatgagtgca atgacaacat catcttctca gaagaatata acaccagcaa tcctgacgtc       480
cagcacccca acggcaacaa agaaaagaac gtgcctcttc cagtgattgc tgagctgcct       540
cccaaagtga gcgtcttcgt cccacccgc gacggcttct cggcaacccc cgcaagtcc        600 aagctcatct gccaggccac gggtttcagt ccccggcaga ttcaggtgtc ctggctgcgc       660
gaggggaagc aggtggggtc tggcgtcacc acggaccagg tgcaggctga ggccaaagag       720
tctgggccca cgacctacaa ggtgaccagc acactgacca tcaaagagag cgactggctc       780
agccagagca tgttcacctg ccgcgtggat cacaggggcc tgaccttcca gcagaatgcg       840
tcctccatgt gtgtccccga tcaagacaca gccatccggg tcttcgccat cccccccatcc     900
```

```
tttgccagca tcttcctcac caagtccacc aagttgacct gcctggtcac agacctgacc    960
acctatgaca gcgtgaccat ctcctggacc cgccagaatg gcgaagctgt gaaaacccac   1020
accaacatct ccgagagcca ccccaatgcc actttcagcg ccgtgggtga ggccagcatc   1080
tgcgaggatg actggaattc cggggagagg ttcacgtgca ccgtgaccca cacagacctg   1140
ccctcgccac tgaagcagac catctcccgg cccaagggg tggccctgca caggcccgat    1200
gtctacttgc tgccaccagc ccgggagcag ctgaacctgc gggagtcggc caccatcacg   1260
tgcctggtga cgggcttctc tcccgcggac gtcttcgtgc agtggatgca gagggggcag   1320
cccttgtccc cggagaagta tgtgaccagc gccccaatgc ctgagcccca ggccccaggc   1380
cggtacttcg cccacagcat cctgaccgtg tccgaagagg aatggaacac gggggagacc   1440
tacacctgcg tggtggccca tgaggccctg cccaacaggg tcaccgagag gaccgtggac   1500
aagtccaccg gtaaacccac cctgtacaac gtgtccctgg tcatgtccga cacagctggc   1560
acctgctac                                                           1569

<210> SEQ ID NO 46
<211> LENGTH: 1206
<212> TYPE: DNA
<213> ORGANISM: Artificial Sequence
<220> FEATURE:
<223> OTHER INFORMATION: Synthetic

<400> SEQUENCE: 46
atgggtcggg ggctgctcag ggcctgtgg ccgctgcaca tcgtcctgtg gacgcgtatc      60
gccagcacga tcccaccgca cgttcagaag tcggttaata cgacatgat agtcactgac    120 aacaacggtg cagtcaagtt tccacaactg tgtaaatttt gtgatgtgag attttccacc    180
tgtgacaacc agaaatcctg catgagcaac tgcagcatca cctccatctg tgagaagcca    240
caggaagtct gtgtggctgt atggagaaag aatgacgaga acataacact agagacagtt    300
tgccatgacc ccaagctccc ctaccatgac tttattctgg aagatgctgc ttctccaaag    360
tgcattatga aggaaaaaaa aaagcctggt gagactttct tcatgtgttc ctgtagctct    420
gatgagtgca atgacaacat catcttctca gaagaatata acaccagcaa tcctgactac    480
gttcccaaag agtttaatgc tgaaacattc accccaaat cttgtgacaa aactcacaca    540
tgcccaccgt gcccagcacc tgaactcctg ggggaccgt cagtcttcct cttcccccca    600
aaacccaagg acaccctcat gatctcccgg acccctgagg tcacatgcgt ggtggtggac    660
gtgagccacg aagaccctga ggtcaagttc aactggtacg tggacggcgt ggaggtgcat    720
aatgccaaga caaagccgcg ggaggagcag tacaacagca cgtaccgtgt ggtcagcgtc    780
ctcaccgtcc tgcaccagga ctggctgaat ggcaaggagt acaagtgcaa ggtctccaac    840
aaagccctcc cagcccccat cgagaaaacc atctccaaag ccaaagggca gccccgagaa    900
ccacaggtgt acaccctgcc cccatcccgg gatgagctga ccaagaacca ggtcagcctg    960
acctgcctgg tcaaaggctt ctatcccagc gacatcgccg tggagtggga gagcaatggg   1020
cagccggaga caactacaa gaccacgcct cccgtgctgg actccgacgg ctccttcttc    1080
ctctacagca agctcaccgt ggacaagagc aggtggcagc aggggaacgt cttctcatgc   1140
tccgtgatgc atgaggctct gcacaaccac tacacgcaga agagcctctc cctgtctccg   1200
ggtaaa                                                              1206

<210> SEQ ID NO 47
```

<211> LENGTH: 1206
<212> TYPE: DNA
<213> ORGANISM: Artificial Sequence
<220> FEATURE:
<223> OTHER INFORMATION: Synthetic

<400> SEQUENCE: 47

```
atgggtcggg ggctgctcag gggcctgtgg ccgctgcaca tcgtcctgtg gacgcgtatc      60
gccagcacga tcccaccgca cgttcagaag tcggttaata cgacatgat agtcactgac     120
aacaacggtg cagtcaagtt tccacaactg tgtaaatttt gtgatgtgag attttccacc     180
tgtgacaacc agaaatcctg catgagcaac tgcagcatca cctccatctg tgagaagcca     240
caggaagtct gtgtggctgt atggagaaag aatgacgaga cataacact agagacagtt      300
tgccatgacc ccaagctccc ctaccatgac tttattctgg aagatgctgc ttctccaaag     360
tgcattatga aggaaaaaaa aaagcctggt gagactttct tcatgtgttc ctgtagctct     420
gatgagtgca atgacaacat catcttctca gaagaatata acaccagcaa tcctgacaga     480
gaaaaacaga ctgatgaaat caaggatact aggcccaaat cttgtgacaa aactcacaca     540
tgcccaccgt gcccagcacc tgaactcctg ggggaccgt cagtcttcct cttccccca      600
aaacccaagg acaccctcat gatctcccgg acccctgagg tcacatgcgt ggtggtggac     660
gtgagccacg aagaccctga ggtcaagttc aactggtacg tggacggcgt ggaggtgcat     720
aatgccaaga caaagccgcg ggaggagcag tacaacagca cgtaccgtgt ggtcagcgtc     780
ctcaccgtcc tgcaccagga ctggctgaat ggcaaggagt acaagtgcaa ggtctccaac     840
aaagccctcc cagcccccat cgagaaaacc atctccaaag ccaaagggca gccccgagaa     900
ccacaggtgt acaccctgcc cccatcccgg gatgagctga ccaagaacca ggtcagcctg     960
acctgcctgg tcaaaggctt ctatcccagc gacatcgccg tggagtggga gagcaatggg    1020
cagccggaga acaactacaa gaccacgcct cccgtgctgg actccgacgg ctccttcttc    1080
ctctacagca agctcaccgt ggacaagagc aggtggcagc aggggaacgt cttctcatgc    1140
tccgtgatgc atgaggctct gcacaaccac tacacgcaga gagcctctc cctgtctccg     1200
ggtaaa                                                              1206
```

<210> SEQ ID NO 48
<211> LENGTH: 390
<212> TYPE: PRT
<213> ORGANISM: Artificial Sequence
<220> FEATURE:
<223> OTHER INFORMATION: Synthetic

<400> SEQUENCE: 48

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
```

```
            100                 105                 110
Leu Glu Asp Ala Ala Ser Pro Lys Cys Ile Met Lys Glu Lys Lys
            115                 120                 125

Pro Gly Glu Thr Phe Phe Met Cys Ser Cys Ser Ser Asp Glu Cys Asn
            130                 135                 140

Asp Asn Ile Ile Phe Ser Glu Glu Tyr Asn Thr Ser Asn Pro Asp Pro
145                 150                 155                 160

Lys Ser Cys Asp Lys Thr His Thr Cys Pro Pro Cys Pro Ala Pro Glu
                165                 170                 175

Leu Leu Gly Gly Pro Ser Val Phe Leu Phe Pro Pro Lys Pro Lys Asp
                180                 185                 190

Thr Leu Met Ile Ser Arg Thr Pro Glu Val Thr Cys Val Val Val Asp
                195                 200                 205

Val Ser His Glu Asp Pro Glu Val Lys Phe Asn Trp Tyr Val Asp Gly
                210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
                260                 265                 270

Ala Pro Ile Glu Lys Thr Ile Ser Lys Ala Lys Gly Gln Pro Arg Glu
                275                 280                 285

Pro Gln Val Tyr Thr Leu Pro Pro Ser Arg Asp Glu Leu Thr Lys Asn
            290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
                340                 345                 350

Leu Thr Val Asp Lys Ser Arg Trp Gln Gln Gly Asn Val Phe Ser Cys
                355                 360                 365

Ser Val Met His Glu Ala Leu His Asn His Tyr Thr Gln Lys Ser Leu
                370                 375                 380

Ser Leu Ser Pro Gly Lys
385                 390

<210> SEQ ID NO 49
<211> LENGTH: 15
<212> TYPE: PRT
<213> ORGANISM: Artificial Sequence
<220> FEATURE:
<223> OTHER INFORMATION: Synthetic

<400> SEQUENCE: 49

Gly Gly Gly Gly Ser Gly Gly Gly Gly Ser Gly Gly Gly Gly Ser
1               5                   10                  15

<210> SEQ ID NO 50
<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: misc_feature
<222> LOCATION: (2)..(2)
```

```
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be Lys or Arg

<400> SEQUENCE: 50

Arg Xaa Xaa Arg
1

<210> SEQ ID NO 51
<211> LENGTH: 4
<212> TYPE: PRT
<213> ORGANISM: Artificial Sequence
<220> FEATURE:
<223> OTHER INFORMATION: Furin cleavage site

<400> SEQUENCE: 51

Arg Ala Lys Arg
1

<210> SEQ ID NO 52
<211> LENGTH: 35938
<212> TYPE: DNA
<213> ORGANISM: Adenovirus type 5

<400> SEQUENCE: 52
catcatcaat aatataccett attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg     180 gtgtgcgccg gtgtacacag gaagtgacaa ttttcgcgcg gttttaggcg gatgttgtag     240
taaatttggg cgtaaccgag taagatttgg ccatttccgc gggaaaactg aataagagga     300
agtgaaatct gaataatttt gtgttactca tagcgcgtaa tatttgtcta gggccgcggg     360
gactttgacc gtttacgtgg agactcgccc aggtgttttt ctcaggtgtt ttccgcgttc     420
cgggtcaaag ttggcgtttt attattatag tcagctgacg tgtagtgtat ttatacccgg     480
tgagttcctc aagaggccac tcttgagtgc cagcgagtag agttttctcc tccgagccgc     540
tccgacaccg ggactgaaaa tgagacatat tatctgccac ggaggtgtta ttaccgaaga     600
aatggccgcc agtcttttgg accagctgat cgaagaggta ctggctgata atcttccacc     660
tcctagccat tttgaaccac ctaccttca cgaactgtat gatttagacg tgacggcccc     720
cgaagatccc aacaggagg cggtttcgca gatttttccc gactctgtaa tgttggcggt     780
gcaggaaggg attgacttac tcacttttcc gccggcgccc ggttctccgg agccgcctca     840
cctttcccgg cagcccgagc agccggagca gagagcttg ggtccggttt ctatgccaaa     900
ccttgtaccg gaggtgatcg atcttacctg ccacgaggct ggctttccac ccagtgacga     960
cgaggatgaa gagggtgagg agtttgtgtt agattatgtg gagcaccccg ggcacggttg    1020
caggtcttgt cattatcacc ggaggaatac ggggaccca gatattatgt gttcgctttg    1080
ctatatgagg acctgtggca tgtttgtcta cagtaagtga aaattatggg cagtgggtga    1140
tagagtggtg ggtttggtgt ggtaattttt tttttaattt ttacagtttt gtggtttaaa    1200
gaattttgta ttgtgatttt tttaaaaggt cctgtgtctg aacctgagcc tgagcccgag    1260
ccagaaccgg agcctgcaag acctaccgc cgtcctaaaa tggcgcctgc tatcctgaga    1320
cgcccgacat cacctgtgtc tagagaatgc aatagtagta cggatagctg tgactccggt    1380
ccttctaaca cacctcctga gatacacccg gtggtcccgc tgtgccccat taaaccagtt    1440
```

```
gccgtgagag ttggtgggcg tcgccaggct gtggaatgta tcgaggactt gcttaacgag    1500
cctgggcaac ctttggactt gagctgtaaa cgccccaggc cataaggtgt aaacctgtga    1560
ttgcgtgtgt ggttaacgcc tttgtttgct gaatgagttg atgtaagttt aataaagggt    1620
gagataatgt ttaacttgca tggcgtgtta aatggggcgg ggcttaaagg gtatataatg    1680
cgccgtgggc taatcttggt tacatctgac ctcatggagg cttgggagtg tttggaagat    1740 tttctgctg tgcgtaactt gctggaacag agctctaaca gtacctcttg gttttggagg    1800
tttctgtggg gctcatccca ggcaaagtta gtctgcagaa ttaaggagga ttacaagtgg    1860
gaatttgaag agcttttgaa atcctgtggt gagctgtttg attctttgaa tctgggtcac    1920
caggcgcttt tccaagagaa ggtcatcaag actttggatt tttccacacc ggggcgcgct    1980
gcggctgctg ttgcttttttt gagttttata aaggataaat ggagcgaaga aacccatctg    2040
agcggggggt acctgctgga ttttctggcc atgcatctgt ggagagcggt tgtgagacac    2100
aagaatcgcc tgctactgtt gtcttccgtc cgcccggcga taataccgac ggaggagcag    2160
cagcagcagc aggaggaagc caggcggcgg cggcaggagc agagcccatg gaacccgaga    2220
gccggcctgg accctcggga atgaatgttg tacaggtggc tgaactgtat ccagaactga    2280
gacgcatttt gacaattaca gaggatgggc aggggctaaa gggggtaaag agggagcggg    2340
gggcttgtga ggctacagag gaggctagga atctagcttt tagcttaatg accagacacc    2400
gtcctgagtg tattacttttt caacagatca aggataattg cgctaatgag cttgatctgc    2460
tggcgcagaa gtattccata gagcagctga ccacttactg gctgcagcca ggggatgatt    2520
ttgaggaggc tattagggta tatgcaaagg tggcacttag gccagattgc aagtacaaga    2580
tcagcaaact tgtaaatatc aggaattgtt gctacatttc tgggaacggg gccgaggtgg    2640
agatagatac ggaggatagg gtggccttta gatgtagcat gataaatatg tggccggggg    2700
tgcttggcat ggacggggtg gttattatga atgtaaggtt tactggcccc aattttagcg    2760
gtacggtttt cctggccaat accaacctta tcctacacgg tgtaagcttc tatgggttta    2820
acaatacctg tgtggaagcc tggaccgatg taagggttcg gggctgtgcc ttttactgct    2880
gctggaaggg ggtggtgtgt cgccccaaaa gcagggcttc aattaagaaa tgcctctttg    2940
aaaggtgtac cttgggtatc ctgtctgagg gtaactccag ggtgcgccac aatgtggcct    3000
ccgactgtgg ttgcttcatg ctagtgaaaa gcgtggctgt gattaagcat aacatggtat    3060
gtggcaactg cgaggacagg gcctctcaga tgctgacctg ctcggacggc aactgtcacc    3120
tgctgaagac cattcacgta gccagccact ctcgcaaggc ctggccagtg tttgagcata    3180
acatactgac ccgctgttcc ttgcatttgg gtaacaggag ggggtgttc ctaccttacc    3240 aatgcaattt gagtcacact aagatattgc ttgagcccga gagcatgtcc aaggtgaacc    3300
tgaacggggt gtttgacatg accatgaaga tctggaaggt gctgaggtac gatgagaccc    3360
gcaccaggtg cagaccctgc gagtgtggcg gtaaacatat taggaaccag cctgtgatgc    3420
tggatgtgac cgaggagctg aggcccgatc acttggtgct ggcctgcacc cgcgctgagt    3480
ttggctctag cgatgaagat acagattgag gtactgaaat gtgtgggcgt ggcttaaggg    3540
tgggaaagaa tatataaggt gggggtctta tgtagttttg tatctgtttt gcagcagccg    3600
ccgccgccat gagcaccaac tcgtttgatg gaagcattgt gagctcatat ttgacaacgc    3660
gcatgccccc atgggccggg gtgcgtcaga atgtgatggg ctccagcatt gatggtcgcc    3720
ccgtcctgcc cgcaaactct actaccttga cctacgagac cgtgtctgga acgccgttgg    3780
```

```
agactgcagc ctccgccgcc gcttcagccg ctgcagccac cgcccgcggg attgtgactg   3840
actttgcttt cctgagcccg cttgcaagca gtgcagcttc ccgttcatcc gcccgcgatg   3900
acaagttgac ggctcttttg gcacaattgg attctttgac ccgggaactt aatgtcgttt   3960
ctcagcagct gttggatctg cgccagcagg tttctgccct gaaggcttcc tcccctccca   4020
atgcggttta aacataaat aaaaaaccag actctgtttg gatttggatc aagcaagtgt   4080
cttgctgtct ttatttaggg gttttgcgcg cgcggtaggc ccgggaccag cggtctcggt   4140
cgttgagggt cctgtgtatt ttttccagga cgtggtaaag gtgactctgg atgttcagat   4200
acatgggcat aagcccgtct ctggggtgga ggtagcacca ctgcagagct tcatgctgcg   4260
gggtggtgtt gtagatgatc cagtcgtagc aggagcgctg ggcgtggtgc ctaaaaatgt   4320
cttcagtag caagctgatt gccagggca ggcccttggt gtaagtgttt acaaagcggt   4380
taagctggga tgggtgcata cgtggggata tgagatgcat cttggactgt atttttaggt   4440
tggctatgtt cccagccata tccctccggg gattcatgtt gtgcagaacc accagcacag   4500
tgtatccggt gcacttggga aatttgtcat gtagcttaga aggaaatgcg tggaagaact   4560
tggagacgcc cttgtgacct ccaagatttt ccatgcattc gtccataatg atggcaatgg   4620
gcccacgggg ggcggcctgg gcgaagatat ttctgggatc actaacgtca tagttgtgtt   4680
ccaggatgag atcgtcatag gccattttta caaagcgcgg gcggagggtg ccagactgcg   4740
gtataatggt tccatccggc ccaggggcgt agttaccctc acagatttgc atttcccacg   4800
ctttgagttc agatgggggg atcatgtcta cctgcggggc gatgaagaaa acggtttccg   4860
gggtagggga gatcagctgg gaagaaagca ggttcctgag cagctgcgac ttaccgcagc   4920
cggtgggccc gtaaatcaca cctattaccg ggtgcaactg gtagttaaga gagctgcagc   4980
tgccgtcatc cctgagcagg ggggccactt cgttaagcat gtccctgact cgcatgtttt   5040
ccctgaccaa atccgccaga aggcgctcgc cgcccagcga tagcagttct tgcaaggaag   5100
caaagttttt caacggtttg agaccgtccg ccgtaggcat gcttttgagc gtttgaccaa   5160
gcagttccag gcggtcccac agctcggtca cctgctctac ggcatctcga tccagcatat   5220
ctcctcgttt cgcgggttgg ggcggctttc gctgtacggc agtagtcggt gctcgtccag   5280
acgggccagg gtcatgtctt tccacgggcg cagggtcctc gtcagcgtag tctgggtcac   5340
ggtgaagggg tgcgctccgg gctgcgcgct ggccagggtg cgcttgaggc tggtcctgct   5400
ggtgctgaag cgctgccggt cttcgccctg cgcgtcggcc aggtagcatt tgaccatggt   5460
gtcatagtcc agccctccg cggcgtggcc cttggcgcgc agcttgccct tggaggaggc   5520
gccgcacgag gggcagtgca gacttttgag ggcgtagagc ttgggcgcga gaaataccga   5580
ttccggggag taggcatccg cgccgcaggc cccgcagacg gtctcgcatt ccacgagcca   5640
ggtgagctct ggccgttcgg ggtcaaaaac caggtttccc ccatgctttt tgatgcgttt   5700
cttacctctg gtttccatga gccggtgtcc acgctcggtg acgaaaaggc tgtccgtgtc   5760
cccgtataca gacttgagag gcctgtcctc gagcggtgtt ccgcggtcct cctcgtatag   5820
aaactcggac cactctgaga caaaggctcg cgtccaggcc agcacgaagg aggctaagtg   5880
ggagggggtag cggtcgttgt ccactagggg gtccactcgc tccagggtgt gaagacacat   5940
gtcgccctct tcggcatcaa ggaaggtgat tggtttgtag gtgtaggcca cgtgaccggg   6000
tgttcctgaa gggggggctat aaaagggggt ggggcgcgt tcgtcctcac tctcttccgc   6060
atcgctgtct gcgagggcca gctgttgggg tgagtactcc ctctgaaaag cgggcatgac   6120
ttctgcgcta agattgtcag tttccaaaaa cgaggaggat ttgatattca cctggcccgc   6180
```

```
ggtgatgcct tgagggtgg ccgcatccat ctggtcagaa aagacaatct ttttgttgtc    6240
aagcttggtg gcaaacgacc cgtagagggc gttggacagc aacttggcga tggagcgcag    6300
ggtttggttt ttgtcgcgat cggcgcgctc cttggccgcg atgtttagct gcacgtattc    6360
gcgcgcaacg caccgccatt cgggaaagac ggtggtgcgc tcgtcgggca ccaggtgcac    6420
gcgccaaccg cggttgtgca gggtgacaag gtcaacgctg gtggctacct ctccgcgtag    6480
gcgctcgttg gtccagcaga ggcggccgcc cttgcgcgag cagaatggcg gtaggggtc    6540 tagctgcgtc tcgtccgggg ggtctgcgtc cacggtaaag accccgggca gcaggcgcgc    6600
gtcgaagtag tctatcttgc atccttgcaa gtctagcgcc tgctgccatg cgcgggcggc    6660
aagcgcgcgc tcgtatgggt tgagtggggg accccatggc atgggtgggg tgagcgcgga    6720
ggcgtacatg ccgcaaatgt cgtaaacgta gaggggctct ctgagtattc caagatatgt    6780
agggtagcat cttccaccgc ggatgctggc gcgcacgtaa tcgtatagtt cgtgcgaggg    6840
agcgaggagg tcgggaccga ggttgctacg ggcgggctgc tctgctcgga agactatctg    6900
cctgaagatg gcatgtgagt tggatgatat ggttggacgc tggaagacgt tgaagctggc    6960
gtctgtgaga cctaccgcgt cacgcacgaa ggaggcgtag gagtcgcgca gcttgttgac    7020
cagctcggcg gtgacctgca cgtctagggc gcagtagtcc agggtttcct tgatgatgtc    7080
atacttatcc tgtcccttttt ttttccacag ctcgcggttg aggacaaact cttcgcggtc    7140
tttccagtac tcttggatcg gaaacccgtc ggcctccgaa cggtaagagc ctagcatgta    7200
gaactggttg acggcctggt aggcgcagca tccctttttct acgggtagcg cgtatgcctg    7260
cgcggccttc cggagcgagg tgtgggtgag cgcaaaggtg tccctgacca tgactttgag    7320
gtactggtat ttgaagtcag tgtcgtcgca tccgccctgc tcccagagca aaaagtccgt    7380 gcgcttttg gaacgcggat ttggcagggc gaaggtgaca tcgttgaaga gtatctttcc    7440
cgcgcgaggc ataaagttgc gtgtgatgcg gaagggtccc ggcacctcgg aacggttgtt    7500
aattacctgg gcggcgagca cgatctcgtc aaagccgttg atgttgtggc ccacaatgta    7560
aagttccaag aagcgcggga tgcccttgat ggaaggcaat tttttaagtt cctcgtaggt    7620
gagctcttca ggggagctga gcccgtgctc tgaaagggcc cagtctgcaa gatgagggtt    7680
ggaagcgacg aatgagctcc acaggtcacg ggccattagc atttgcaggt ggtcgcgaaa    7740
ggtcctaaac tggcgaccta tggccatttt ttctggggtg atgcagtaga aggtaagcgg    7800
gtcttgttcc cagcggtccc atccaaggtt cgcggctagg tctcgcgcgg cagtcactag    7860
aggctcatct ccgccgaact tcatgaccag catgaagggc acgagctgct cccaaaggc    7920 ccccatccaa gtataggtct ctacatcgta ggtgacaaag agacgctcgg tgcgaggatg    7980
cgagccgatc gggaagaact ggatctcccg ccaccaattg gaggagtggc tattgatgtg    8040
gtgaaagtag aagtccctgc gacgggccga acactcgtgc tggctttttgt aaaaacgtgc    8100 gcagtactgg cagcggtgca cgggctgtac atcctgcacg aggttgacct gacgaccgcg    8160
cacaaggaag cagagtggga atttgagccc ctcgcctggc gggtttggct ggtggtcttc    8220
tacttcggct gcttgtcctt gaccgtctgg ctgctcgagg ggagttacgg tggatcggac    8280
caccacgccg cgcgagccca aagtccagat gtccgcgcgc ggcggtcgga gcttgatgac    8340
aacatcgcgc agatgggagc tgtccatggt ctggagctcc cgcggcgtca ggtcaggcgg    8400
gagctcctgc aggtttacct cgcatagacg ggtcagggcg cgggctagat ccaggtgata    8460
cctaatttcc aggggctggt tggtggcggc gtcgatggct tgcaagaggc cgcatccccg    8520
```

| | |
|---|---|
| cggcgcgact acggtaccgc gcggcgggcg gtgggccgcg ggggtgtcct tggatgatgc | 8580 |
| atctaaaagc ggtgacgcgg gcgagccccc ggaggtaggg ggggctccgg acccgccggg | 8640 |
| agaggggca ggggcacgtc ggcgccgcgc gcgggcagga gctggtgctg cgcgcgtagg | 8700 |
| ttgctggcga acgcgacgac gcggcggttg atctcctgaa tctggcgcct ctgcgtgaag | 8760 |
| acgacgggcc cggtgagctt gagcctgaaa gagagttcga cagaatcaat ttcggtgtcg | 8820 |
| ttgacgcgg cctggcgcaa aatctcctgc acgtctcctg agttgtcttg ataggcgatc | 8880 |
| tcggccatga actgctcgat ctcttcctcc tggagatctc cgcgtccggc tcgctccacg | 8940 |
| gtggcggcga ggtcgttgga aatgcggcc atgagctgcg agaaggcgtt gaggcctccc | 9000 |
| tcgttccaga cgcggctgta gaccacgccc ccttcggcat cgcgggcgcg catgaccacc | 9060 |
| tgcgcgagat tgagctccac gtgcggcgg aagacgcgt agtttcgcag gcgctgaaag | 9120 |
| aggtagttga gggtggtggc ggtgtgttct gccacgaaga agtacataac ccagcgtcgc | 9180 |
| aacgtggatt cgttgatatc ccccaaggcc tcaaggcgct ccatggcctc gtagaagtcc | 9240 |
| acggcgaagt tgaaaaactg ggagttgcgc gccgacacgg ttaactcctc ctccagaaga | 9300 |
| cggatgagct cggcgacagt gtcgcgcacc tcgcgctcaa aggctacagg ggcctcttct | 9360 |
| tcttcttcaa tctcctcttc cataaggggcc tcccttcctt cttcttctgg cggcggtggg | 9420 |
| ggaggggga cacggcggcg acgacggcg accgggaggc ggtcgacaaa gcgctcgatc | 9480 |
| atctccccgc ggcgacggcg catggtctcg gtgacggcgc ggccgttctc gcgggggcgc | 9540 |
| agttggaaga cgccgcccgt catgtcccgg ttatgggttg gcgggggct gccatgcggc | 9600 |
| agggatacgg cgctaacgat gcatctcaac aattgttgtg taggtactcc gccgccgagg | 9660 |
| gacctgagcg agtccgcatc gaccggatcg gaaaacctct cgagaaaggc gtctaaccag | 9720 |
| tcacagtcgc aaggtaggct gagcaccgtg gcgggcggca gcgggcggcg gtcggggttg | 9780 |
| tttctggcgg aggtgctgct gatgatgtaa ttaaagtagg cggtcttgag acggcggatg | 9840 |
| gtcgacagaa gcaccatgtc cttgggtccg gcctgctgaa tgcgcaggcg gtcggccatg | 9900 |
| ccccaggctt cgttttgaca tcggcgcagg tctttgtagt agtcttgcat gagcctttct | 9960 |
| accggcactt cttcttctcc ttcctcttgt cctgcatctc ttgcatctat cgctgcggcg | 10020 |
| gcggcggagt ttggccgtag gtggcgccct cttcctccca tgcgtgtgac cccgaagccc | 10080 |
| ctcatcggct gaagcagggc taggtcggcg acaacgcgct cggctaatat ggcctgctgc | 10140 |
| acctgcgtga gggtagactg gaagtcatcc atgtccacaa agcggtggta tgcgcccgtg | 10200 |
| ttgatggtgt aagtgcagtt ggccataacg gaccagttaa cggtctggtg acccggctgc | 10260 |
| gagagctcgg tgtacctgag acgcgagtaa gccctcgagt caaatacgta gtcgttgcaa | 10320 |
| gtccgcacca ggtactggta tcccaccaaa aagtgcggcg gcggctggcg gtagaggggc | 10380 |
| cagcgtaggg tggccggggc tccggggcg agatcttcca acataaggcg atgatatccg | 10440 |
| tagatgtacc tggacatcca ggtgatgccg cggcggtgg tggaggcgcg cggaaagtcg | 10500 |
| cggacgcggt tccagatgtt gcgcagcggc aaaaagtgct ccatggtcgg gacgctctgg | 10560 |
| ccggtcaggc gcgcgcaatc gttgacgctc tagaccgtgc aaaaggagag cctgtaagcg | 10620 |
| ggcactcttc cgtggtctgg tggataaatt cgcaagggta tcatggcgga cgaccggggt | 10680 |
| tcgagccccg tatccggccg tccgccgtga tccatgcggt taccgcccgc gtgtcgaacc | 10740 |
| caggtgtgcg acgtcagaca acgggggagt gctccttttg gcttccttcc aggcgcggcg | 10800 |
| gctgctgcgc tagcttttttt ggccactggc cgcgcgcagc gtaagcggtt aggctggaaa | 10860 |
| gcgaaagcat taagtggctc gctccctgta gccggagggt tattttccaa gggttgagtc | 10920 |

```
gcgggacccc cggttcgagt ctcggaccgg ccggactgcg gcgaacgggg gtttgcctcc    10980
ccgtcatgca agacccgct tgcaaattcc tccggaaaca gggacgagcc cctttttgc     11040
ttttcccaga tgcatccggt gctgcggcag atgcgccccc ctcctcagca gcggcaagag   11100
caagagcagc ggcagacatg cagggcaccc tccctcctc ctaccgcgtc aggaggggcg    11160
acatccgcgg ttgacgcggc agcagatggt gattacgaac cccgcggcg ccgggcccgg    11220
cactacctgg acttggagga gggcgagggc ctggcgcggc taggagcgcc ctctcctgag   11280
cggtacccaa gggtgcagct gaagcgtgat acgcgtgagg cgtacgtgcc gcggcagaac   11340
ctgtttcgcg accgcgaggg agaggagccc gaggagatgc gggatcgaaa gttccacgca   11400
gggcgcgagc tgcggcatgg cctgaatcgc gagcggttgc tgcgcgagga ggactttgag   11460
cccgacgcgc gaaccgggat tagtcccgcg cgcgcacacg tggcggccgc cgacctggta   11520
accgcatacg agcagacggt gaaccaggag attaactttc aaaaaagctt taacaaccac   11580
gtgcgtacgc ttgtggcgcg cgaggaggtg gctataggac tgatgcatct gtgggacttt   11640
gtaagcgcgc tggagcaaaa cccaaatagc aagccgctca tggcgcagct gttccttata   11700
gtgcagcaca gcagggacaa cgaggcattc agggatgcgc tgctaaacat agtagagccc   11760
gagggccgct ggctgctcga tttgataaac atcctgcaga gcatagtggt gcaggagcgc   11820
agcttgagcc tggctgacaa ggtggccgcc atcaactatt ccatgcttag cctgggcaag   11880
ttttacgccc gcaagatata ccatacccct tacgttccca tagacaagga ggtaaagatc   11940
gaggggttct acatgcgcat ggcgctgaag gtgcttacct tgagcgacga cctgggcgtt   12000
tatcgcaacg agcgcatcca caaggccgtg agcgtgagcc ggcggcgcga gctcagcgac   12060
cgcgagctga tgcacagcct gcaaagggcc ctggctggca cgggcagcgg cgatagagag   12120
gccgagtcct actttgacgc gggcgctgac ctgcgctggg ccccaagccg acgcgccctg   12180
gaggcagctg gggccggacc tgggctggcg gtggcacccg cgcgcgctgg caacgtcggc   12240
ggcgtggagg aatatgacga ggacgatgag tacgagccag aggacggcga gtactaagcg   12300
gtgatgtttc tgatcagatg atgcaagacg caacggaccc ggcggtgcgg gcggcgctgc   12360
agagccagcc gtccggcctt aactccacgg acgactggcg ccaggtcatg gaccgcatca   12420
tgtcgctgac tgcgcgcaat cctgacgcgt tccggcagca gccgcaggcc aaccggctct   12480
ccgcaattct ggaagcggtg gtcccggcgc gcgcaaaccc cacgcacgag aaggtgctgg   12540
cgatcgtaaa cgcgctggcc gaaaacaggg ccatccggcc cgacgaggcc ggcctggtct   12600
acgacgcgct gcttcagcgc gtggctcgtt acaacagcgg caacgtgcag accaacctgg   12660
accggctggt gggggatgtg cgcgaggccg tggcgcagcg tgagcgcgcg cagcagcagg   12720
gcaacctggg ctccatggtt gcactaaacg ccttcctgag tacacagccc gccaacgtgc   12780
cgcggggaca ggaggactac accaactttg tgagcgcact gcggctaatg gtgactgaga   12840
caccgcaaag tgaggtgtac cagtctgggc cagactattt tttccagacc agtagacaag   12900
gcctgcagac cgtaaacctg agccaggctt tcaaaaactt gcaggggctg tgggggtgc    12960
gggctcccac aggcgaccgc gcgaccgtgt ctagcttgct gacgcccaac tcgcgcctgt   13020
tgctgctgct aatagcgccc ttcacggaca gtggcagcgt gtcccgggac acatacctag   13080
gtcacttgct gacactgtac cgcgaggcca taggtcaggc gcatgtggac gagcatactt   13140
tccaggagat tacaagtgtc agccgcgcgc tggggcagga ggacacgggc agcctggagg   13200
caaccctaaa ctacctgctg accaaccggc ggcagaagat cccctcgttg cacagtttaa   13260
```

```
acagcgagga ggagcgcatt ttgcgctacg tgcagcagag cgtgagcctt aacctgatgc  13320 gcgacgggt aacgcccagc gtggcgctgg acatgaccgc gcgcaacatg gaaccgggca  13380
tgtatgcctc aaaccggccg tttatcaacc gcctaatgga ctacttgcat cgcgcggccg  13440
ccgtgaaccc cgagtatttc accaatgcca tcttgaaccc gcactggcta ccgcccctg  13500 gtttctacac cggggattc gaggtgcccg agggtaacga tggattcctc tgggacgaca  13560
tagacgacag cgtgttttcc ccgcaaccgc agaccctgct agagttgcaa cagcgcgagc  13620
aggcagaggc ggcgctgcga aaggaaagct tccgcaggcc aagcagcttg tccgatctag  13680
gcgctgcggc cccgcggtca gatgctagta gcccatttcc aagcttgata gggtctctta  13740
ccagcactcg caccacccgc ccgcgcctgc tgggcgagga ggagtaccta aacaactcgc  13800
tgctgcagcc gcagcgcgaa aaaaacctgc ctccggcatt tcccaacaac gggatagaga  13860
gcctagtgga caagatgagt agatggaaga cgtacgcgca ggagcacagg gacgtgccag  13920
gcccgcgccc gcccacccgt cgtcaaaggc acgaccgtca gcggggtctg tgtgggagg  13980 acgatgactc ggcagacgac agcagcgtcc tggatttggg agggagtggc aacccgtttg  14040
cgcaccttcg ccccaggctg gggagaatgt tttaaaaaaa aaaagcatg atgcaaaata  14100 aaaaactcac caaggccatg gcaccgagcg ttggttttct tgtattcccc ttagtatgcg  14160
gcgcgcggcg atgtatgagg aaggtcctcc tccctcctac gagagtgtgg tgagcgcggc  14220
gccagtggcg gcggcgctgg gttctccctt cgatgctccc ctggaccgc cgtttgtgcc  14280 tccgcggtac ctgcggccta ccggggggag aaacagcatc cgttactctg agttggcacc  14340
cctattcgac accaccgtg tgtacctggt ggacaacaag tcaacggatg tggcatccct  14400
gaactaccag aacgaccaca gcaactttct gaccacggtc attcaaaaca atgactacag  14460 cccggggggag gcaagcacac agaccatcaa tcttgacgac cggtcgcact ggggcggcga  14520
cctgaaaacc atcctgcata ccaacatgcc aaatgtgaac gagttcatgt ttaccaataa  14580
gtttaaggcg cgggtgatgg tgtcgcgctt gcctactaag gacaatcagg tggagctgaa  14640
atacgagtgg gtggagttca gctgcccga gggcaactac tccgagacca tgaccataga  14700
ccttatgaac aacgcgatcg tggagcacta cttgaaagtg gcagacaga acggggttct  14760 ggaaagcgac atcggggtaa agtttgacac ccgcaacttc agactggggt ttgaccccgt  14820
cactggtctt gtcatgcctg ggtatatac aaacgaagcc ttccatccag acatcatttt  14880
gctgccagga tgcggggtgg acttcaccca cagccgcctg agcaacttgt tgggcatccg  14940
caagcggcaa cccttccagg agggctttag gatcacctac gatgatctgg agggtggtaa  15000
cattcccgca ctgttggatg tggacgccta ccaggcgagc ttgaaagatg acaccgaaca  15060
gggcgggggt ggcgcaggcg gcagcaacag cagtggcagc ggcgcggaag agaactccaa  15120
cgcggcagcc gcggcaatgc agccggtgga ggacatgaac gatcatgcca ttcgcggcga  15180
cacctttgcc acacgggctg aggagaagcg cgctgaggcc gaagcagcgg ccgaagctgc  15240
cgcccccgct gcgcaacccg aggtcgagaa gcctcagaag aaaccggtga tcaaacccct  15300
gacagaggac agcaagaaac gcagttacaa cctaataagc aatgacagca ccttcacccca  15360 gtaccgcagc tggtaccttg catacaacta cggcgaccct cagaccggaa tccgctcatg  15420
gaccctgctt tgcactcctg acgtaacctg cggctcggag caggtctact ggtcgttgcc  15480
agacatgatg caagacccg tgaccttccg ctccacgcgc cagatcagca actttccggt  15540
ggtgggcgcc gagctgttgc ccgtgcactc caagagcttc tacaacgacc aggccgtcta  15600
ctcccaactc atccgccagt ttacctctct gacccacgtg ttcaatcgct ttcccgagaa  15660
```

-continued

```
ccagattttg gcgcgcccgc cagcccccac catcaccacc gtcagtgaaa acgttcctgc    15720
tctcacagat cacgggacgc taccgctgcg caacagcatc ggaggagtcc agcgagtgac    15780
cattactgac gccagacgcc gcacctgccc ctacgtttac aaggccctgg catagtctc    15840 gccgcgcgtc ctatcgagcc gcactttttg agcaagcatg tccatcctta tatcgcccag    15900
caataacaca ggctggggcc tgcgcttccc aagcaagatg tttggcgggg ccaagaagcg    15960
ctccgaccaa cacccagtgc gcgtgcgcgg gcactaccgc gcgccctggg gcgcgcacaa    16020
acgcggccgc actgggcgca ccaccgtcga tgacgccatc gacgcggtgg tggaggaggc    16080
gcgcaactac acgcccacgc cgccaccagt gtccacagtg gacgcggcca ttcagaccgt    16140
ggtgcgcgga gcccggcgct atgctaaaat gaagagacgg cggaggcgcg tagcacgtcg    16200
ccaccgccgc cgaccggca ctgccgccca acgcgcggcg gcggccctgc ttaaccgcgc    16260
acgtcgcacc ggccgacggg cggccatgcg ggccgctcga aggctggccg cgggtattgt    16320
cactgtgccc cccaggtcca ggcgacgagc ggccgccgca gcagccgcgg ccattagtgc    16380
tatgactcag ggtcgcaggg gcaacgtgta ttgggtgcgc gactcggtta gcggcctgcg    16440
cgtgcccgtg cgcacccgcc ccccgcgcaa ctagattgca agaaaaaact acttagactc    16500
gtactgttgt atgtatccag cggcggcggc gcgcaacgaa gctatgtcca agcgcaaaat    16560
caaagaagag atgctccagg tcatcgcgcc ggagatctat ggccccccga agaaggaaga    16620
gcaggattac aagcccgaa agctaaagcg ggtcaaaaag aaaagaaag atgatgatga    16680 tgaacttgac gacgaggtgg aactgctgca cgctaccgcg cccaggcgac gggtacagtg    16740
gaaaggtcga cgcgtaaaac gtgttttgcg acccggcacc accgtagtct ttacgcccgg    16800
tgagcgctcc acccgcacct acaagcgcgt gtatgatgag gtgtacggcg acgaggacct    16860
gcttgagcag gccaacgagc gcctcgggga gtttgcctac ggaaagcggc ataaggacat    16920
gctggcgttg ccgctggacg agggcaaccc aacacctagc ctaaagcccg taacactgca    16980
gcaggtgctg cccgcgcttg caccgtccga agaaaagcgc ggcctaaagc gcgagtctgg    17040
tgacttggca cccaccgtgc agctgatggt acccaagcgc cagcgactgg aagatgtctt    17100 ggaaaaatg accgtggaac ctgggctgga gcccgaggtc cgcgtgcggc caatcaagca    17160
ggtggcgccg ggactgggcg tgcagaccgt ggacgttcag atacccacta ccagtagcac    17220
cagtattgcc accgccacag agggcatgga gacacaaacg tccccggttg cctcagcggt    17280
ggcggatgcc gcggtgcagg cggtcgctgc ggccgcgtcc aagacctcta cggaggtgca    17340
aacgaccccg tggatgtttc gcgtttcagc ccccgcggc ccgcgcggtt cgaggaagta    17400
cggcgccgcc agcgcgctac tgcccgaata tgccctacat ccttccattg cgcctacccc    17460
cggctatcgt ggctacacct accgcccag aagacgagca actacccgac gccgaaccac    17520
cactggaacc cgccgccgcc gtcgccgtcg ccagcccgtg ctggccccga tttccgtgcg    17580
cagggtggct cgcgaaggag gcaggaccct ggtgctgcca acagcgcgct accacccag    17640 catcgtttaa aagccggtct ttgtggttct tgcagatatg gccctcacct gccgcctccg    17700
tttcccggtg ccgggattcc gaggaagaat gcaccgtagg aggggcatgg ccggccacgg    17760
cctgacgggc ggcatgcgtc gtgcgcacca ccggcggcgg cgcgcgtcgc accgtcgcat    17820
gcgcggcggt atcctgcccc tccttattcc actgatcgcc gcggcgattg gcgccgtgcc    17880
cggaattgca tccgtggcct tgcaggcgca gagacactga ttaaaaacaa gttgcatgtg    17940
gaaaaatcaa aataaaaagt ctggactctc acgctcgctt ggtcctgtaa ctattttgta    18000
```

```
gaatggaaga catcaacttt gcgtctctgg ccccgcgaca cggctcgcgc ccgttcatgg    18060
gaaactggca agatatcggc accagcaata tgagcggtgg cgccttcagc tggggctcgc    18120
tgtggagcgg cattaaaaat ttcggttcca ccgttaagaa ctatggcagc aaggcctgga    18180
acagcagcac aggccagatg ctgagggata agttgaaaga gcaaaatttc aacaaaagg     18240 tggtagatgg cctggcctct ggcattagcg gggtggtgga cctggccaac caggcagtgc    18300
aaaataagat taacagtaag cttgatcccc gccctcccgt agaggagcct ccaccggccg    18360
tggagacagt gtctccagag gggcgtggcg aaaagcgtcc gcgcccgac agggaagaaa     18420 ctctggtgac gcaaatagac gagcctccct cgtacgagga ggcactaaag caaggcctgc    18480
ccaccacccg tcccatcgcg cccatggcta ccggagtgct gggccagcac acaccgtaa     18540 cgctggacct gcctcccccc gccgacaccc agcagaaacc tgtgctgcca ggcccgaccg    18600
ccgttgttgt aacccgtcct agccgcgcgt ccctgcgccg cgccgccagc ggtccgcgat    18660
cgttgcggcc cgtagccagt ggcaactggc aaagcacact gaacagcatc gtgggtctgg    18720
gggtgcaatc cctgaagcgc cgacgatgct tctgaatagc taacgtgtcg tatgtgtgtc    18780
atgtatgcgt ccatgtcgcc ccagaggag ctgctgagcc gccgcgcgcc cgcttccaa      18840 gatggctacc ccttcgatga tgccgcagtg gtcttacatg cacatctcgg gccaggacgc    18900
ctcggagtac ctgagccccg ggctggtgca gtttgcccgc gccaccgaga cgtacttcag    18960
cctgaataac aagtttagaa accccacggt ggcgcctacg cacgacgtga ccacagaccg    19020
gtcccagcgt ttgacgctgc ggttcatccc tgtggaccgt gaggatactg cgtactcgta    19080
caaggcgcgg ttcaccctag ctgtgggtga taaccgtgtg ctggacatgg cttccacgta    19140
ctttgacatc cgcggcgtgc tggacagggg ccctactttt aagccctact ctggcactgc    19200
ctacaacgcc ctggctccca agggtgcccc aaatccttgc gaatgggatg aagctgctac    19260
tgctcttgaa ataaacctag aagaagagga cgatgacaac gaagacgaag tagacgagca    19320
agctgagcag caaaaaactc acgtatttgg gcaggcgcct tattctggta taaatattac    19380
aaaggagggt attcaaatag gtgtcgaagg tcaaacacct aaatatgccg ataaaacatt    19440
tcaacctgaa cctcaaatag gagaatctca gtggtacgaa actgaaatta atcatgcagc    19500
tgggagagtc cttaaaaaga ctaccccaat gaaaccatgt tacggttcat atgcaaaacc    19560
cacaaatgaa aatggagggc aaggcattct tgtaaagcaa caaatggaa agctagaaag      19620 tcaagtggaa atgcaatttt tctcaactac tgaggcgacc gcaggcaatg gtgataactt    19680
gactcctaaa gtggtattgt acagtgaaga tgtagatata gaaaccccag acactctat     19740 ttcttacatg cccactatta aggaaggtaa ctcacgagaa ctaatgggcc aacaatctat    19800
gcccaacagg cctaattaca ttgcttttag ggacaatttt attggtctaa tgtattacaa    19860
cagcacgggt aatatgggtg ttctggcggg ccaagcatcg cagttgaatg ctgttgtaga    19920
tttgcaagac agaaacacag agctttcata ccagcttttg cttgattcca ttggtgatag    19980
aaccaggtac ttttctatgt ggaatcaggc tgttgacagc tatgatccag atgttagaat    20040
tattgaaaat catggaactg aagatgaact tccaaattac tgctttccac tgggaggtgt    20100
gattaataca gagactctta ccaaggtaaa acctaaaaca ggtcaggaaa atggatggga    20160
aaaagatgct acagaatttt cagataaaaa tgaataaga gttggaaata ttttgccat      20220 ggaaatcaat ctaaatgcca acctgtggag aaatttcctg tactccaaca tagcgctgta    20280
tttgcccgac aagctaaagt acagtccttc caacgtaaaa atttctgata cccaaacac     20340 ctacgactac atgaacaagc gagtggtggc tcccggggtta gtggactgct acattaacct    20400
```

```
tggagcacgc tggtcccttg actatatgga caacgtcaac ccatttaacc accaccgcaa   20460
tgctggcctg cgctaccgct caatgttgct gggcaatggt cgctatgtgc ccttccacat   20520
ccaggtgcct cagaagttct ttgccattaa aaacctcctt ctcctgccgg gctcatacac   20580
ctacgagtgg aacttcagga aggatgttaa catggttctg cagagctccc taggaaatga   20640
cctaagggtt gacggagcca gcattaagtt tgatagcatt tgcctttacg ccaccttctt   20700
ccccatggcc cacaacaccg cctccacgct tgaggccatg cttagaaacg acaccaacga   20760
ccagtccttt aacgactatc tctccgccgc caacatgctc taccctatac ccgccaacgc   20820
taccaacgtg cccatatcca tccctcccg caactgggcg gctttccgcg gctgggcctt   20880
cacgcgcctt aagactaagg aaaccccatc actgggctcg ggctacgacc cttattacac   20940
ctactctggc tctatacct acctagatgg aaccttttac ctcaaccaca cctttaagaa   21000
ggtggccatt acctttgact cttctgtcag ctggcctggc aatgaccgcc tgcttacccc   21060
caacgagttt gaaattaagc gctcagttga cggggagggt tacaacgttg cccagtgtaa   21120
catgaccaaa gactggttcc tggtacaaat gctagctaac tacaacattg gctaccaggg   21180
cttctatatc ccagagagct acaaggaccg catgtactcc ttctttagaa acttccagcc   21240
catgagccgt caggtggtgg atgatactaa atacaaggac taccaacagg tgggcatcct   21300
acaccaacac aacaactctg gatttgttgg ctaccttgcc cccaccatgc gcgaaggaca   21360
ggcctaccct gctaacttcc cctatccgct tataggcaag accgcagttg acagcattac   21420
ccagaaaaag tttctttgcg atcgcaccct ttggcgcatc ccattctcca gtaactttat   21480
gtccatgggc gcactcacag acctgggcca aaaccttctc tacgccaact ccgcccacgc   21540
gctagacatg acttttgagg tggatcccat ggacgagccc acccttcttt atgttttgtt   21600
tgaagtcttt gacgtggtcc gtgtgcaccg gccgcaccgc ggcgtcatcg aaaccgtgta   21660
cctgcgcacg cccttctcgg ccggcaacgc cacaacataa agaagcaagc aacatcaaca   21720
acagctgccg ccatgggctc cagtgagcag gaactgaaag ccattgtcaa agatcttggt   21780
tgtgggccat attttttggg cacctatgac aagcgctttc caggctttgt ttctccacac   21840
aagctcgcct gcgccatagt caatacggcc ggtcgcgaga ctgggggcgt acactggatg   21900
gcctttgcct ggaacccgca ctcaaaaaca tgctacctct ttgagcccct tggcttttct   21960
gaccagcgac tcaagcaggt ttaccagttt gagtacgagt cactcctgcg ccgtagcgcc   22020
attgcttctt cccccgaccg ctgtataacg ctggaaaagt ccacccaaag cgtacagggg   22080
cccaactcgg ccgcctgtgg actattctgc tgcatgtttc tccacgcctt tgccaactgg   22140
ccccaaactc ccatggatca aaccccacc atgaacctta ttaccggggt acccaactcc   22200
atgctcaaca gtccccaggt acagcccacc ctgcgtcgca accaggaaca gctctacagc   22260
ttcctggagc gccactcgcc ctacttccgc agccacagtg cgcagattag gagcgccact   22320 tcttttgtc acttgaaaaa catgtaaaaa taatgtacta gagacacttt caataaaggc   22380
aaatgctttt atttgtacac tctcgggtga ttatttaccc ccacccttgc cgtctgcgcc   22440
gtttaaaaat caaggggtt ctgccgcgca tcgctatgcg ccactggcag ggacacgttg   22500
cgatactggt gtttagtgct ccacttaaac tcaggcacaa catccgcgg cagctcggtg   22560 aagttttcac tccacaggct gcgcaccatc accaacgcgt ttagcaggtc gggcgccgat   22620
atcttgaagt cgcagttggg gcctccgccc tgcgcgcgcg agttgcgata cacagggttg   22680
cagcactgga acactatcag cgccgggtgg tgcacgctgg ccagcacgct cttgtcggag   22740
```

-continued

| | |
|---|---|
| atcagatccg cgtccaggtc ctccgcgttg ctcagggcga acggagtcaa ctttggtagc | 22800 |
| tgccttccca aaaagggcgc gtgcccaggc tttgagttgc actcgcaccg tagtggcatc | 22860 |
| aaaaggtgac cgtgcccggt ctgggcgtta ggatacagcg cctgcataaa agccttgatc | 22920 |
| tgcttaaaag ccacctgagc ctttgcgcct tcagagaaga acatgccgca agacttgccg | 22980 |
| gaaaactgat tggccggaca ggccgcgtcg tgcacgcagc accttgcgtc ggtgttggag | 23040 |
| atctgcacca catttcggcc ccaccggttc ttcacgatct tggccttgct agactgctcc | 23100 |
| ttcagcgcgc gctgcccgtt ttcgctcgtc acatccattt caatcacgtg ctccttattt | 23160 |
| atcataatgc ttccgtgtag acacttaagc tcgccttcga tctcagcgca gcggtgcagc | 23220 |
| cacaacgcgc agcccgtggg ctcgtgatgc ttgtaggtca cctctgcaaa cgactgcagg | 23280 |
| tacgcctgca ggaatcgccc catcatcgtc acaaaggtct tgttgctggt gaaggtcagc | 23340 |
| tgcaacccgc ggtgctcctc gttcagccag gtcttgcata cggccgccag agcttccact | 23400 |
| tggtcaggca gtagtttgaa gttcgccttt agatcgttat ccacgtggta cttgtccatc | 23460 |
| agcgcgcgcg cagcctccat gcccttctcc cacgcagaca cgatcggcac actcagcggg | 23520 |
| ttcatcaccg taatttcact ttccgcttcg ctgggctctt cctcttcctc ttgcgtccgc | 23580 |
| ataccacgcg ccactgggtc gtcttcattc agccgccgca ctgtgcgctt acctcctttg | 23640 |
| ccatgcttga ttagcaccgg tgggttgctg aaacccacca tttgtagcgc acatcttct | 23700 |
| cttcttcct cgctgtccac gattacctct ggtgatggcg ggcgctcggg cttgggagaa | 23760 |
| gggcgcttct ttttcttctt gggcgcaatg gccaaatccg ccgccgaggt cgatggccgc | 23820 |
| gggctgggtg tgcgcggcac cagcgcgtct tgtgatgagt cttcctcgtc ctcggactcg | 23880 |
| atacgccgcc tcatccgctt ttttgggggc gcccggggag gcggcggcga cggggacggg | 23940 |
| gacgacacgt cctccatggt tggggacgt cgcgccgcac cgcgtccgcg ctcggggtg | 24000 |
| gtttcgcgct gctcctcttc ccgactggcc atttccttct cctataggca gaaaaagatc | 24060 |
| atggagtcag tcgagaagaa ggacagccta accgcccct ctgagttcgc caccaccgcc | 24120 |
| tccaccgatg ccgccaacgc gcctaccacc ttcccgtcg aggcacccc gcttgaggag | 24180 |
| gaggaagtga ttatcgagca ggacccaggt tttgtaagcg aagacgacga ggaccgctca | 24240 |
| gtaccaacag aggataaaaa gcaagaccag gacaacgcag aggcaaacga ggaacaagtc | 24300 |
| gggcggggg acgaaaggca tggcgactac ctagatgtgg gagacgacgt gctgttgaag | 24360 |
| catctgcagc gccagtgcgc cattatctgc gacgcgttgc aagagcgcag cgatgtgccc | 24420 |
| ctcgccatag cggatgtcag ccttgcctac gaacgccacc tattctcacc gcgcgtaccc | 24480 |
| cccaaacgcc aagaaaacgg cacatgcgag cccaacccgc gcctcaactt ctaccccgta | 24540 |
| tttgccgtgc cagaggtgct tgccacctat cacatctttt tccaaaactg caagataccc | 24600 |
| ctatcctgcc gtgccaaccg cagccgagcg gacaagcagc tggccttgcg gcagggcgct | 24660 |
| gtcatacctg atatcgcctc gctcaacgaa gtgccaaaaa tctttgaggg tcttggacgc | 24720 |
| gacgagaagc gcgcggcaaa cgctctgcaa caggaaaaca gcgaaaatga aagtcactct | 24780 |
| ggagtgttgg tggaactcga gggtgacaac gcgcgcctag ccgtactaaa acgcagcatc | 24840 |
| gaggtcaccc actttgccta cccggcactt aacctacccc caaggtcat gagcacagtc | 24900 |
| atgagtgagc tgatcgtgcg ccgtgcgcag cccctggaga gggatgcaaa tttgcaagaa | 24960 |
| caaacagagg agggcctacc cgcagttggc gacgagcagc tagcgcgctg gcttcaaacg | 25020 |
| cgcgagcctc ccgacttgga ggagcgcacg aaactaatga tggccgcagt gctcgttacc | 25080 |
| gtggagcttg agtgcatgca gcggttcttt gctgacccgg agatgcagcg caagctagag | 25140 |

```
gaaacattgc actacacctt tcgacagggc tacgtacgcc aggcctgcaa gatctccaac   25200
gtggagctct gcaacctggt ctcctacctt ggaattttgc acgaaaaccg ccttgggcaa   25260
aacgtgcttc attccacgct caagggcgag gcgcgccgcg actacgtccg cgactgcgtt   25320
tacttatttc tatgctacac ctggcagacg gccatgggcg tttggcagca gtgcttggag   25380
gagtgcaacc tcaaggagct gcagaaactg ctaaagcaaa acttgaagga cctatggacg   25440
gccttcaacg agcgctccgt ggccgcgcac ctggcggaca tcattttccc cgaacgcctg   25500
cttaaaaccc tgcaacaggg tctgccagac ttcaccagtc aaagcatgtt gcagaacttt   25560
aggaacttta tcctagagcg ctcaggaatc ttgcccgcca cctgctgtgc acttcctagc   25620
gactttgtgc ccattaagta ccgcgaatgc cctccgccgc tttggggcca ctgctacctt   25680
ctgcagctag ccaactacct tgcctaccac tctgacataa tggaagacgt gagcggtgac   25740
ggtctactgg agtgtcactg tcgctgcaac ctatgcaccc cgcaccgctc cctggtttgc   25800
aattcgcagc tgcttaacga aagtcaaatt atcggtacct ttgagctgca gggtccctcg   25860
cctgacgaaa agtccgcggc tccggggttg aaactcactc cggggctgtg gacgtcggct   25920
taccttcgca aatttgtacc tgaggactac cacgcccacg agattaggtt ctacgaagac   25980
caatcccgcc cgccaaatgc ggagcttacc gcctgcgtca ttacccaggg ccacattctt   26040
ggccaattgc aagccatcaa caaagcccgc caagagtttc tgctacgaaa gggacggggg   26100
gtttacttgg accccagtc cggcgaggag ctcaacccaa tccccccgcc gccgcagccc   26160
tatcagcagc agccgcgggc ccttgcttcc caggatggca cccaaaaaga agctgcagct   26220
gccgccgcca cccacggacg aggaggaata ctgggacagt caggcagagg aggttttgga   26280
cgaggaggag gaggacatga tggaagactg ggagagccta gacgaggaag cttccgaggt   26340
cgaagaggtg tcagacgaaa caccgtcacc ctcggtcgca ttccctcgc cggcgcccca    26400 gaaatcggca accggttcca gcatggctac aacctccgct cctcaggcgc cgccggcact   26460
gcccgttcgc cgacccaacc gtagatggga caccactgga accagggccg gtaagtccaa   26520
gcagccgccg ccgttagccc aagagcaaca acagcgccaa ggctaccgct catggcgcgg   26580
gcacaagaac gccatagttg cttgcttgca agactgtggg ggcaacatct ccttcgcccg   26640
ccgctttctt ctctaccatc acggcgtggc cttcccccgt aacatcctgc attactaccg   26700
tcatctctac agcccatact gcaccggcgg cagcggcagc ggcagcaaca gcagcggcca   26760
cacagaagca aaggcgaccg gatagcaaga ctctgacaaa gcccaagaaa tccacagcgg   26820
cggcagcagc aggaggagga gcgctgcgtc tggcgcccaa cgaacccgta tcgacccgcg   26880
agcttagaaa caggattttt cccactctgt atgctatatt tcaacagagc aggggccaag   26940
aacaagagct gaaaataaaa aacaggtctc tgcgatccct cacccgcagc tgcctgtatc   27000
acaaaagcga agatcagctt cggcgcacgc tggaagacgc ggaggctctc ttcagtaaat   27060
actgcgcgct gactcttaag gactagtttc gcgcccttc tcaaatttaa gcgcgaaaac   27120
tacgtcatct ccagcggcca cacccggcgc cagcacctgt cgtcagcgcc attatgagca   27180
aggaaattcc cacgccctac atgtggagtt accagccaca aatgggactt gcggctggag   27240
ctgcccaaga ctactcaacc cgaataaact acatgagcgc gggaccccac atgatatccc   27300
gggtcaacgg aatccgcgcc caccgaaacc gaattctctt ggaacaggcg gctattacca   27360
ccacacctcg taataacctt aatccccgta gttggcccgc tgcctggtg taccaggaaa    27420 gtcccgctcc caccactgtg gtacttccca gagacgccca ggccgaagtt cagatgacta   27480
```

-continued

```
actcaggggc gcagcttgcg ggcggctttc gtcacagggt gcggtcgccc gggcagggta   27540
taactcacct gacaatcaga gggcgaggta ttcagctcaa cgacgagtcg gtgagctcct   27600
cgcttggtct ccgtccggac gggacatttc agatcggcgg cgccggccgt ccttcattca   27660
cgcctcgtca ggcaatccta actctgcaga cctcgtcctc tgagccgcgc tctggaggca   27720
ttggaactct gcaatttatt gaggagtttg tgccatcggt ctactttaac cccttctcgg   27780
gacctcccgg ccactatccg gatcaattta ttcctaactt tgacgcggta aaggactcgg   27840
cggacggcta cgactgaatg ttaagtggag aggcagagca actgcgcctg aaacacctgg   27900
tccactgtcg ccgccacaag tgctttgccc gcgactccgg tgagttttgc tactttgaat   27960
tgcccgagga tcatatcgag ggcccggcgc acggcgtccg gcttaccgcc cagggagagc   28020
ttgcccgtag cctgattcgg gagtttaccc agcgccccct gctagttgag cgggacaggg   28080
gaccctgtgt tctcactgtg atttgcaact gtcctaacct tggattacat caagatcttt   28140
gttgccatct ctgtgctgag tataataaat acagaaatta aaatatactg gggctcctat   28200
cgccatcctg taaacgccac cgtcttcacc cgcccaagca accaaggcg aaccttacct   28260
ggtacttttta acatctctcc ctctgtgatt tacaacagtt tcaacccaga cggagtgagt   28320
ctacgagaga acctctccga gctcagctac tccatcagaa aaaacaccac cctccttacc   28380
tgccgggaac gtacgagtgc gtcaccggcc gctgcaccac acctaccgcc tgaccgtaaa   28440
ccagacttt tccggacaga cctcaataac tctgtttacc agaacaggag gtgagcttag   28500
aaaacccta gggtattagg ccaaaggcgc agctactgtg gggtttatga acaattcaag   28560
caactctacg ggctattcta attcaggttt ctctagaatc ggggttgggg ttattctctg   28620
tcttgtgatt ctctttattc ttatactaac gcttctctgc ctaaggctcg ccgcctgctg   28680
tgtgcacatt tgcatttatt gtcagctttt taaacgctgg ggtcgccacc caagatgatt   28740
aggtacataa tcctaggttt actcacccctt gcgtcagccc acggtaccac ccaaaaggtg   28800
gattttaagg agccagcctg taatgttaca ttcgcagctg aagctaatga gtgcaccact   28860
cttataaaat gcaccacaga acatgaaaag ctgcttattc gccacaaaaa caaaattggc   28920
aagtatgctg tttatgctat ttggcagcca ggtgacacta cagagtataa tgttacagtt   28980
ttccagggta aaagtcataa aacttttatg tatactttttc cattttatga aatgtgcgac   29040
attaccatgt acatgagcaa acagtataag ttgtggcccc cacaaaattg tgtggaaaac   29100
actggcactt tctgctgcac tgctatgcta attacagtgc tcgctttggt ctgtacccta   29160
ctctatatta aatacaaaag cagacgcagc tttattgagg aaaagaaaat gccttaattt   29220
actaagttac aaagctaatg tcaccactaa ctgctttact cgctgcttgc aaaacaaatt   29280
caaaaagtta gcattataat tagaatagga tttaaacccc ccggtcattt cctgctcaat   29340
accattcccc tgaacaattg actctatgtg ggatatgctc cagcgctaca accttgaagt   29400
caggcttcct ggatgtcagc atctgacttt ggccagcacc tgtccgcgg atttgttcca   29460
gtccaactac agcgacccac cctaacagag atgaccaaca caaccaacgc ggccgccgct   29520
accggactta catctaccac aaatacaccc caagtttctg cctttgtcaa taactgggat   29580
aacttgggca tgtggtggtt ctccatagcg cttatgtttg tatgccttat tattatgtgg   29640
ctcatctgct gcctaaagcg caaacgcgcc cgaccaccca tctatagtcc catcattgtg   29700
ctacacccaa acaatgatgg aatccataga ttggacggac tgaaacacat gttcttttct   29760
cttacagtat gattaaatga gacatgattc ctcgagtttt tatattactg acccttgttt   29820
cgcttttttg tgcgtgctcc acattggctg cggtttctca catcgaagta gactgcattc   29880
```

```
cagccttcac agtctatttg ctttacggat ttgtcaccct cacgctcatc tgcagcctca   29940
tcactgtggt catcgccttt atccagtgca ttgactgggt ctgtgtgcgc tttgcatatc   30000
tcagacacca tccccagtac agggacagga ctatagctga gcttcttaga attctttaat   30060
tatgaaattt actgtgactt ttctgctgat tatttgcacc ctatctgcgt tttgttcccc   30120
gacctccaag cctcaaagac atatatcatg cagattcact cgtatatgga atattccaag   30180
ttgctacaat gaaaaaagcg atctttccga agcctggtta tatgcaatca tctctgttat   30240
ggtgttctgc agtaccatct tagccctagc tatatatccc taccttgaca ttggctggaa   30300
acgaatagat gccatgaacc acccaacttt ccccgcgccc gctatgcttc cactgcaaca   30360
agttgttgcc ggcggctttg tcccagccaa tcagcctcgc cccacttctc ccaccccac    30420 tgaaatcagc tactttaatc taacaggagg agatgactga caccctagat ctagaaatgg   30480
acggaattat tacagagcag cgcctgctag aaagacgcag ggcagcggcc gagcaacagc   30540
gcatgaatca agagctccaa gacatggtta acttgcacca gtgcaaaagg ggtatctttt   30600
gtctggtaaa gcaggccaaa gtcacctacg acagtaatac caccggacac cgccttagct   30660
acaagttgcc aaccaagcgt cagaaattgg tggtcatggt gggagaaaag cccattacca   30720
taactcagca ctcggtagaa accgaaggct gcattcactc accttgtcaa ggacctgagg   30780
atctctgcac ccttattaag accctgtgcg gtctcaaaga tcttattccc tttaactaat   30840
aaaaaaaaat aataaagcat cacttactta aaatcagtta gcaaatttct gtccagttta   30900
ttcagcagca cctccttgcc ctcctcccag ctctggtatt gcagcttcct cctggctgca   30960
aactttctcc acaatctaaa tggaatgtca gtttcctcct gttcctgtcc atccgcaccc   31020
actatcttca tgttgttgca gatgaagcgc gcaagaccgt ctgaagatac cttcaacccc   31080
gtgtatccat atgacacgga aaccggtcct ccaactgtgc ctttcttac tcctcccttt    31140 gtatccccca atgggtttca agagagtccc cctggggtac tctctttgcg cctatccgaa   31200
cctctagtta cctccaatgg catgcttgcg ctcaaaatgg gcaacggcct ctctctggac   31260
gaggccggca accttacctc ccaaaatgta accactgtga gcccacctct caaaaaaacc   31320
aagtcaaaca taaacctgga aatatctgca ccccctcacag ttacctcaga agccctaact  31380
gtggctgccg ccgcaccttt aatggtcgcg ggcaacacac tcaccatgca atcacaggcc   31440
ccgctaaccg tgcacgactc caaacttagc attgccaccc aaggacccct cacagtgtca   31500
gaaggaaagc tagccctgca acatcaggc ccctcacca ccaccgatag cagtaccctt     31560
actatcactg cctcaccccc tctaactact gccactggta gcttgggcat tgacttgaaa   31620
gagcccattt atacacaaaa tggaaaacta ggactaaagt acggggctcc tttgcatgta   31680
acagacgacc taaacacttt gaccgtagca actggtccag gtgtgactat taataatact   31740
tccttgcaaa ctaaagttac tggagccttg ggttttgatt cacaaggcaa tatgcaactt   31800
aatgtagcag gaggactaag gattgattct caaaacagac gccttatact tgatgttagt   31860
tatccgtttg atgctcaaaa ccaactaaat ctaagactag acagggccc tctttttata    31920 aactcagccc acaacttgga tattaactac aacaaaggcc tttacttgtt tacagcttca   31980
aacaattcca aaaagcttga ggttaaccta agcactgcca aggggttgat gtttgacgct   32040
acagccatag ccattaatgc aggagatggg cttgaatttg gttcacctaa tgcaccaaac   32100
acaaatcccc tcaaaacaaa aattggccat ggcctagaat ttgattcaaa caaggctatg   32160
gttcctaaac taggaactgg ccttagtttt gacagcacag gtgccattac agtaggaaac   32220
```

```
aaaaataatg ataagctaac tttgtggacc acaccagctc catctcctaa ctgtagacta   32280
aatgcagaga aagatgctaa actcactttg gtcttaacaa aatgtggcag tcaaatactt   32340
gctacagttt cagttttggc tgttaaaggc agtttggctc caatatctgg aacagttcaa   32400
agtgctcatc ttattataag atttgacgaa aatggagtgc tactaaacaa ttccttcctg   32460
gacccagaat attggaactt tagaaatgga gatcttactg aaggcacagc ctatacaaac   32520
gctgttggat ttatgcctaa cctatcagct tatccaaaat ctcacggtaa aactgccaaa   32580
agtaacattg tcagtcaagt ttacttaaac ggagacaaaa ctaaacctgt aacactaacc   32640
attacactaa acggtacaca ggaaacagga gacacaactc caagtgcata ctctatgtca   32700 tttttcatggg actggtctgg ccacaactac attaatgaaa tatttgccac atcctcttac   32760
actttttcat acattgccca agaataaaga atcgtttgtg ttatgtttca acgtgtttat   32820
ttttcaattg cagaaaattt caagtcattt ttcattcagt agtatagccc caccaccaca   32880
tagcttatac agatcaccgt accttaatca aactcacaga accctagtat tcaacctgcc   32940
acctccctcc caacacacag agtacacagt cctttctccc cggctggcct taaaaagcat   33000
catatcatgg gtaacagaca tattcttagg tgttatattc cacacggttt cctgtcgagc   33060
caaacgctca tcagtgatat taataaactc cccgggcagc tcacttaagt tcatgtcgct   33120
gtccagctgc tgagccacag gctgctgtcc aacttgcggt tgcttaacgg gcggcgaagg   33180
agaagtccac gcctacatgg gggtagagtc ataatcgtgc atcaggatag ggcggtggtg   33240
ctgcagcagc gcgcgaataa actgctgccg ccgccgctcc gtcctgcagg aatacaacat   33300
ggcagtggtc tcctcagcga tgattcgcac cgcccgcagc ataaggcgcc ttgtcctccg   33360
ggcacagcag cgcaccctga tctcacttaa atcagcacag taactgcagc acagcaccac   33420
aatattgttc aaaatcccac agtgcaaggc gctgtatcca aagctcatgg cggggaccac   33480
agaacccacg tggccatcat accacaagcg caggtagatt aagtggcgac ccctcataaa   33540
cacgctggac ataaacatta cctcttttgg catgttgtaa ttcaccaccct cccggtacca   33600 tataaacctc tgattaaaca tggcgccatc caccaccatc ctaaaccagc tggccaaaac   33660
ctgcccgccg gctatacact gcagggaacc gggactggaa caatgacagt ggagagccca   33720
ggactcgtaa ccatggatca tcatgctcgt catgatatca atgttggcac aacacaggca   33780
cacgtgcata cacttcctca ggattacaag ctcctcccgc gttagaacca tatcccaggg   33840
aacaacccat tcctgaatca gcgtaaatcc cacactgcag ggaagacctc gcacgtaact   33900
cacgttgtgc attgtcaaag tgttacattc gggcagcagc ggatgatcct ccagtatggt   33960
agcgcgggtt tctgtctcaa aaggaggtag acgatcccta ctgtacggag tgcgccgaga   34020
caaccgagat cgtgttggtc gtagtgtcat gccaaatgga acgccggacg tagtcatatt   34080
tcctgaagca aaaccaggtg cgggcgtgac aaacagatct gcgtctccgg tctcgccgct   34140
tagatcgctc tgtgtagtag ttgtagtata tccactctct caaagcatcc aggcgccccc   34200
tggcttcggg ttctatgtaa actccttcat gcgccgctgc cctgataaca tccaccaccg   34260
cagaataagc cacacccagc caacctacac attcgttctg cgagtcacac acgggaggag   34320
cgggaagagc tggaagaacc atgtttttt tttattcca aaagattatc caaaacctca   34380
aaatgaagat ctattaagtg aacgcgctcc cctccggtgg cgtggtcaaa ctctacagcc   34440
aaagaacaga taatggcatt tgtaagatgt tgcacaatgg cttccaaaag gcaaacggcc   34500
ctcacgtcca agtggacgta aaggctaaac ccttcagggt gaatctcctc tataaacatt   34560
ccagcacctt caaccatgcc caaataattc tcatctcgcc accttctcaa tatatctcta   34620
```

-continued

```
agcaaatccc gaatattaag tccggccatt gtaaaaatct gctccagagc gccctccacc    34680
ttcagcctca agcagcgaat catgattgca aaaattcagg ttcctcacag acctgtataa    34740
gattcaaaag cggaacatta acaaaaatac cgcgatcccg taggtccctt cgcagggcca    34800
gctgaacata atcgtgcagg tctgcacgga ccagcgcggc cacttcccg ccaggaacca     34860
tgacaaaaga acccacactg attatgacac gcatactcgg agctatgcta accagcgtag    34920
ccccgatgta agcttgttgc atgggcggcg atataaaatg caaggtgctg ctcaaaaaat    34980
caggcaaagc ctcgcgcaaa aagaaagca catcgtagtc atgctcatgc agataaaggc     35040
aggtaagctc cggaaccacc acagaaaaag acaccatttt tctctcaaac atgtctgcgg    35100
gtttctgcat aaacacaaaa taaataaca aaaaacatt taaacattag aagcctgtct      35160
tacaacagga aaaacaaccc ttataagcat aagacggact acggccatgc cggcgtgacc    35220
gtaaaaaaac tggtcaccgt gattaaaaag caccaccgac agctcctcgg tcatgtccgg    35280
agtcataatg taagactcgg taaacacatc aggttgattc acatcggtca gtgctaaaaa    35340
gcgaccgaaa tagcccgggg gaatacatac ccgcaggcgt agagacaaca ttacagcccc    35400
cataggaggt ataacaaaat taataggaga gaaaaacaca taaacacctg aaaaaccctc    35460
ctgcctaggc aaaatagcac cctcccgctc cagaacaaca tacagcgctt ccacagcggc    35520
agccataaca gtcagcctta ccagtaaaaa agaaaaccta ttaaaaaaac accactcgac    35580
acggcaccag ctcaatcagt cacagtgtaa aaagggcca agtgcagagc gagtatatat     35640
aggactaaaa aatgacgtaa cggttaaagt ccacaaaaaa cacccagaaa accgcacgcg    35700
aacctacgcc cagaaacgaa agccaaaaaa cccacaactt cctcaaatcg tcacttccgt    35760
tttcccacgt tacgtaactt cccattttaa gaaaactaca attcccaaca catacaagtt    35820
actccgccct aaaacctacg tcacccgccc cgttcccacg ccccgcgcca cgtcacaaac    35880
tccacccct cattatcata ttggcttcaa tccaaaataa ggtatattat tgatgatg      35938
```

<210> SEQ ID NO 53
<211> LENGTH: 8
<212> TYPE: DNA
<213> ORGANISM: Adenovirus type 5

<400> SEQUENCE: 53 ctgacctc                                                              8

<210> SEQ ID NO 54
<211> LENGTH: 8
<212> TYPE: DNA
<213> ORGANISM: Adenovirus type 5

<400> SEQUENCE: 54 tcaccagg                                                              8

<210> SEQ ID NO 55
<211> LENGTH: 10
<212> TYPE: DNA
<213> ORGANISM: Adenovirus type 5

<400> SEQUENCE: 55
ggtgttttgg                                                           10

<210> SEQ ID NO 56
<211> LENGTH: 8
<212> TYPE: DNA

```
<213> ORGANISM: Adenovirus type 5

<400> SEQUENCE: 56 cagtatga                                                              8

<210> SEQ ID NO 57
<211> LENGTH: 10
<212> TYPE: DNA
<213> ORGANISM: Adenovirus type 5

<400> SEQUENCE: 57
taataaaaaa                                                           10

<210> SEQ ID NO 58
<211> LENGTH: 8
<212> TYPE: DNA
<213> ORGANISM: Adenovirus type 5

<400> SEQUENCE: 58 tgccttaa                                                              8

<210> SEQ ID NO 59
<211> LENGTH: 11
<212> TYPE: DNA
<213> ORGANISM: Adenovirus type 5

<400> SEQUENCE: 59
taaaaaaaaa t                                                         11

<210> SEQ ID NO 60
<211> LENGTH: 10
<212> TYPE: PRT
<213> ORGANISM: Homo sapiens

<400> SEQUENCE: 60

Ser Asn Thr Lys Val Asp Lys Lys Val Glu
1               5                   10

<210> SEQ ID NO 61
<211> LENGTH: 8
<212> TYPE: PRT
<213> ORGANISM: Homo sapiens

<400> SEQUENCE: 61

Thr Lys Val Asp Lys Arg Val Glu
1               5

<210> SEQ ID NO 62
<211> LENGTH: 400
<212> TYPE: PRT
<213> ORGANISM: Artificial Sequence
<220> FEATURE:
<223> OTHER INFORMATION: Synthetic

<400> SEQUENCE: 62

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60
```

```
Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
             85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
            130                 135                 140

Asp Asn Ile Ile Phe Ser Glu Glu Tyr Asn Thr Ser Asn Pro Asp Ser
145                 150                 155                 160

Asn Thr Lys Val Asp Lys Arg Val Glu Pro Lys Ser Cys Asp Lys Thr
                165                 170                 175

His Thr Cys Pro Pro Cys Pro Ala Pro Glu Leu Leu Gly Gly Pro Ser
                180                 185                 190

Val Phe Leu Phe Pro Pro Lys Pro Lys Asp Thr Leu Met Ile Ser Arg
                195                 200                 205

Thr Pro Glu Val Thr Cys Val Val Val Asp Val Ser His Glu Asp Pro
210                 215                 220

Glu Val Lys Phe Asn Trp Tyr Val Asp Gly Val Glu Val His Asn Ala
225                 230                 235                 240

Lys Thr Lys Pro Arg Glu Glu Gln Tyr Asn Ser Thr Tyr Arg Val Val
                245                 250                 255

Ser Val Leu Thr Val Leu His Gln Asp Trp Leu Asn Gly Lys Glu Tyr
                260                 265                 270

Lys Cys Lys Val Ser Asn Lys Ala Leu Pro Ala Pro Ile Glu Lys Thr
                275                 280                 285

Ile Ser Lys Ala Lys Gly Gln Pro Arg Glu Pro Gln Val Tyr Thr Leu
290                 295                 300

Pro Pro Ser Arg Asp Glu Leu Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
                340                 345                 350

Ser Asp Gly Ser Phe Phe Leu Tyr Ser Lys Leu Thr Val Asp Lys Ser
                355                 360                 365

Arg Trp Gln Gln Gly Asn Val Phe Ser Cys Ser Val Met His Glu Ala
                370                 375                 380

Leu His Asn His Tyr Thr Gln Lys Ser Leu Ser Leu Ser Pro Gly Lys
385                 390                 395                 400

<210> SEQ ID NO 63
<211> LENGTH: 398
<212> TYPE: PRT
<213> ORGANISM: Artificial Sequence
<220> FEATURE:
<223> OTHER INFORMATION: Synthetic

<400> SEQUENCE: 63

Met Gly Arg Gly Leu Leu Arg Gly Leu Trp Pro Leu His Ile Val Leu
 1               5                  10                  15

Trp Thr Arg Ile Ala Ser Thr Ile Pro Pro His Val Gln Lys Ser Val
             20                  25                  30
```

```
Asn Asn Asp Met Ile Val Thr Asp Asn Asn Gly Ala Val Lys Phe Pro
             35                  40                  45

Gln Leu Cys Lys Phe Cys Asp Val Arg Phe Ser Thr Cys Asp Asn Gln
     50                  55                  60

Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
                 85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
                115                 120                 125

Pro Gly Glu Thr Phe Phe Met Cys Ser Cys Ser Ser Asp Glu Cys Asn
            130                 135                 140

Asp Asn Ile Ile Phe Ser Glu Glu Tyr Asn Thr Ser Asn Pro Asp Thr
145                 150                 155                 160

Lys Val Asp Lys Arg Val Glu Pro Lys Ser Cys Asp Lys Thr His Thr
                165                 170                 175

Cys Pro Pro Cys Pro Ala Pro Glu Leu Leu Gly Gly Pro Ser Val Phe
                180                 185                 190

Leu Phe Pro Pro Lys Pro Lys Asp Thr Leu Met Ile Ser Arg Thr Pro
            195                 200                 205

Glu Val Thr Cys Val Val Val Asp Val Ser His Glu Asp Pro Glu Val
        210                 215                 220

Lys Phe Asn Trp Tyr Val Asp Gly Val Glu Val His Asn Ala Lys Thr
225                 230                 235                 240

Lys Pro Arg Glu Glu Gln Tyr Asn Ser Thr Tyr Arg Val Val Ser Val
                245                 250                 255

Leu Thr Val Leu His Gln Asp Trp Leu Asn Gly Lys Glu Tyr Lys Cys
                260                 265                 270

Lys Val Ser Asn Lys Ala Leu Pro Ala Pro Ile Glu Lys Thr Ile Ser
            275                 280                 285

Lys Ala Lys Gly Gln Pro Arg Glu Pro Gln Val Tyr Thr Leu Pro Pro
        290                 295                 300

Ser Arg Asp Glu Leu Thr Lys Asn Gln Val Ser Leu Thr Cys Leu Val
305                 310                 315                 320

Lys Gly Phe Tyr Pro Ser Asp Ile Ala Val Glu Trp Glu Ser Asn Gly
                325                 330                 335

Gln Pro Glu Asn Asn Tyr Lys Thr Thr Pro Pro Val Leu Asp Ser Asp
                340                 345                 350

Gly Ser Phe Phe Leu Tyr Ser Lys Leu Thr Val Asp Lys Ser Arg Trp
            355                 360                 365

Gln Gln Gly Asn Val Phe Ser Cys Ser Val Met His Glu Ala Leu His
        370                 375                 380

Asn His Tyr Thr Gln Lys Ser Leu Ser Leu Ser Pro Gly Lys
385                 390                 395
```

IMMUNOMODULATORY FUSION PROTEINS

CROSS REFERENCE TO RELATED APPLICATIONS

This application claims the benefit of, and priority to, U.S. provisional patent application Ser. No. 62/400,338, filed Sep. 27, 2016, and U.S. provisional patent application Ser. No. 62/484,841 filed Apr. 12, 2017, each of which are hereby incorporated by reference herein in their entirety.

FIELD OF THE INVENTION

The field of the invention is molecular biology, specifically immunology and fusion proteins, e.g., cytokine receptor fusion proteins.

BACKGROUND

Cytokines are small, secreted cell signaling proteins that have a wide range of activities including regulation of cell growth and differentiation and modulation of immune function. Cytokines, cytokine receptors, and certain other immunomodulatory proteins have been used as therapeutics to treat a variety of medical conditions. However, the administration of such proteins, for example, by subcutaneous or vascular routes, can result in inappropriate cellular and extracellular localization, thereby limiting therapeutic activity and/or increasing the risk of toxicity.

Transforming growth factor-β (TGFβ) is a pleiotropic cytokine with immunoregulatory properties, such as the limitation and termination of inflammatory and allergic immune responses (Taylor (2009) J. LEUKOC. BIOL. 85(1):29-33). TGFβ has been implicated in inflammatory, malignant, infectious and autoimmune diseases as well as osteoporosis and fibrosis, including cirrhosis and systemic sclerosis. In particular, persistently high levels of TGFβ in tumors are associated with immune tolerance, angiogenesis, metastasis, and increased tumor extracellular matrix deposition, all of which may drive cancer progression and resistance to therapy.

Several therapeutics have been developed to trap or sequester TGFβ, and, therefore, reduce or modulate TGFβ activity. Examples include monoclonal antibodies directed against TGFβ, for example, fresolimumab, which has been administered in several clinical trials for the treatment of cancer and systemic sclerosis (Connolly et al. (2012) INT. J. BIOL. SCI. 8(7): 964-78).

An alternative approach to monoclonal antibodies includes the use of recombinant Fc-fusion proteins containing a soluble portion of the extracellular domain of the TGFβ type II receptor (TβRII) or the TGFβ type III receptor (TβRII, or betaglycan) (Connolly et al. (2012) supra). Such molecules, known as TGFβ traps, typically contain extracellular domains of the two chains of the dimeric TGFβ receptor complex. Expression of a soluble TβRII-Fc fusion has been coupled to an oncolytic adenovirus and shown to result in a significant reduction of primary tumor growth and osteolytic bone destruction (Hu et al. (2010) HUM. GENE THER. 21(11): 1623-9).

Despite the efforts to date, there is a need for improved fusion proteins, for example, cytokine receptor fusion proteins, in particular, improved TGFβ receptor fusion proteins that neutralize the biological activity of human TGFβ for treating disorders in human patients mediated by TGFβ.

SUMMARY OF THE INVENTION

The invention is based, in part, upon the discovery of linker sequences that improve the function of fusion proteins, e.g., cytokine receptor fusion proteins, e.g., TGFβ type II (TβRII) receptor fusion proteins, e.g., TGFβ traps. The linker sequences may permit a ligand binding portion of a fusion protein (e.g., a cytokine receptor) to bind optimally to a ligand (e.g., a cytokine), provide temporal and spatial colocalization of two or more components of a fusion protein (e.g., two subunits of a dimeric cytokine), optimize expression from an expression vector (e.g., a viral vector), reduce immunogenicity, or provide a cleavage site to allow for release of a component of the fusion protein. For example, the linker sequences may provide sufficient flexibility to allow a ligand binding domain of a cytokine receptor to adopt a native conformation in the context of a fusion protein, and minimize the potential immunogenicity of the fusion protein for use as a therapeutic agent.

In one aspect, the invention provides an isolated fusion protein that comprises, for example, in an N- to C-terminal orientation: a first portion of an extracellular domain, transmembrane domain, or intracellular domain of a cytokine, cytokine receptor, or immunomodulatory protein; an amino acid linker; and at least one of, a second portion of an extracellular domain, transmembrane domain, or intracellular domain of a cytokine, cytokine receptor, or immunomodulatory protein; an immunoglobulin (Ig) hinge region; and an immunoglobulin (Ig) Fc domain. In certain embodiments, the linker comprises from about 5 to about 40 amino acid residues.

In another aspect, the invention provides an isolated fusion protein that comprises, in an N- to C-terminal orientation: a soluble portion of an extracellular domain of a cytokine receptor; an amino acid linker; an immunoglobulin (Ig) hinge region; and an immunoglobulin (Ig) Fc domain; wherein the linker comprises from about 5 to about 40 amino acid residues.

In certain embodiments of any of the foregoing fusion proteins, the amino acid linker may comprise, e.g., from about 5 to about 15, from about 5 to about 20, from about 5 to about 30, from about 10 to about 15, from about 10 to about 20, from about 10 to about 30, from about 10 to about 40, from about 15 to about 20, from about 15 to about 30, or from about 15 to about 40 amino acid residues.

In certain embodiments of any of the foregoing fusion proteins, the amino acid linker sequence is derived from an endogenous human protein, e.g., IgG1, IgG2, IgG3, IgG4, IgA1, IgA2, IgD, IgE, IgM, albumin, or casein. In certain embodiments, the amino acid linker comprises a C-terminal portion of an immunoglobulin (Ig) CH1 domain, e.g., an IgG1, IgG2, IgG3, IgG4, IgA1, IgA2, IgD, IgE, or IgM CH1 domain. In certain embodiments, the amino acid linker comprises an amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 60, and SEQ ID NO: 61. In certain embodiments, the amino acid linker comprises a C-terminal portion of an IgG1 CH1 domain, e.g., the amino acid linker comprises an amino acid sequence selected from SEQ ID NO: 1, SEQ ID NO: 60, and SEQ ID NO: 61, e.g., the amino acid sequence of SEQ ID NO: 1.

In certain embodiments of any of the foregoing fusion proteins, the amino acid linker comprises a sequence derived from a cytokine, signaling molecule, immunomodulatory protein or peptide, or a biologically active peptide.

In certain embodiments of any of the foregoing fusion proteins, the amino acid linker comprises a cleavage site, e.g., a proteolytic cleavage site, e.g., a proteolytic cleavage site that is cleaved by a protease present in the endoplasmic reticulum or golgi of a eukaryotic cell. In certain embodiments, the proteolytic cleavage site is a furin cleavage site, e.g., a furin cleavage site comprising the sequence $RX_1X_2R$ (SEQ ID NO: 50), wherein $X_1$ is any amino acid, and $X_2$ is Lys or Arg, e.g., a furin cleavage site comprising the sequence RAKR (SEQ ID NO: 51). In certain embodiments of any of the foregoing fusion proteins, the amino acid linker is proteolytically stable in a mammal or plant.

In certain embodiments of any of the foregoing fusion proteins, the soluble portion of an extracellular domain of a cytokine receptor is a soluble portion of an extracellular domain of the human TβRII receptor. For example, in certain embodiments, the soluble portion of an extracellular domain of a cytokine receptor comprises the amino acid sequence of SEQ ID NO: 12 or amino acid residues 23-159 of SEQ ID NO: 12.

In certain embodiments of any of the foregoing fusion proteins, the fusion protein comprises one or more of TGF-β, CD80, CD19, CD20, IL-1, IL-3, IL-4, IL-5, IL-6, IL-8, IL-9, IL-12B/p40, IL-23A/p19, IL27A/p28, IL-27B/EBI3, CD154, CD86, CD137, CD137L, IFN-α, IFN-β, BORIS/CTCFL, FGF, ICAM, IL-24, MAGE, NY-ESO-1, angiostatin, endostatin, acetylcholine, interferon-gamma, DKK1/Wnt, p53, thymidine kinase, an anti-PD-1 antibody heavy chain or light chain, and an anti-PD-L1 antibody heavy chain or light chain, or a functional fragment thereof. For example, in certain embodiments, a fusion protein may comprise: CD80 and CD137L; IL-23A/p19 and IL-12B/p40; or IL-27A/p28 and IL-27B/EBI3.

In certain embodiments of any of the foregoing fusion proteins, the Ig hinge region is selected from an IgG1, IgG2, IgG3, IgG4, IgA1, IgA2, IgD, IgE, and IgM hinge region, and the Ig Fc domain, is selected from IgG1, IgG2, IgG3, IgG4, IgA1, IgA2, IgD, IgE, and IgM Fc domain. In certain embodiments, the Ig hinge region and Fc domain together comprise an amino acid sequence selected from SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21. In certain embodiments, the Ig Fc, Ig hinge region, and Ig CH1 domain are derived from a single immunoglobulin.

In certain embodiments of any of the foregoing fusion proteins, the fusion protein comprises an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 62, and SEQ ID NO: 63. In certain embodiments, the fusion protein comprises an amino acid sequence selected from SEQ ID NO: 22, SEQ ID NO: 62, and SEQ ID NO: 63. In certain embodiments, the fusion protein comprises the amino acid sequence of SEQ ID NO: 22.

In certain embodiments of any of the foregoing fusion proteins, the fusion protein comprises an amino acid sequence having greater than 80%, 85%, 90%, 95%, 96%, 97%, 98% or 99% sequence identity to a sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 62, and SEQ ID NO: 63.

In another aspect, the invention provides a dimeric cytokine binding protein comprising two of any of the foregoing fusion proteins covalently linked together, wherein each fusion protein comprises an extracellular domain of a cytokine receptor, and wherein the two extracellular domains together define a binding site for a cytokine.

In another aspect, the invention provides a nucleic acid comprising a nucleotide sequence that encodes for any of the foregoing fusion proteins.

In another aspect, the invention provides an expression vector comprising any of the foregoing nucleic acids. The expression vector may be an oncolytic virus, e.g., the virus may selectively replicate in a hyperproliferative cell and/or selectively express the fusion protein in a hyperproliferative cell. In certain embodiments, the oncolytic virus is an oncolytic adenovirus, e.g., an oncolytic type 2 or type 5 adenovirus.

In certain embodiments of any of the foregoing expression vectors, the nucleotide sequence encoding the fusion protein is inserted into an E1b-19K insertion site located between the start site of E1b-19K and the start site of E1b-55K. In certain embodiments, the E1b-19K insertion site is located between the start site of E1b-19K and the stop site of E1b-19K. In certain embodiments, the E1b-19K insertion site comprises a deletion of about 200 nucleotides, e.g., 203 nucleotides adjacent the start site of E1b-19K. In certain embodiments, the E1b-19K insertion site comprises a deletion corresponding to nucleotides 1714-1916 of the Ad5 genome (SEQ ID NO: 52), or, the nucleotide sequence encoding the fusion protein is inserted between nucleotides corresponding to 1714 and 1916 of the Ad5 genome (SEQ ID NO: 5). In certain embodiments, the nucleotide sequence encoding the fusion protein is inserted between CTGACCTC (SEQ ID NO: 53) and TCACCAGG (SEQ ID NO: 54), e.g., the adenovirus comprises, in a 5' to 3' orientation, CTGACCTC (SEQ ID NO: 53), the nucleotide sequence encoding the fusion protein, and TCACCAGG (SEQ ID NO: 54).

In certain embodiments of any of the foregoing expression vectors, the adenovirus may comprise a deletion of at least one Pea3 binding site, or a functional portion thereof, e.g., the adenovirus may comprise a deletion of nucleotides corresponding to about −300 to about −250 upstream of the initiation site of E1a or a deletion of nucleotides corresponding to −305 to −255 upstream of the initiation site of E1a. In certain embodiments, the adenovirus may comprise a deletion of nucleotides corresponding to 195-244 of the Ad5 genome (SEQ ID NO: 52), and/or the recombinant adenovirus may comprise the sequence GGTGTTTTGG (SEQ ID NO: 55). In certain embodiments, the recombinant oncolytic adenovirus may comprise a deletion of at least one Pea3 binding site, or a functional portion thereof, and not comprise a deletion of an E2F binding site. In certain embodiments, the adenovirus may comprise a deletion of at least one E2F binding site, or a functional portion thereof. In certain embodiments, the adenovirus may comprise a deletion of at least one E2F binding site, or a functional portion thereof, and not comprise a deletion of a Pea3 binding site.

In certain embodiments of any of the foregoing expression vectors, the adenovirus may comprise an E3 deletion. In certain embodiments, the E3 deletion comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or from about 3000 to about 3185 nucleotides. In certain embodiments, the E3 deletion site is located between the stop site of pVIII and the start site of Fiber. In certain embodiments, the E3 deletion site is located between the stop site of E3-10.5K and the stop site of E3-14.7K. In certain embodiments, the E3 deletion comprises a deletion of from about 500 to about 1551, from about 500 to about 1500, from about 500 to about 1000, from about 1000 to about 1551, from about 1000 to about 1500, or from about 1500 to about 1551 nucleotides adjacent to the stop site of E3-10.5K. In certain embodiments, the E3 deletion comprises a deletion of about 1050 nucleotides adjacent to the stop site of E3-10.5K, e.g., the E3 deletion comprises a deletion of 1064 nucleotides adjacent to the stop site of E3-10.5K. In certain embodiments, the E3 deletion comprises a deletion corresponding to the Ad5 dl309 E3 deletion. In certain embodiments, the E3 deletion comprises a deletion corresponding to nucleotides 29773-30836 of the Ad5 genome (SEQ ID NO: 52).

In certain embodiments, the nucleotide sequence encoding the fusion protein is inserted into the E3 deletion, for example, the nucleotide sequence is inserted between CAGTATGA (SEQ ID NO: 56) and TAATAAAAAA (SEQ ID NO: 57), e.g., the adenovirus comprises, in a 5' to 3' orientation, CAGTATGA (SEQ ID NO: 56), the nucleotide sequence encoding the fusion protein, and TAATAAAAAA (SEQ ID NO: 57).

In certain embodiments, the oncolytic adenovirus comprises a nucleotide sequence encoding a fusion protein inserted into an E1b-19K insertion site, wherein the insertion site is located between the start site of E1b-19K and the start site of E1b-55K, and/or a modified E1a regulatory sequence, wherein at least one Pea3 binding site, or a functional portion thereof, is deleted.

In another aspect, the invention provides a host cell comprising any of the foregoing the expression vectors. In another aspect, the invention provides a method of producing a fusion protein comprising growing a host cell under conditions to express the fusion protein and purifying the fusion protein. In another aspect, the invention provides a method of expressing a fusion protein in a target cell comprising exposing the cell to an effective amount of any of the foregoing expression vectors. In certain embodiments, the fusion protein is cleaved posttranslationally into two polypeptide chains.

In another aspect, any of foregoing fusion proteins or expression vectors can be used, e.g., to reduce cytokine activity in a subject, thereby treating various medical indications that are mediated by a cytokine, for example, TGFβ. In another aspect, any of the foregoing fusion proteins or expression vectors can be used to inhibit proliferation of tumor cells in vitro and/or in vivo, inhibit tumor growth in a subject in need thereof, or treat cancer in a subject in need thereof. The subject may be, e.g., an animal, e.g., a mammal, e.g., a human, e.g., a pediatric human. For example, when administered to a human subject with cancer, the fusion proteins or expression vectors inhibit or reduce tumor growth, or, reduce the tumor load, in the subject.

In certain embodiments, the cancer may be selected from melanoma, squamous cell carcinoma of the skin, basal cell carcinoma, head and neck cancer, breast cancer, anal cancer, cervical cancer, non-small cell lung cancer, mesothelioma, small cell lung cancer, renal cell carcinoma, prostate cancer, gastroesophageal cancer, colorectal cancer, testicular cancer, bladder cancer, ovarian cancer, liver cancer, hepatocellular carcinoma, cholangiocarcinoma, brain and central nervous system cancer, thyroid cancer, parathyroid cancer (e.g., parathyroid carcinoma), endometrial cancer, neuroendocrine cancer, lymphoma (e.g., Hodgkin and non-Hodgkin), leukemia, merkel cell carcinoma, gastrointestinal stromal tumors, multiple myeloma, uterine cancer, a sarcoma, kidney cancer, ocular cancer, pancreatic cancer, and a germ cell cancer (e.g., ovarian germ cell cancer). In certain embodiments, the cancer may be selected from leukemia, breast cancer, lung cancer, pancreatic cancer, endometrial cancer, ovarian cancer, prostate cancer, cervical cancer, brain cancer, skin cancer, colorectal cancer, gastric cancer, head and neck cancer, and leukemia.

In certain embodiments, the fusion protein or expression vector is administered in combination with one or more therapies selected from surgery, radiation, chemotherapy, immunotherapy, hormone therapy, and virotherapy. In certain embodiments, the fusion protein or expression vector is administered in combination with a lymphocyte, e.g., a T-cell, e.g., a CAR T-cell.

Any of the foregoing fusion proteins or expression vectors can also be used to treat an inflammatory condition or infection in a subject in need thereof.

These and other aspects and advantages of the invention are illustrated by the following figures, detailed description and claims.

DESCRIPTION OF THE DRAWINGS

The invention can be more completely understood with reference to the following drawings.

FIG. 2 depicts a sequence alignment of the amino acid sequences of the human IgG1, IgG2, IgG3, IgG4, IgA1, IgA2, IgD, IgE, and IgM CH1 domains (top) and CH2 domains (bottom).

DETAILED DESCRIPTION

The invention provides an isolated fusion protein for use in the treatment of a variety of medical conditions, for example, in inhibiting proliferation of a tumor cell, inhibiting tumor growth, treating cancer, treating an inflammatory condition, or treating an infection, in a subject. Exemplary fusion proteins comprise: a first portion of an extracellular domain, transmembrane domain, or intracellular domain of a cytokine, cytokine receptor, or immunomodulatory protein; an amino acid linker; and at least one of, a second portion of an extracellular domain, transmembrane domain, or intracellular domain of a cytokine, cytokine receptor, or immunomodulatory protein; an immunoglobulin (Ig) hinge region; and an immunoglobulin (Ig) Fc domain. In certain embodiments, the linker comprises from about 5 to about 40 amino acid residues. Exemplary fusion proteins of the invention include cytokine traps.

A cytokine trap, e.g. a TGFβ trap, is a molecule containing a soluble portion of the extracellular domain of a cytokine receptor, e.g., a TGFβ receptor, e.g., the TGFβ type II receptor (TβRII), designed to bind or otherwise sequester a target cytokine. In a cytokine trap, the extracellular domain of a cytokine receptor may be fused to an immunoglobulin (Ig) hinge region and immunoglobulin (Ig) Fc domain which can allow, e.g., for increased stability, Fc effector functions and/or multimerization, e.g., dimerization. Dimerization afforded by fusion to an Ig hinge region and Ig Fc domain is particularly advantageous for cytokine receptors that exist as dimeric receptor complexes on the cellular surface, such as, e.g., TβRII.

Figure 1A:
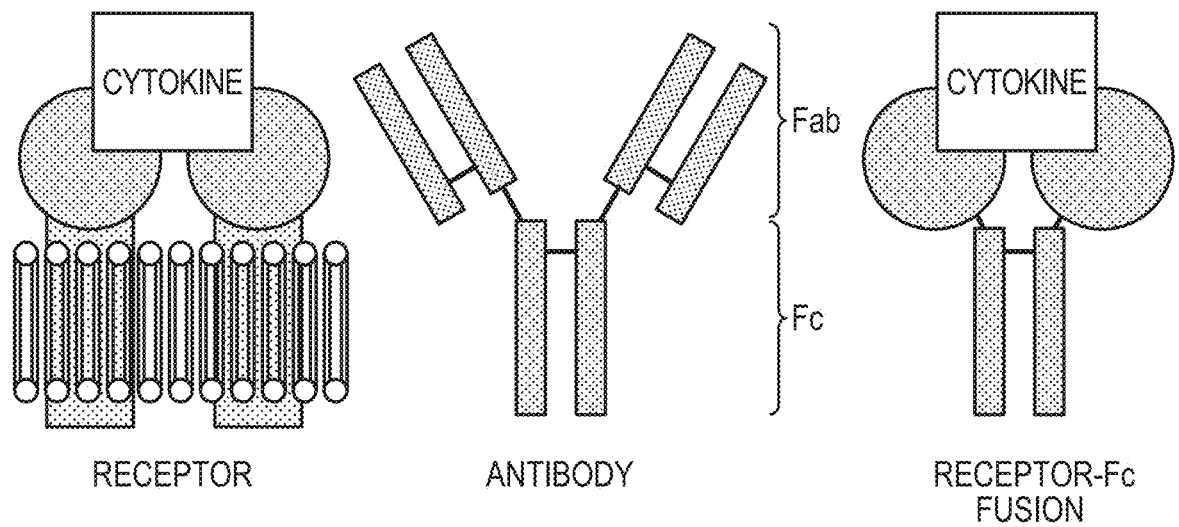
FIG. 1A depicts a schematic of a dimeric cytokine receptor on the cell surface (left), an antibody (middle), and a receptor-Fc fusion that optimally binds a target cytokine (right).

Conventional cytokine traps, e.g., TGFβ traps, comprise two polypeptide chains, each polypeptide chain comprising a soluble portion of an extracellular domain of a cytokine receptor fused to an Ig hinge region and an Ig Fc domain. The soluble portion of the extracellular domain of the cytokine receptor typically is fused directly to the Ig hinge region, without any intervening sequence. The two polypeptide chains are covalently linked by disulfide bonds between cysteine residues in each of the Ig hinge regions. Each polypeptide chain provides a soluble portion of an extracellular domain of a cytokine receptor, e.g., TβRII, and the two soluble portions of an extracellular domain of a cytokine receptor together define a binding site for a cytokine. A schematic representation of a dimeric cytokine receptor, an immunoglobulin (antibody) molecule, and a dimeric protein comprising two covalently linked fusion proteins each comprising a soluble portion of an extracellular domain of a cytokine receptor fused to an Ig hinge region and an Ig Fc domain is depicted in FIG. 1A.

The invention is based, in part, upon the discovery that conventional cytokine traps comprising a fusion protein of a soluble portion of an extracellular domain of a cytokine receptor to an Ig hinge region and Ig Fc domain, e.g. TGFβ traps, do not optimally bind their target cytokine. For example, a conventional TGFβ trap does not provide sufficient flexibility between the two TβRII ligand binding domains to allow the two TβRII ligand binding domains to come together in an optimal configuration to define a TGFβ binding site.

Figure 1B:
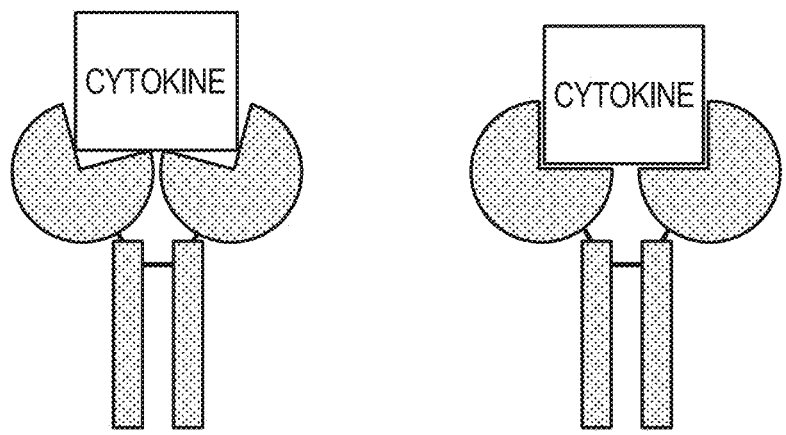
FIG. 1B depicts a receptor-Fc fusion, e.g., a cytokine trap, that is sterically constrained from optimal binding to a target cytokine (left), or that adopts an optimal binding configuration (right).

Thus, in one aspect, the invention provides an isolated fusion protein that comprises, in an N- to C-terminal orientation: a soluble portion of an extracellular domain of a cytokine receptor; an amino acid linker; an immunoglobulin (Ig) hinge region; and an immunoglobulin (Ig) Fc domain; wherein the linker comprises from about 5 to about 40 amino acid residues. The linker sequence allows, e.g., the binding domain in the extracellular domain of the cytokine receptor to bind optimally to its target cytokine. This is especially important when the cytokine binding protein is a dimer that comprises two of the foregoing fusion proteins that together define a binding site to bind the target cytokine. Without the linker, the two binding domains may be sterically constrained from forming the optimal binding site (FIG. 1B). Various features and aspects of the invention are discussed in more detail below.

I. Fusion Proteins

Exemplary fusion proteins may comprise: a first portion of an extracellular domain, transmembrane domain, or intracellular domain of a cytokine, cytokine receptor, or immunomodulatory protein; an amino acid linker; and at least one of, a second portion of an extracellular domain, transmembrane domain, or intracellular domain of a cytokine, cytokine receptor, or immunomodulatory protein; an immunoglobulin (Ig) hinge region; and an immunoglobulin (Ig) Fc domain. It is contemplated that the first portion of an extracellular domain, transmembrane domain, or intracellular domain of a cytokine, cytokine receptor, or immunomodulatory protein may be the same or different from the second portion of an extracellular domain, transmembrane domain, or intracellular domain of a cytokine, cytokine receptor, or immunomodulatory protein For example, a disclosed fusion protein may comprise, in an N- to C-terminal orientation: a soluble portion of an extracellular domain of a cytokine receptor; an amino acid linker; an immunoglobulin (Ig) hinge region; and an immunoglobulin (Ig) Fc domain; wherein the linker comprises from about 5 to about 40 amino acid residues.

Exemplary cytokines include IL-1α, IL-1β, IL-18, IL-4, IL-9, IL-13, IL-3, IL-5, IL-6, IL-11, G-CSF, LIF, OSM, IL-10, IL-20, IL-14, IL-16, IL-17, IFN-α, IFN-β, IFN-γ, CD154, LT-β, TNF-β, 4-1BBL APRIL, CD153, CD178, LIGHT, TALL-1, TRAIL, TWEAK, TRANCE, TGF-β1, TGF-β2, TGF-β3, Epo, Tpo, Flt-3L, SCF, M-CSF, and MSP.

As used herein, an "immunomodulatory" protein refers to a protein that modulates the function of the immune system of a subject Immunomodulatory proteins may, for example, modulate the function of, e.g., B-cells, T cells and/or the production of antibodies. Exemplary immunomodulatory proteins include checkpoint inhibitors. Exemplary immunomodulatory proteins may include, e.g., PD-1, or PD-L1, or any protein that modulates the activity thereof. Further exemplary immunomodulatory proteins may include an anti PD-1 antibody or anti-PD-L1 antibody.

As used herein, a "soluble portion of an extracellular domain of a cytokine receptor" refers to any extracellular domain of a cytokine receptor or fragment of an extracellular domain of a cytokine receptor that is capable of binding to a target cytokine. It is understood that the soluble portion of an extracellular domain of a cytokine receptor also contemplates portions of the extracellular domain that comprise a binding domain that, either alone or in combination with a second binding domain (e.g., in the case of dimeric fusion proteins) is capable of binding to a target cytokine.

Exemplary cytokine receptors include type I cytokine receptors (e.g., GM-CSF receptors, G-CSF receptors, type I IL receptors, Epo receptors, LIF receptors, CNTF receptors, or TPO receptors), type II cytokine receptors (e.g., IFN-alpha receptors (e.g., IFNAR1 or IFNAR2), IFN-beta receptors, IFN-gamma receptors (e.g., IFNGR1 or IFNGR2), chemokine receptors (e.g., CC chemokine receptors, CXC chemokine receptors, CX3C chemokine receptors, or XC chemokine receptors), tumor necrosis factor superfamily receptors (TNFRs; e.g., TNFRSF5/CD40, TNFRSF8/CD30, TNFRSF7/CD27, TNFRSF1A/TNFR1/CD120a, or TNFRSF1B/TNFR2/CD120b), TGFβ superfamily receptors (e.g., TGFβ type I receptor or TGFβ type II receptor), or immunoglobulin (Ig) superfamily receptors (e.g., interleukin-1 receptors, CSF-1R, PDGFR (e.g., PDGFRA or PDGFRB), or SCFR). Preferred cytokine receptors include dimeric cytokine receptors, e.g., TGFβ superfamily receptors, e.g., the human TGFβ type II receptor (TβRII). In certain embodiments, the soluble portion of an extracellular domain of a cytokine receptor is a soluble portion of an extracellular domain of the human TGFβ type II receptor (TβRII), e.g., comprising the amino acid sequence of SEQ ID NO: 12, or an amino acid sequence having greater than 85%, 90%, 95%, 96%, 97%, 98% or 99% sequence identity to SEQ ID NO: 12, and/or a fragment thereof that comprises a binding domain that binds to TGFβ.

The soluble portion of the extracellular domain of a cytokine receptor retains its ability to bind its native ligand. In certain embodiments, the soluble portion of the extracellular domain retains at least 50%, 60%, 70%, 80%, 90%, or 95% of the binding activity to its native ligand when compared to the full length cytokine receptor.

In certain embodiments, the fusion protein can comprise, e.g., one or more of TβRII, TGF-β, CD80, CD19, CD20, IL-1, IL-3, IL-4, IL-5, IL-6, IL-8, IL-9, IL-12B/p40, IL-23A/p19, IL-27A/p28, IL-27B/EBI3, CD154, CD86, CD137, CD137L, IFN-α, IFN-β, BORIS/CTCFL, FGF, ICAM, IL-24, MAGE, NY-ESO-1, angiostatin, endostatin, acetylcholine, interferon-gamma, DKK1/Wnt, p53, thymidine kinase, an anti-PD-1 antibody heavy chain or light chain, and an anti-PD-L1 antibody heavy chain or light chain, or a functional fragment thereof. For example, a fusion protein may comprise: CD80 and CD137L; IL-23A/p19 and IL-12B/p40; or IL-27A/p28 and IL-27B/EBI3.

As used herein, the term "immunoglobulin (Ig) hinge region" refers to the amino acid sequence that typically connects CH1 and CH2 domains of an immunoglobulin heavy chain constant region. An Ig hinge region may include, e.g., one or more cysteine residues capable of forming disulfide bonds with cysteine residues in another protein chain. As used herein, the term "immunoglobulin (Ig) Fc domain" refers to a fragment of an immunoglobulin heavy chain constant region that is capable of binding to an Fc receptor. An Ig Fc domain may include, e.g., an immunoglobulin (Ig) CH2 and CH3 domain. Boundaries between Ig CH1, CH2, and CH3 domains are well known in the art, and can be found, e.g., in the PROSITE database (available on the world wide web at prosite.expasy.org). For clarity, alignments of the amino acid sequences of the human IgG1, IgG2, IgG3, IgG4, IgA1, IgA2, IgD, IgE, and IgM CH1 and CH2 domains are provided in FIG. 2.

In certain embodiments, the Ig hinge region is selected from an IgG1, IgG2, IgG3, IgG4, IgA1, IgA2, IgD, IgE, and IgM hinge region, and the Ig Fc domain, is selected from an IgG1, IgG2, IgG3, IgG4, IgA1, IgA2, IgD, IgE, and IgM Fc domain. In certain embodiments, the Ig hinge region and Fc domain together comprise an amino acid sequence selected from SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21. In certain embodiments, the Ig hinge region and Fc domain together comprise an amino acid sequence having greater than 85%, 90%, 95%, 96%, 97%, 98% or 99% identity with a sequence selected from SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21.

The amino acid linker may permit a ligand binding portion of a fusion protein (e.g., a cytokine receptor) to bind optimally to a ligand (e.g., a cytokine), provide temporal and spatial colocalization of two or more components of a fusion protein (e.g., two subunits of a dimeric cytokine), optimize expression from an expression vector (e.g., a viral vector), reduce immunogenicity, or provide a cleavage site to allow for release of a component of the fusion protein.

The amino acid linker may comprise, e.g., from about 5 to about 15, from about 5 to about 20, from about 5 to about 25, from about 5 to about 30, from about 5 to about 35, from about 5 to about 40, from about 10 to about 15, from about 10 to about 20, from about 10 to about 25, from about 10 to about 30, from about 10 to about 35, from about 10 to about 40, from about 15 to about 20, from about 15 to about 25, from about 15 to about 30, from about 15 to about 35, or from about 15 to about 40 amino acid residues. The amino acids in the linker can be naturally occurring amino acids or modified amino acids.

In certain embodiments, the amino acid linker sequence is derived from an endogenous human protein, e.g., IgG1, IgG2, IgG3, IgG4, IgA1, IgA2, IgD, IgE, IgM, albumin, or casein. In certain embodiments, the amino acid linker comprises a C-terminal portion, for example, from about 5 to about 40 amino acids, of an immunoglobulin (Ig) CH1 domain, e.g., an IgG1, IgG2, IgG3, IgG4, IgA1, IgA2, IgD, IgE, or IgM CH1 domain. In certain embodiments, the amino acid linker comprises an amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9. SEQ ID NO: 10, SEQ ID NO: 11, SEQ ID NO: 60, and SEQ ID NO: 61. In certain embodiments, the amino acid linker comprises a sequence having greater than 80%, 85%, 90%, 95%, 96%, 97%, 98% or 99% sequence identity to an amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9. SEQ ID NO: 10, SEQ ID NO: 11, SEQ ID NO: 60, and SEQ ID NO: 61.

A protein or polypeptide is "derived from" a reference protein or polypeptide if it comprises an amino acid sequence that is substantially similar to all or a corresponding portion of the wild-type amino acid sequence of the reference protein or polypeptide. In certain embodiments, a protein or polypeptide that is derived from a wild-type protein or polypeptide may have one or more amino acid substitutions relative to the wild-type protein or polypeptide. For example, it is contemplated that a protein or polypeptide that is derived from a wild-type protein or polypeptide may have greater than 70%, 75%, 80%, 85%, 90%, 95%, 96%, 97%, 98% or 99% sequence identity to the wild-type protein or polypeptide. Further, it is contemplated that a protein or polypeptide that is derived from a wild-type protein or polypeptide may contain on more conservative substitutions relative to the wild-type protein or polypeptide. As used herein, the term "conservative substitution" refers to a substitution with a structurally similar amino acid. For example, conservative substitutions may include those within the following groups: Ser and Cys; Leu, Ile, and Val; Glu and Asp; Lys and Arg; Phe, Tyr, and Trp; and Gln, Asn, Glu, Asp, and His. Conservative substitutions may also be defined by the BLAST (Basic Local Alignment Search Tool) algorithm, the BLOSUM substitution matrix (e.g., BLOSUM 62 matrix), or the PAM substitution:p matrix (e.g., the PAM 250 matrix).

In certain embodiments, the amino acid linker sequence is derived from a cytokine, signaling molecule, immunomodulatory protein or peptide, or a biologically active peptide.

Further contemplated linker sequences include glycine- and serine-rich linkers, e.g., $(G_4S)_3$ (SEQ ID NO: 49). Additional exemplary linker sequences are disclosed, e.g., in George et al. (2003) PROTEIN ENGINEERING 15:871-879 and U.S. Pat. Nos. 5,482,858 and 5,525,491.

In certain embodiments, the amino acid linker may comprise a cleavage site, e.g., a proteolytic or a non-proteolytic cleavage site. In certain embodiments, the proteolytic cleavage site is cleaved by a protease present in a specific tissue, organelle or intracellular compartment. In certain embodiments, the linker comprises a proteolytic cleavage site and two cysteine residues that result in a disulfide linkage following proteolytic cleavage. In certain embodiments, the proteolytic cleavage site is cleaved by a protease selected from a matrix metalloproteinase (MMP), furin, PC1, PC2, PC3, cathepsin B, proteinase 3, and caspase 3. In certain embodiments, the cleavage site is a proteolytic cleavage site that is cleaved by a protease that is present in the endoplasmic reticulum or golgi of a eukaryotic cell. In certain embodiments, the proteolytic cleavage site is a furin cleavage site. Furin is a protease that is ubiquitously expressed and is localized to the golgi, where it recognizes the consensus sequence $RX_1X_2R$ (SEQ ID NO: 50), wherein $X_1$ is any amino acid, and $X_2$ is Lys or Arg, and cleaves after the final Arg. Furin plays a biological role in cleaving propeptides of proteins that are trafficked through the golgi. Accordingly, in certain embodiments the proteolytic cleavage site is a furin cleavage site comprising the sequence $RX_1X_2R$ (SEQ ID NO: 50), wherein $X_1$ is any amino acid, and $X_2$ is Lys or Arg, e.g., a furin cleavage site comprising the sequence RAKR (SEQ ID NO: 51).

In certain embodiments, the Ig Fc, Ig hinge region, and Ig CH1 domain are derived from a single immunoglobulin.

In certain embodiments, the fusion protein comprises an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 62, and SEQ ID NO: 63. In certain embodiments, a disclosed fusion protein comprises an amino acid sequence having greater than 80%, 85%, 90%, 95%, 96%, 97%, 98% or 99% sequence identity to a sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 62, and SEQ ID NO: 63.

Sequence identity may be determined in various ways that are within the skill in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) PROC. NATL. ACAD. SCI. USA 87:2264-2268; Altschul, (1993) J. MOL. EVOL. 36, 290-300; Altschul et al., (1997) NUCLEIC ACIDS RES. 25:3389-3402, incorporated by reference) are tailored for sequence similarity searching. For a discussion of basic issues in searching sequence databases see Altschul et al., (1994) NATURE GENETICS 6:119-129, which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) PROC. NATL. ACAD. SCI. USA 89:10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: -G, Cost to open gap [Integer]: default=5 for nucleotides/11 for proteins; -E, Cost to extend gap [Integer]: default=2 for nucleotides/1 for proteins; -q, Penalty for nucleotide mismatch [Integer]: default=−3; -r, reward for nucleotide match [Integer]: default=1; -e, expect value [Real]: default=10; -W, wordsize [Integer]: default=11 for nucleotides/28 for megablast/3 for proteins; -y, Dropoff (X) for blast extensions in bits: default=20 for blastn/7 for others; -X, X dropoff value for gapped alignment (in bits): default=15 for all programs, not applicable to blastn; and -Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In one aspect the invention provides a cytokine binding protein comprising two fusion proteins, wherein each fusion protein comprises in an N- to C-terminal orientation: a soluble portion of an extracellular domain of a cytokine receptor; an amino acid linker; an immunoglobulin (Ig) hinge region; and an immunoglobulin (Ig) Fc domain; wherein the linker comprises from about 5 to about 40 amino acid residues, wherein the two fusion proteins are covalently linked together, and wherein the two extracellular domains together define a binding site for a cytokine.

The cytokine binding protein may comprise two of the foregoing fusion proteins covalently linked together, wherein each fusion protein comprises an extracellular domain of a cytokine receptor, and wherein the two extracellular domains together define a binding site for a cytokine. The fusion proteins may be covalently linked, e.g., by disulfide bonds between cysteine residues in the Ig hinge region of each fusion protein. In certain embodiments, the fusion proteins, either monomeric or multimeric (e.g., dimeric) retain at least 50%, 60%, 70%, 80%, 90%, or 95% of the binding activity of the target ligand when compared to the native, full length cytokine receptor.

In certain embodiments, a cytokine binding protein of the invention binds a cytokine with a $K_D$ of 200 nM, 100 nM, 20 nM, 15 nM, 10 nM, 9 nM, 8 nM, 7 nM, 6 nM, 5 nM, 4 nM, 3 nM, 2 nM, 1 nM, 50 pM, 25 pM or lower. In certain embodiments, a cytokine binding protein of the invention binds a cytokine with a $K_D$ of from 200 nM to 100 nM, from 200 nM to 20 nM, from 200 nM to 10 nM, from 200 nM to 5 nM, from 200 nM to 1 nM, from 200 nM to 50 pM, from 200 nM to 25 pM, from 100 nM to 20 nM, from 100 nM to 10 nM, from 100 nM to 5 nM, from 100 nM to 1 nM, from 100 nM to 50 pM, from 100 nM to 25 pM, from 20 nM to 10 nM, from 20 nM to 5 nM, from 20 nM to 1 nM, from 20 nM to 50 pM, from 20 nM to 25 pM, from 10 nM to 5 nM, from 10 nM to 1 nM, from 10 nM to 50 pM, from 10 nM to 25 pM, from 5 nM to 1 nM, from 5 nM to 50 pM, from 5 nM to 25 pM, from 1 nM to 50 pM, from 1 nM to 25 pM, or from 50 pM to 25 pM. In certain embodiments, a cytokine binding protein of the invention binds TGFβ with a $K_D$ of 200 nM, 100 nM, 20 nM, 15 nM, 10 nM, 9 nM, 8 nM, 7 nM, 6 nM, 5 nM, 4 nM, 3 nM, 2 nM, 1 nM, 50 pM, 25 pM or lower. In certain embodiments, a cytokine binding protein of the invention binds TGFβ with a $K_D$ of from 200 nM to 100 nM, from 200 nM to 20 nM, from 200 nM to 10 nM, from 200 nM to 5 nM, from 200 nM to 1 nM, from 200 nM to 50 pM, from 200 nM to 25 pM, from 100 nM to 20 nM, from 100 nM to 10 nM, from 100 nM to 5 nM, from 100 nM to 1 nM, from 100 nM to 50 pM, from 100 nM to 25 pM, 20 nM to 10 nM, from 20 nM to 5 nM, from 20 nM to 1 nM, from 20 nM to 50 pM, from 20 nM to 25 pM, from 10 nM to 5 nM, from 10 nM to 1 nM, from 10 nM to 50 pM, from 10 nM to 25 pM, from 5 nM to 1 nM, from 5 nM to 50 pM, from 5 nM to 25 pM, from 1 nM to 50 pM, from 1 nM to 25 pM, or from 50 pM to 25 pM. $K_D$ values may be determined by methods well known in the art, including surface plasmon resonance or bio-layer interferometry methods.

Exemplary fusion proteins of the invention include proteins comprising an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 62, and SEQ ID NO: 63. For clarity, the sequences of the individual elements of these proteins, and the proteins from which the sequences of the individual elements were derived, including the soluble portion of an extracellular domain of a cytokine receptor, the amino acid linker, the Ig hinge region, and the Ig Fc domain, are set forth in TABLE 1.

TABLE 1

| Protein | Receptor Source Receptor SEQ ID | Linker Source Linker SEQ ID | Ig Hinge/Ig Fc Source Ig Hinge/Ig Fc SEQ ID |
| --- | --- | --- | --- |
| SEQ ID NO: 22 | TGFβIIR SEQ ID NO: 12 | IgG1 CH1 domain SEQ ID NO: 1 | IgG1 SEQ ID NO: 13 |
| SEQ ID NO: 62 | TGFβIIR SEQ ID NO: 12 | IgG1 CH1 domain SEQ ID NO: 60 | IgG1 SEQ ID NO: 13 |
| SEQ ID NO: 63 | TGFβIIR SEQ ID NO: 12 | IgG1 CH1 domain SEQ ID NO: 61 | IgG1 SEQ ID NO: 13 |
| SEQ ID NO: 23 | TGFβIIR SEQ ID NO: 12 | IgG2 CH1 domain SEQ ID NO: 2 | IgG2 SEQ ID NO: 14 |
| SEQ ID NO: 24 | TGFβIIR SEQ ID NO: 12 | IgG3 CH1 domain SEQ ID NO: 3 | IgG3 SEQ ID NO: 15 |
| SEQ ID NO: 25 | TGFβIIR SEQ ID NO: 12 | IgG4 CH1 domain SEQ ID NO: 4 | IgG4 SEQ ID NO: 16 |
| SEQ ID NO: 26 | TGFβIIR SEQ ID NO: 12 | IgA1 CH1 domain SEQ ID NO: 5 | IgA1 SEQ ID NO: 17 |
| SEQ ID NO: 27 | TGFβIIR SEQ ID NO: 12 | IgA2 CH1 domain SEQ ID NO: 6 | IgA2 SEQ ID NO: 18 |
| SEQ ID NO: 28 | TGFβIIR SEQ ID NO: 12 | IgD CH1 domain SEQ ID NO: 7 | IgD SEQ ID NO: 19 |
| SEQ ID NO: 29 | TGFβIIR SEQ ID NO: 12 | IgE CH1 domain SEQ ID NO: 8 | IgE SEQ ID NO: 20 |
| SEQ ID NO: 30 | TGFβIIR SEQ ID NO: 12 | IgM CH1 domain SEQ ID NO: 9 | IgM SEQ ID NO: 21 |
| SEQ ID NO: 31 | TGFβIIR SEQ ID NO: 12 | Albumin SEQ ID NO: 10 | IgG1 SEQ ID NO: 13 |
| SEQ ID NO: 32 | TGFβIIR SEQ ID NO: 12 | Casein SEQ ID NO: 11 | IgG1 SEQ ID NO: 13 |
| SEQ ID NO: 33 | mTGFβIIR SEQ ID NO: 34 | mIgG1 CH1 domain SEQ ID NO: 35 | mIgG1 SEQ ID NO: 36 |

TABLE 2

| Protein Sequence | Nucleic Acid Sequence |
|---|---|
| SEQ ID NO: 22 | SEQ ID NO: 37 |
| SEQ ID NO: 23 | SEQ ID NO: 38 |
| SEQ ID NO: 24 | SEQ ID NO: 39 |
| SEQ ID NO: 25 | SEQ ID NO: 40 |
| SEQ ID NO: 26 | SEQ ID NO: 41 |
| SEQ ID NO: 27 | SEQ ID NO: 42 |
| SEQ ID NO: 28 | SEQ ID NO: 43 |
| SEQ ID NO: 29 | SEQ ID NO: 44 |
| SEQ ID NO: 30 | SEQ ID NO: 45 |
| SEQ ID NO: 31 | SEQ ID NO: 46 |
| SEQ ID NO: 32 | SEQ ID NO: 47 |

II. Fusion Protein Production

Methods for producing fusion proteins of the invention are known in the art. For example, DNA molecules encoding a disclosed fusion protein can be chemically synthesized using the sequence information provided herein. Synthetic DNA molecules can be ligated to other appropriate nucleotide sequences, including, e.g., expression control sequences, to produce conventional gene expression constructs encoding the desired fusion protein. Production of defined gene constructs is within routine skill in the art. Exemplary nucleic acid sequences SEQ ID NOs: 37-47, which encode the fusion proteins of SEQ ID NOs: 22-32, can be found in TABLE 2.

Nucleic acids encoding desired fusion proteins can be incorporated (ligated) into expression vectors, which can be introduced into host cells through conventional transfection or transformation techniques. Exemplary host cells are *E. coli* cells, Chinese hamster ovary (CHO) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the desired fusion protein.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon, and, optionally, may contain enhancers, and various introns. The gene construct can be introduced into eukaryotic host cells using conventional techniques.

A polypeptide comprising a disclosed fusion protein can be produced by growing (culturing) a host cell transfected with an expression vector encoding such protein, under conditions that permit expression of the polypeptide. Following expression, the polypeptide can be harvested and purified or isolated using techniques known in the art, e.g., affinity tags such as Protein A, Protein G, glutathione-S-transferase (GST) and histidine tags.

III. Viral Vectors

In certain embodiments, a disclosed expression vector is a viral vector. The terms "viral vector" and "virus" are used interchangeably herein to refer to any of the obligate intracellular parasites having no protein-synthesizing or energy-generating mechanism. The viral genome may be RNA or DNA. The viruses useful in the practice of the present invention include recombinantly modified enveloped or non-enveloped DNA and RNA viruses, preferably selected from baculoviridiae, parvoviridiae, picornoviridiae, herpesviridiae, poxyiridae, or adenoviridiae. The viruses may be modified by recombinant DNA techniques to include expression of exogenous transgenes and may be engineered to be replication deficient, conditionally replicating, or replication competent. Chimeric viral vectors which exploit advantageous elements of each of the parent vector properties (See, e.g., Feng et al. (1997) NATURE BIOTECHNOLOGY 15:866-870) may also be useful in the practice of the present invention. Although it is generally favored to employ a virus from the species to be treated, in some instances it may be advantageous to use vectors derived from different species that possess favorable pathogenic features. For example, equine herpes virus vectors for human gene therapy are described in PCT Publication No. WO 98/27216. The vectors are described as useful for the treatment of humans as the equine virus is not pathogenic to humans. Similarly, ovine adenoviral vectors may be used in human gene therapy as they are claimed to avoid the antibodies against the human adenoviral vectors. Such vectors are described in PCT Publication No. WO 97/06826.

In certain embodiments, the viral vector is an oncolytic virus, e.g., a virus that exhibits tumor-selective replication and/or viral mediated lysis. In certain embodiments, the oncolytic virus allows for selective expression of a disclosed fusion protein, e.g., the virus permits expression of the fusion protein in neoplastic cells, but attenuates expression in normal cells. In certain embodiments, the expression of the fusion protein in a non-hyperproliferative cell is about 90%, about 80%, about 70%, about 60%, about 50%, about 40%, about 30%, about 20%, about 10%, or about 5% of the expression of in a hyperproliferative cell. In certain embodiments, the virus exhibits no detectable expression of the fusion protein in a non-hyperproliferative cell. Fusion protein expression may be determined by any appropriate method known in the art, e.g., Western blot or ELISA. The hyperproliferative cell may be a cancer cell, e.g., a carcinoma, sarcoma, leukemia, lymphoma, prostate cancer, lung cancer, gastrointestinal tract cancer, colorectal cancer, pancreatic cancer, breast cancer, ovarian cancer, cervical cancer, stomach cancer, thyroid cancer, mesothelioma, liver cancer, kidney cancer, skin cancer, head and neck cancer, or brain cancer cell.

Preferably, the viral vector is an adenovirus. Adenoviruses are medium-sized (90-100 nm), non-enveloped (naked), icosahedral viruses composed of a nucleocapsid and a double-stranded linear DNA genome. Adenoviruses replicate in the nucleus of mammalian cells using the host's replication machinery. The term "adenovirus" refers to any virus in the genus Adenoviridiae including, but not limited to, human, bovine, ovine, equine, canine, porcine, murine, and simian adenovirus subgenera. In particular, human adenoviruses includes the A-F subgenera as well as the individual serotypes thereof, the individual serotypes and A-F subgenera including but not limited to human adenovirus types 1, 2, 3, 4, 4a, 5, 6, 7, 8, 9, 10, 11 (Ad11a and Ad11p), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. Preferred are vectors derived from human adenovirus types 2 and 5. Unless stated otherwise, all adenovirus type 5 nucleotide numbers are relative to the NCBI reference sequence AC_000008.1, which is depicted herein in SEQ ID NO: 52.

The adenovirus replication cycle has two phases: an early phase, during which 4 transcription units (E1, E2, E3, and E4) are expressed, and a late phase which occurs after the onset of viral DNA synthesis, and during which late transcripts are expressed primarily from the major late promoter (MLP). The late messages encode most of the virus's structural proteins. The gene products of E1, E2 and E4 are responsible for transcriptional activation, cell transformation, viral DNA replication, as well as other viral functions, and are necessary for viral growth.

The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a gene if it affects the transcription of the gene. Operably linked nucleotide sequences are typically contiguous. However, as enhancers generally function when separated from the promoter by several kilobases and intronic sequences may be of variable lengths, some polynucleotide elements may be operably linked but not directly flanked and may even function in trans from a different allele or chromosome.

In certain embodiments, the virus has one or more modifications to a regulatory sequence or promoter. A modification to a regulatory sequence or promoter comprises a deletion, substitution, or addition of one or more nucleotides compared to the wild-type sequence of the regulatory sequence or promoter.

In certain embodiments, the modification of a regulatory sequence or promoter comprises a modification of a sequence of a transcription factor binding site to reduce affinity for the transcription factor, for example, by deleting a portion thereof, or by inserting a single point mutation into the binding site. In certain embodiments, the additional modified regulatory sequence enhances expression in neoplastic cells, but attenuates expression in normal cells.

In certain embodiments, the modified regulatory sequence is operably linked to a sequence encoding a protein. In certain embodiments, at least one of the adenoviral E1a and E1b genes (coding regions) is operably linked to a modified regulatory sequence. In certain embodiments, the E1a gene is operably linked to the modified regulatory sequence.

The E1a regulatory sequence contains five binding sites for the transcription factor Pea3, designated Pea3 I, Pea3 II, Pea3 III, Pea3 IV, and Pea3 V, where Pea3 I is the Pea3 binding site most proximal to the E1a start site, and Pea3 V is most distal. The E1a regulatory sequence also contains binding sites for the transcription factor E2F, hereby designated E2F I and E2F II, where E2F I is the E2F binding site most proximal to the E1a start site, and E2F II is more distal. From the E1a start site, the binding sites are arranged: Pea3 I, E2F I, Pea3 II, E2F II, Pea3 III, Pea3 IV, and Pea3 V.

In certain embodiments, at least one of these seven binding sites, or a functional portion thereof, is deleted. A "functional portion" is a portion of the binding site that, when deleted, decreases or even eliminates the functionality, e.g. binding affinity, of the binding site to its respective transcription factor (Pea3 or E2F) by, for example, at least 40%, 50%, 60%, 70%, 80%, 90%, 95% or 100% relative to the complete sequence. In certain embodiments, one or more entire binding sites are deleted. In certain embodiments, a functional portion of one or more binding sites is deleted. A "deleted binding site" encompasses both the deletion of an entire binding site and the deletion of a functional portion thereof. When two or more binding sites are deleted, any combination of entire binding site deletion and functional portion deletion may be used.

In certain embodiments, at least one Pea3 binding site, or a functional portion thereof, is deleted. The deleted Pea3 binding site can be Pea3 I, Pea3 II, Pea3 III, Pea3 IV, and/or Pea3 V. In certain embodiments, the deleted Pea3 binding site is Pea3 II, Pea3 III, Pea3 IV, and/or Pea3 V. In certain embodiments, the deleted Pea3 binding site is Pea3 IV and/or Pea3 V. In certain embodiments, the deleted Pea3 binding site is Pea3 II and/or Pea3 III. In certain embodiments, the deleted Pea3 binding site is both Pea3 II and Pea3 III. In certain embodiments, the Pea3 I binding site, or a functional portion thereof, is retained.

In certain embodiments, at least one E2F binding site, or a functional portion thereof, is deleted. In certain embodiments, at least one E2F binding site, or a functional portion thereof, is retained. In certain embodiments, the retained E2F binding site is E2F I and/or E2F II. In certain embodiments, the retained E2F binding site is E2F II. In certain embodiments, the total deletion consists essentially of one or more of Pea3 II, Pea3 III, Pea3 IV, and/or Pea3 V, or functional portions thereof.

In certain embodiments, the virus has a deletion of a 50 base pair region located from −305 to −255 upstream of the E1a initiation site, e.g., corresponding to 195-244 of the Ad5 genome (SEQ ID NO: 52), hereafter referred to as the TAV-255 deletion. In certain embodiments, the TAV-255 deletion results in an E1a promoter that comprises the sequence GGTGTTTTGG (SEQ ID NO: 55).

The adenoviral E1b-19k gene functions primarily as an anti-apoptotic gene and is a homolog of the cellular anti-apoptotic gene, BCL-2. Since host cell death prior to maturation of the progeny viral particles would restrict viral replication, E1b-19k is expressed as part of the E1 cassette to prevent premature cell death thereby allowing the infection to proceed and yield mature virions. Accordingly, in certain embodiments, a recombinant virus is provided that includes an E1b-19K insertion site, e.g., the adenovirus has an exogenous nucleotide sequence encoding a disclosed fusion protein inserted into an E1b-19K insertion site.

In certain embodiments, the E1b-19K insertion site is located between the start site of E1b-19K (i.e., the nucleotide sequence encoding the start codon of E1b-19k, e.g., corresponding to nucleotides 1714-1716 of SEQ ID NO: 52) and the start site of E1b-55K (i.e., the nucleotide sequence encoding the start codon of E1b-55k, e.g., corresponding to nucleotides 2019-2021 of SEQ ID NO: 52). Throughout the description and claims, an insertion between two sites, for example, an insertion between (i) a start site of a first gene (e.g., E1b-19k) and a start site of a second gene, (e.g., E1b-55K), (ii) a start site of a first gene and a stop site of a second gene, (iii) a stop site of a first gene and start site of a second gene, or (iv) a stop site of first gene and a stop site of a second gene, is understood to mean that all or a portion of the nucleotides constituting a given start site or a stop site surrounding the insertion may be present or absent in the final virus. Similarly, an insertion between two nucleotides is understood to mean that the nucleotides surrounding the insertion may be present or absent in the final virus.

In certain embodiments, the E1b-19K insertion site is located between the start site of E1b-19K (i.e., the nucleotide sequence encoding the start codon of E1b-19k, e.g., corresponding to nucleotides 1714-1716 of SEQ ID NO: 52) and the stop site of E1b-19K (i.e., the nucleotide sequence encoding the stop codon of E1b-19k, e.g., corresponding to nucleotides 2242-2244 of SEQ ID NO: 52). In certain embodiments, the E1b-19K insertion site comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent the start site of E1b-19K. In certain embodiments, the E1b-19K insertion site comprises a deletion of about 200 nucleotides, e.g., 203 nucleotides adjacent the start site of E1b-19K. In certain embodiments, the E1b-19K insertion site comprises a deletion corresponding to nucleotides 1714-1916 of the Ad5 genome (SEQ ID NO: 52), or the exogenous nucleotide sequence is inserted between nucleotides corresponding to 1714 and 1916 of the Ad5 genome (SEQ ID NO: 52). In certain embodiments, the exogenous nucleotide sequence is inserted between CTGACCTC (SEQ ID NO: 53) and TCACCAGG (SEQ ID NO: 54), e.g., the recombinant adenovirus comprises, in a 5' to 3' orientation, CTGACCTC (SEQ ID NO: 53), the exogenous nucleotide sequence, and TCACCAGG (SEQ ID NO: 54). CTGACCTC (SEQ ID NO: 53) and TCACCAGG (SEQ ID NO: 54) define unique boundary sequences for the E1b-19K insertion site within the Ad5 genome (SEQ ID NO: 52). Throughout the description and claims, a deletion adjacent to a site, for example, a deletion adjacent to a start site of a gene or a deletion adjacent to a stop site of a gene, is understood to mean that the deletion may include a deletion of all, a portion, or none of the nucleotides constituting a given start site or a stop site.

In certain embodiments the recombinant adenovirus comprises an E3 deletion. In certain embodiments, the E3 deletion comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or from about 3000 to about 3185 nucleotides.

In certain embodiments, the E3 deletion comprises a deletion located between the stop site of pVIII (i.e., the nucleotide sequence encoding the stop codon of pVIII, e.g., corresponding to nucleotides 27855-27857 of SEQ ID NO: 52) and the start site of Fiber (i.e., the nucleotide sequence encoding the start codon of Fiber, e.g., corresponding to nucleotides 31042-31044 of SEQ ID NO: 52). In certain embodiments, the E3 deletion comprises a deletion located between the stop site of E3-10.5K (i.e., the nucleotide sequence encoding the stop codon of E3-10.5K, e.g., corresponding to nucleotides 29770-29772 of SEQ ID NO: 52) and the stop site of E3-14.7K (i.e., the nucleotide sequence encoding the stop codon of E3-14.7K, e.g., corresponding to nucleotides 30837-30839 of SEQ ID NO: 52). In certain embodiments, the E3 deletion comprises a deletion of from about 500 to about 1551, from about 500 to about 1500, from about 500 to about 1000, from about 1000 to about 1551, from about 1000 to about 1500, or from about 1500 to about 1551 nucleotides adjacent to the stop site of E3-10.5K. In certain embodiments, the E3 deletion comprises a deletion of about 1050 nucleotides adjacent to the stop site of E3-10.5K (i.e., the nucleotide sequence encoding the stop codon of E3-10.5K, e.g., corresponding to nucleotides 29770-29772 of SEQ ID NO: 52), e.g., the E3 deletion comprises a deletion of 1064 nucleotides adjacent to the stop site of E3-10.5K. In certain embodiments, the E3 deletion comprises a deletion corresponding to the Ad5 dl309 E3 deletion. In certain embodiments, the E3 deletion comprises a deletion corresponding to nucleotides 29773-30836 of the Ad5 genome (SEQ ID NO: 52).

In certain embodiments, the E3 deletion comprises a deletion located between the stop site of E3-gp19K (i.e., the nucleotide sequence encoding the stop codon of E3-gp19K, e.g., corresponding to nucleotides 29215-29217 of SEQ ID NO: 52) and the stop site of E3-14.7K (i.e., the nucleotide sequence encoding the stop codon of E3-14.7K, e.g., corresponding to nucleotides 30837-30839 of SEQ ID NO: 52). In certain embodiments, the E3 deletion comprises a deletion of from about 500 to about 1824, from about 500 to about 1500, from about 500 to about 1000, from about 1000 to about 1824, from about 1000 to about 1500, or from about 1500 to about 1824 nucleotides adjacent the stop site of E3-gp19K. In certain embodiments, the E3 deletion comprises a deletion of about 1600 nucleotides adjacent the stop site of E3-gp19K. e.g., the E3 insertion site comprises a deletion of 1622 nucleotides adjacent the stop site of E3-gp19K. In certain embodiments, the E3 deletion comprises a deletion corresponding to nucleotides 29218-30839 of the Ad5 genome (SEQ ID NO: 52).

In certain embodiments, the recombinant adenovirus comprises an E3 insertion site, e.g., the adenovirus has an exogenous nucleotide sequence encoding a disclosed fusion protein inserted into the E3 deletion. For example, in certain embodiments, an exogenous nucleotide sequence is inserted between nucleotides corresponding to 29773 and 30836 of the Ad5 genome (SEQ ID NO: 52). In certain embodiments, the exogenous nucleotide sequence is inserted between CAGTATGA (SEQ ID NO: 56) and TAATAAAAAA (SEQ ID NO: 57), e.g., the recombinant adenovirus comprises, in a 5' to 3' orientation, CAGTATGA (SEQ ID NO: 56), the exogenous nucleotide sequence, and TAATAAAAAA (SEQ ID NO: 57). CAGTATGA (SEQ ID NO: 56) and TAATAAAAAA (SEQ ID NO: 57) define unique boundary sequences for an E3 insertion site within the Ad5 genome (SEQ ID NO: 52).

In certain embodiments, the exogenous nucleotide sequence is inserted between nucleotides corresponding to 29218 and 30839 of the Ad5 genome (SEQ ID NO: 52). In certain embodiments, the exogenous nucleotide sequence is inserted between TGCCTTAA (SEQ ID NO: 58) and TAAAAAAAAAT (SEQ ID NO: 59), e.g., the recombinant adenovirus comprises, in a 5' to 3' orientation, TGCCTTAA (SEQ ID NO: 58), the exogenous nucleotide sequence, and TAAAAAAAAAT (SEQ ID NO: 59). TGCCTTAA (SEQ ID NO: 58) and TAAAAAAAAAT (SEQ ID NO: 59) define unique boundary sequences for an E3 insertion site within the Ad5 genome (SEQ ID NO: 52).

Additional exemplary adenovirus vectors useful in the practice of this aspect of the invention are described in U.S. Pat. No. 9,073,980.

IV. Fusion Protein Modifications

When used as a therapeutic, a fusion protein may be optimized (e.g., affinity-matured) to improve biochemical characteristics including affinity and/or specificity, improve biophysical properties including aggregation, stability, precipitation and/or non-specific interactions, and/or to reduce immunogenicity. Affinity-maturation procedures are within ordinary skill in the art. For example, diversity can be introduced into a disclosed fusion protein by DNA shuffling, chain shuffling, CDR shuffling, random mutagenesis and/or site-specific mutagenesis.

Generally, an optimized fusion protein has at least the same, or substantially the same (e.g., at least 85%, 90%, 95%, 96%, 97%, 98%, or 99%) affinity for a ligand as the non-optimized (or parental) fusion protein from which it was derived. Preferably, an optimized fusion protein has a higher affinity for a ligand when compared to a parental fusion protein.

Fusion proteins (e.g., parental and optimized variants) can be engineered to contain certain constant (i.e., Fc) regions with a specified effector function (e.g., antibody-dependent cellular cytotoxicity (ADCC)). Human constant regions are known in the art.

Furthermore, if the fusion protein is for use as a therapeutic, it can be conjugated to an effector agent such as a small molecule toxin or a radionuclide using standard in vitro conjugation chemistries. If the effector agent is a polypeptide, the antibody can be chemically conjugated to the effector or joined to the effector as a fusion protein. Construction of fusion proteins is within ordinary skill in the art.

V. Methods of Treatment

The foregoing fusion proteins or expression vectors can be used to treat various medical indications. In certain embodiments, the foregoing fusion proteins or expression vectors can be used to treat medical indications that are mediated by a cytokine, for example TGFβ. For example, the fusion proteins and expression vectors can be used to treat various cancers or inflammatory diseases.

As used herein, "treat," "treating" and "treatment" mean the treatment of a disease in a subject, e.g., in a mammal, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

In certain embodiments, the fusion proteins and expression vectors disclosed herein can be used to treat various cancers. The cancer cells are exposed to a therapeutically effective amount of the fusion protein or expression vector so as to inhibit or reduce proliferation of the cancer cells. In certain embodiments, administering a therapeutically effective amount of a fusion protein or expression vector to cancer cells reduces TGFβ in the cells by at least 30%, at least 40%, at least 50%, at least 60%, at least 70%, at least 80%, at least 90%, or at least 95%. TGFβ activity may be assayed by Western blot as described in Example 2. In some embodiments, a disclosed fusion protein or expression vector can be used to inhibit tumor growth in a subject (e.g., a human patient, also referred to as a human subject), which can be accomplished by administering an effective amount of the fusion protein or expression vector to the subject. In certain embodiments, administering an effective amount of a fusion protein or expression vector to a subject reduces tumor load in that subject by at least 30%, at least 40%, at least 50%, at least 60%, at least 70%, at least 80%, or at least 90%.

Examples of cancers include solid tumors, soft tissue tumors, hematopoietic tumors and metastatic lesions. Examples of hematopoietic tumors include, leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), e.g., transformed CLL, diffuse large B-cell lymphomas (DLBCL), follicular lymphoma, hairy cell leukemia, myelodyplastic syndrome (MDS), a lymphoma, Hodgkin's disease, a malignant lymphoma, non-Hodgkin's lymphoma, Burkitt's lymphoma, multiple myeloma, or Richter's Syndrome (Richter's Transformation). Examples of solid tumors include malignancies, e.g., sarcomas, adenocarcinomas, and carcinomas, of the various organ systems, such as those affecting head and neck (including pharynx), thyroid, lung (small cell or non-small cell lung carcinoma (NSCLC)), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), or skin (e.g., melanoma).

In certain embodiments, the cancer is selected from melanoma, squamous cell carcinoma of the skin, basal cell carcinoma, head and neck cancer, breast cancer, anal cancer, cervical cancer, non-small cell lung cancer, mesothelioma, small cell lung cancer, renal cell carcinoma, prostate cancer, gastroesophageal cancer, colorectal cancer, testicular cancer, bladder cancer, ovarian cancer, liver cancer, hepatocellular carcinoma, cholangiocarcinoma, brain and central nervous system cancer, thyroid cancer, parathyroid cancer (e.g., parathyroid carcinoma), endometrial cancer, neuroendocrine cancer, lymphoma (e.g., Hodgkin and non-Hodgkin), leukemia, merkel cell carcinoma, gastrointestinal stromal tumors, multiple myeloma, uterine cancer, a sarcoma, kidney cancer, ocular cancer, pancreatic cancer, and a germ cell cancer (e.g., ovarian germ cell cancer). In certain embodiments, the cancer may be selected from leukemia, breast cancer, lung cancer, pancreatic cancer, endometrial cancer, ovarian cancer, prostate cancer, cervical cancer, brain cancer, skin cancer, colorectal cancer, gastric cancer, head and neck cancer, and leukemia. In certain embodiments, the cancer is selected from leukemia, breast cancer, cervical cancer, colorectal cancer, lung cancer, pancreatic cancer, prostate cancer, gastric cancer, head and neck cancer, endometrial cancer and ovarian cancer.

In certain embodiments, a fusion protein or expression vector of the disclosure is administered to decrease levels of one or more cytokines in a subject in need thereof (e.g., a subject with an inflammatory condition). In certain embodiments, a disclosed fusion protein or expression vector can be used to treat an inflammatory condition in a subject (e.g., a human subject), which can be accomplished by administering an effective amount of the fusion protein or expression vector to the subject.

As used herein, an inflammatory condition is a disease or condition characterized, in whole or in part, by inflammation or an inflammatory response in the patient. Inflammatory conditions treatable using the fusion proteins or expression vectors of the invention may be characterized, for example, based on the primary tissue affected, the mechanism of action underlying the condition, or the portion of the immune system that is misregulated or overactive. In certain embodiments, examples of inflammatory conditions that may be treated include inflammation of the lungs (e.g., asthma, adult respiratory distress syndrome, bronchitis, pulmonary inflammation, pulmonary fibrosis, and cystic fibrosis), joints (e.g., rheumatoid arthritis, rheumatoid spondylitis, juvenile rheumatoid arthritis, osteoarthritis, gouty arthritis and other arthritic conditions), connective tissue, eyes (e.g., uveitis (including iritis), conjunctivitis, scleritis, and keratoconjunctivitis sicca), nose, bowel (e.g., Crohn's disease, ulcerative colitis, inflammatory bowel disease, inflammatory bowel syndrome, and distal proctitis), kidney (e.g., glomerulonephritis, interstitial nephritis, lupus nephritis, nephritis secondary to Wegener's disease, acute renal failure secondary to acute nephritis, Goodpasture's syndrome, post-obstructive syndrome and tubular ischemia), liver (e.g., hepatitis (arising from viral infection, autoimmune responses, drug treatments, toxins, environmental agents, or as a secondary consequence of a primary disorder), obesity, biliary atresia, primary biliary cirrhosis and primary sclerosing cholangitis), skin (e.g., psoriasis, eczema, and dermatitis, e.g., eczematous dermatitides, topic and seborrheic dermatitis, allergic or irritant contact dermatitis, eczema craquelee, photoallergic dermatitis, phototoxicdermatitis, phytophotodermatitis, radiation dermatitis, and stasis dermatitis), central nervous system (e.g., multiple sclerosis and neurodegenerative diseases such as Alzheimer's disease, Parkinson's disease or dementia associated with HIV infection), vascular system (e.g. coronary infarct damage, peripheral vascular disease, myocarditis, vasculitis, revascularization of stenosis, atherosclerosis, and vascular disease associated with Type II diabetes), endocrine system (e.g., autoimmune thyroiditis (Hashimoto's disease), Type I diabetes, inflammation in liver and adipose tissue associated with Type II diabetes, and acute and chronic inflammation of the adrenal cortex) heart, or adipose tissue. The disclosure contemplates that some inflammatory conditions involve inflammation in multiple tissues. Moreover, the disclosure contemplates that some inflammatory conditions may fall into multiple categories. In certain embodiments, the inflammatory condition is an autoimmune disease. Exemplary autoimmune diseases include, but are not limited to, rheumatoid arthritis, psoriasis (including plaque psoriasis), psoriatic arthritis, ankylosing spondylitis, ulcerative colitis, multiple sclerosis, lupus, alopecia, autoimmune pancreatitis, Celiac disease, Behcet's disease, Cushing syndrome, and Grave's disease. In certain embodiments, the inflammatory condition is a rheumatoid disorder. Exemplary rheumatoid disorders include, but are not limited to, rheumatoid arthritis, juvenile arthritis, bursitis, spondylitis, gout, scleroderma, Still's disease, and vasculitis. It is noted that certain categories of conditions overlap. For example, rheumatoid arthritis is an inflammatory rheumatoid disorder, an inflammatory joint disorder, and an autoimmune disorder.

The term "effective amount" as used herein refers to the amount of an active component (e.g., the amount of a fusion protein or expression vector of the present invention) sufficient to effect beneficial or desired results. An effective amount can be administered in one or more administrations, applications or dosages and is not intended to be limited to a particular formulation or administration route.

In certain embodiments, a therapeutically effective amount of a fusion protein is in the range of 0.1 mg/kg to 100 mg/kg, e.g., 1 mg/kg to 100 mg/kg, 1 mg/kg to 10 mg/kg, 1 mg/kg to 5 mg/kg, 10 mg/kg, 7.5 mg/kg, 5 mg/kg, or 2.5 mg/kg. In certain embodiments, a therapeutically effective amount of an expression vector, e.g., a recombinant virus, is in the range of $10^2$ to $10^{15}$ plaque forming units (pfus), e.g., $10^2$ to $10^{10}$, $10^2$ to $10^5$, $10^5$ to $10^{15}$, $10^5$ to $10^{10}$, or $10^{10}$ to $10^{15}$ plaque forming units. The amount administered will depend on variables such as the type and extent of disease or indication to be treated, the overall health of the patient, the in vivo potency of the fusion protein or expression vector, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment.

Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the antibody, and the disease being treated. Exemplary dosing frequencies are once per day, once per week and once every two weeks. A preferred route of administration is parenteral, e.g., intravenous infusion. Formulation of fusion protein- or expression vector-based drugs is within ordinary skill in the art. In some embodiments, a fusion protein or expression vector is lyophilized, and then reconstituted in buffered saline, at the time of administration.

For therapeutic use, a fusion protein or expression vector preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing fusion proteins or expression vectors disclosed herein can be presented in a dosage unit form and can be prepared by any suitable method. A pharmaceutical composition should be formulated to be compatible with its intended route of administration. Examples of routes of administration are intravenous (IV), intradermal, inhalation, intraocular, intranasal, transdermal, topical, transmucosal, and rectal administration.

A preferred route of administration for fusion proteins is IV infusion. Useful formulations can be prepared by methods known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution. In certain embodiments, a delivery vehicle (e.g., a recombinant virus) and/or a therapeutic agent of the invention is administered in combination with a checkpoint inhibitor, e.g., an anti-CTLA-4 antibody, an anti-PD-1 antibody, or an anti-PD-L1 antibody. Exemplary anti-PD-1 antibodies include, for example, nivolumab (Opdivo®, Bristol-Myers Squibb Co.), pembrolizumab (Keytruda®, Merck Sharp & Dohme Corp.), PDR001 (Novartis Pharmaceuticals), and pidilizumab (CT-011, Cure Tech). Exemplary anti-PD-L1 antibodies include, for example, atezolizumab (Tecentriq®, Genentech), duvalumab (AstraZeneca), MEDI4736, avelumab (Bavencio®, EMD Serono), and BMS 936559 (Bristol Myers Squibb Co.).

The term administered "in combination," as used herein, is understood to mean that two (or more) different treatments are delivered to the subject during the course of the subject's affliction with the disorder, such that the effects of the treatments on the subject overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Throughout the description, where compositions, devices, and systems are described as having, including, or comprising specific components, or where processes and methods are described as having, including, or comprising specific steps, it is contemplated that, additionally, there are compositions, devices, and systems of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular virus, that virus can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1: TGFβR Fusion Protein Plasmid and Adenovirus Construction

This Example describes the production of plasmids and viral expression vectors that encode TGFβR fusion proteins.

To construct a nucleotide sequence encoding a mouse TGFβR-IgG1 fusion protein (mTGFβR-IgG1), plasmids pORF9-mIL10RA, pUNO1-mTGFBR2, and pFUSEss-CHIg-mG1 were purchased from Invivogen. The pUNO1-mTGFBR2 plasmid was cleaved with KasI and NheI to release a 1.7 kb fragment with the coding region of the mouse TGFβ type 2 receptor. The pORF9-mIL10RA plasmid was cleaved with KasI and NheI to release a 3 kb fragment containing the vector backbone. Those two fragments were ligated to generate the plasmid pORF9-TGFBR2.

The plasmid pORF9-TGFBR2 was amplified with primers flanking the KasI site 5' of the coding region and either a primer corresponding to the 3' end of the extracellular domain followed by an NheI site to produce only the extracellular domain, or a primer corresponding to the 3' end of the extracellular domain followed by a portion of the mouse IgG1 (mIgG1) CH1 domain to produce the 5' half of a fusion gene. The plasmid pFUSEss-CHIg-mG1 was amplified with primers corresponding to the 3' end of the mIgG1 gene followed by a NheI site, and the 3' end of the extracellular domain of the mTGFβR followed by a portion of the mIgG1 CH1 domain. Fusion genes were generated by combining these PCR products in a second round PCR reaction. PCR products were then cleaved with KasI and NheI and ligated into a pORF9 backbone cleaved with the same enzymes to generate pORF9 plasmids carrying either the extracellular domain or the mIgG1 fusion genes. The resulting nucleotide sequence encoded a fusion protein (mTGFβR-IgG, SEQ ID NO: 33) including residues 1-159 of the mTGFβR sequence (ending in TSSPD) immediately followed by residues 90-324 of the mIgG1 sequence, starting at the beginning of the final β strand of the second immunoglobulin fold (beginning with STKVD).

To construct nucleotide sequences encoding human TGFβR-IgG1 fusion proteins, plasmids carrying cDNA of human IgG1 (hIgG1, Accession BC072419 in pCMV-SPORT6) and human TGFβ receptor type 2 (Accession BC040499 in pBluescriptR) were purchased from Thermo Scientific. PCR amplification using a 5' primer carrying a SalI site, a 3' primer carrying an XhoI site, and linking primers carrying a sequence from the 3' end of hTGFβR and the 5' end of hIgG1 was performed as described for the mouse genes.

Nucleotide sequences encoding a series of fusion proteins were generated. A first fusion protein, hTGFβR-IgG1-1 (SEQ ID NO: 22), included residues 1-159 of hTGFβR (ending in TSNPD), immediately followed by residues 88-330 of hIgG1, starting at the beginning of the final β strand of the second immunoglobulin fold (beginning at KPSNT). A second fusion protein, hTGFβR-IgG1-2 (SEQ ID NO: 62), included residues 1-159 of hTGFβR (ending in TSNPD), immediately followed by residues 90-330 of hIgG1 (beginning at SNTKV). A third fusion protein, hTGFβR-IgG1-3 (SEQ ID NO: 63), included residues 1-159 of hTGFβR (ending in TSNPD), immediately followed by residues 92-330 of hIgG1 (beginning at TKVDK). A fourth fusion protein, hTGFβR-IgG1-4, included residues 1-159 of hTGFβR (ending in TSNPD), immediately followed by residues 94-330 of hIgG1 (beginning at VDKRV). A fifth fusion protein, hTGFβR-Fc (SEQ ID NO: 48), included residues 1-159 of TGFβR (ending in TSNPD), immediately followed by residues 100-330 of hIgG1 (beginning at PKSCD). The fifth fusion protein was referred to as hTGFβR-Fc because it included only the Fc domain and hinge region of the immunoglobulin, in contrast to hTGFβR-IgG-1, hTGFβR-IgG-2, hTGFβR-IgG-3, and hTGFβR-IgG-4, which included from six to twelve additional amino acids from hIgG1. Details of the fusion proteins are shown in TABLE 3.

Nucleotide sequences encoding the fusion proteins were cloned into plasmids for downstream applications as appropriate. For adenovirus construction, nucleotide sequences were cloned into a derivative of pXC1 (which carries the 5' portion of the adenovirus genome), modified to carry a SalI site at the start site of the E1B-19k region and an XhoI site 200 base pairs 3' of the SalI site. When indicated, pXC1 was further modified at the E1A promoter region to produce the plasmid pXC1-TAV-255, which renders E1A expression cancer-selective (as previously described in U.S. Pat. No. 9,073,980). PCR products were cloned into the pXC1 (or pXC1-TAV) backbone using InFusion (Clontech) according to the manufacturer's instructions.

Where indicated, the pXC1 plasmids were cotransfected with the plasmid pJM17 in HEK-293A cells to allow homologous recombination to rescue recombinant virus. Virus was collected and underwent two rounds of plaque purification and sequencing to confirm presence of the fusion gene and test for presence of the TAV-255 deletion as necessary. The virus carrying the mouse isoform was grown in 293 cells, and the virus carrying the human isoform was plaque purified and grown exclusively in A549 cells after the initial viral rescue in 293 cells. Virus to be used in animal experiments was purified using Fast-Trap adenovirus purification kits (Millipore), dialyzed into viral storage buffer (25 mM NaCl, 10 mM Tris pH 8, 5% glycerol), and stored at −80° until use. Details of the viruses tested are shown in TABLE 4.

TABLE 4

| Virus | E1A Promoter | E1B-19k Modification |
|---|---|---|
| Wild-type | Wild-type | Wild-type |
| Ad-Control | Wild-type | Deleted |
| Ad-mTGFβR-IgG1 | Wild-type | Deleted and replaced with mTGFβR-IgG1 |
| Ad-hTGFβR-IgG1-1 | TAV-255 | Deleted and replaced with hTGFβR-IgG1-1 |

Example 2: Inhibition of TGFβ Signaling

This Example describes a comparison between disclosed hTGFβR-IgG1 fusion proteins and conventional hTGFβR-IgG1 fusion proteins.

As described in Example 1, plasmids were generating encoding a series of human TGFβ trap fusion proteins: hTGFβR-IgG1-1, hTGFβR-IgG1-2, hTGFβR-IgG1-3, hTGFβR-IgG1-4, and hTGFβR-Fc.

hTGFβR-Fc (SEQ ID NO: 48) contains amino acids Thr23 to Asp159 of the human TGFβ type II receptor and amino acids Pro100 to Lys330 of human IgG1. This

TABLE 3

| Fusion Protein | hTGFβR Residues | hIgG1 Residues | hTGFβR- hIgG1 Junction |
|---|---|---|---|
| hTGFβR-IgG1-1 | 1-159 | 88-330 | TSNPD-KPSNTKVDKRVEPKSCD |
| hTGFβR-IgG1-2 | 1-159 | 90-330 | TSNPD-SNTKVDKRVEPKSCD |
| hTGFβR-IgG1-3 | 1-159 | 92-330 | TSNPD-TKVDKRVEPKSCD |
| hTGFβR-IgG1-4 | 1-159 | 94-330 | TSNPD-VDKRVEPKSCD |
| hTGFβR-Fc | 1-159 | 100-330 | TSNPD-PKSCD | sequence is identical that used in a commercially available TGFβ trap fusion protein (R&D Systems).

In contrast to the conventional TGFβ trap fusion protein, hTGFβR-IgG1-1 (SEQ ID NO: 22), hTGFβR-IgG-2 (SEQ ID NO: 62), hTGFβR-IgG-3 (SEQ ID NO: 63), and hTGFβR-IgG-4, contain twelve, ten, eight, or six amino acids, respectively, from the CH1 domain of IgG1 that serve as a flexible, non-immunogenic linker between the TGFβ type II receptor and the hinge and Fc region of the IgG1.

HEK-293 cells were transfected with pXC1 plasmids carrying hTGFβR-IgG1-1, hTGFβR-IgG1-2, hTGFβR-IgG1-3, hTGFβR-IgG1-4, or hTGFβR-Fc genes, or were kept as non-transfected controls, and were incubated for five days to allow protein expression and secretion into the media. The conditioned media was collected, TGFβ was added to the media at 500 pg/ml where indicated, and the media was then overlaid on fresh reporter cells and incubated for one hour. Free TGFβ will induce Smad2 phosphorylation in the reporter cells, however, if the TGFβ trap fusion protein blocks TGFβ, then it will not lead to Smad2 phosphorylation. Protein extracts of the reporter cells were probed by Western blot for phosphorylated Smad2. B-actin was used as a loading control, or subsequently the blot was stripped and reprobed for total Smad2 and Smad3 to serve as a loading control.

Figure 3:
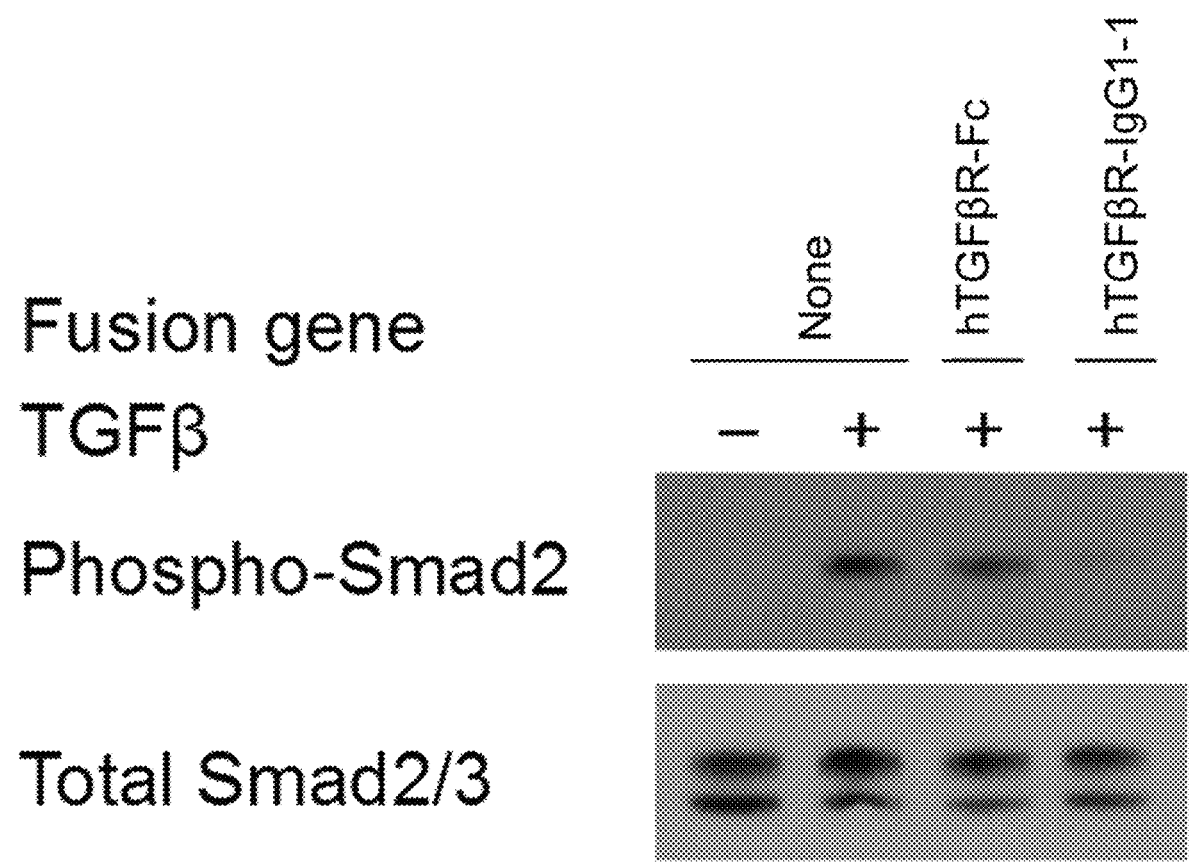
FIG. 3 depicts a Western blot for phosphorylated Smad2 following treatment of reporter cells with TGFβ and/or the TGFβ type II receptor fusion proteins hTGFβR-IgG-1 and hTGFβR-Fc as indicated. Total Smad2 and Smad3 were used as a loading control. TGFβ activity was markedly reduced by hTGFβR-IgG-1 compared to hTGFβR-Fc.

A comparison between hTGFβR-IgG1-1 and hTGFβR-Fc is shown in FIG. 3. As seen in FIG. 3, conditioned media from cells transfected with the conventional hTGFβR-Fc fusion gene has modest inhibition of TGFβ, while hTGFβR-IgG-1 more effectively blocked TGFβ signaling. Quantitation of the intensity of the Western blot shows that, compared to controls, hTGFβR-Fc resulted in a 21% reduction of TGFβ activity, and hTGFβR-IgG resulted in a 92% reduction of TGFβ activity.

Figure 4:
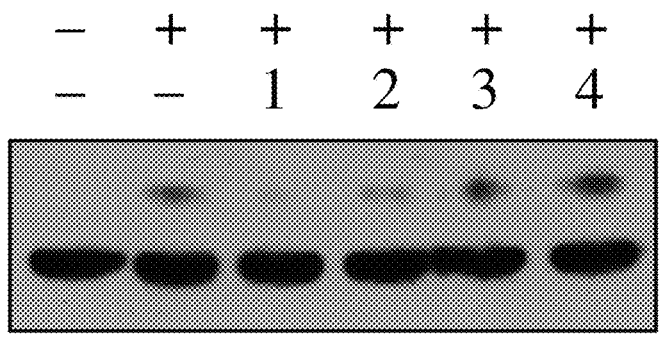
FIG. 4 depicts a Western blot for phosphorylated Smad2 following treatment of reporter cells with TGFβ and/or the TGFβ type II receptor fusion proteins hTGFβR-IgG1-1 (1), hTGFβR-IgG1-2 (2), hTGFβR-IgG1-3 (3), and hTGFβR-IgG1-4 (4) as indicated. B-actin was used as a loading control.

A comparison between hTGFβR-IgG1-1, hTGFβR-IgG1-2, hTGFβR-IgG1-3, and hTGFβR-IgG1-4 is shown in FIG. 4. As seen in FIG. 4, conditioned media from cells transfected with the hTGFβR-IgG1-1 and hTGFβR-IgG1-2 fusion genes effectively blocked TGFβ signaling.

Together, these results demonstrate that TGFβ activity was markedly reduced by disclosed hTGFβR-IgG1 fusion proteins, e.g., hTGFβR-IgG1-1 and hTGFβR-IgG1-2, compared to a conventional hTGFβR-IgG1 fusion protein, e.g., hTGFβR-Fc.

Example 3: Inhibition of Tumor Growth

Experiments in mice were conducted using Ad-mTGFβR-IgG1, a virus carrying the mTGFβR-IgG1 fusion gene, in order to prevent the undesired induction of murine antibodies against the human TGFβR isoform. Ad-Control, a control virus in which the E1B-19k site used to carry the transgene was deleted, was also tested. The Ad-mTGFβR-IgG1 and Ad-Control viruses do not carry the 50 bp TAV-255 deletion, which serves as an attenuation mechanism to reduce viral replication in normal cells. Viruses were prepared as described in Example 1, and the key features of the viruses are shown schematically in TABLE 4 above.

Many mouse cells can be infected by human adenovirus with some degree of viral gene expression, but most mouse cell lines are not permissive for human adenovirus type 5 replication. ADS-12 is a mouse lung cancer cell line that was recently described as the first (and currently only) identified mouse cancer cell line that supports replication of human adenovirus at levels comparable to human cells, and was therefore chosen as a model system (Zhang et al. (2015) CANCER GENE THER. 22(1):17-22).

Mice carrying subcutaneous ADS-12 tumors were treated with intratumoral injections given every four days for three total doses of vehicle, Ad-Control, or Ad-mTGFβR-IgG1 at $10^9$ PFU/dose.

Figure 5A:
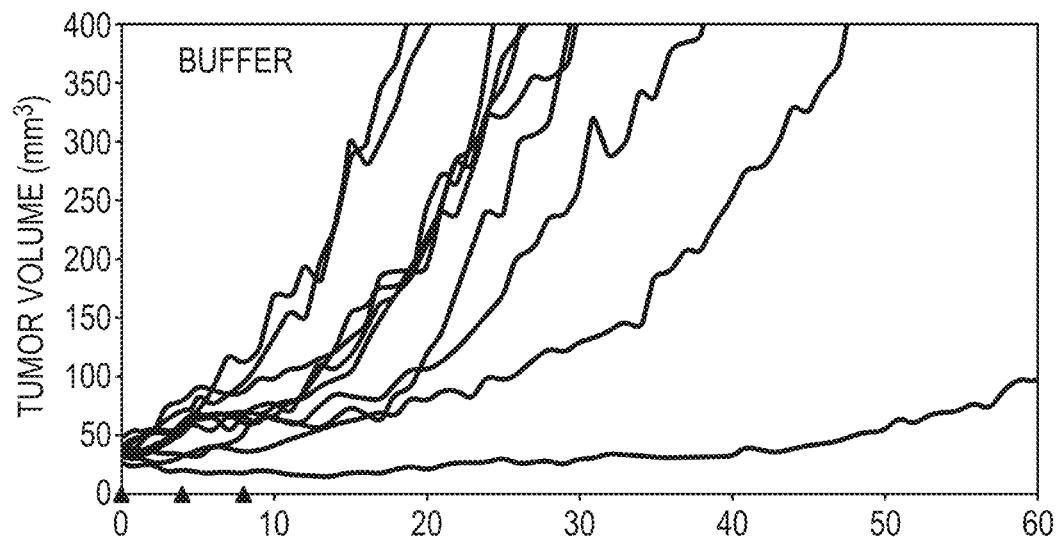
FIGS. 5A-5C depict tumor volumes in mice following treatment with the indicated virus. Each line represents the tumor volume of one mouse.
Figure 5B:
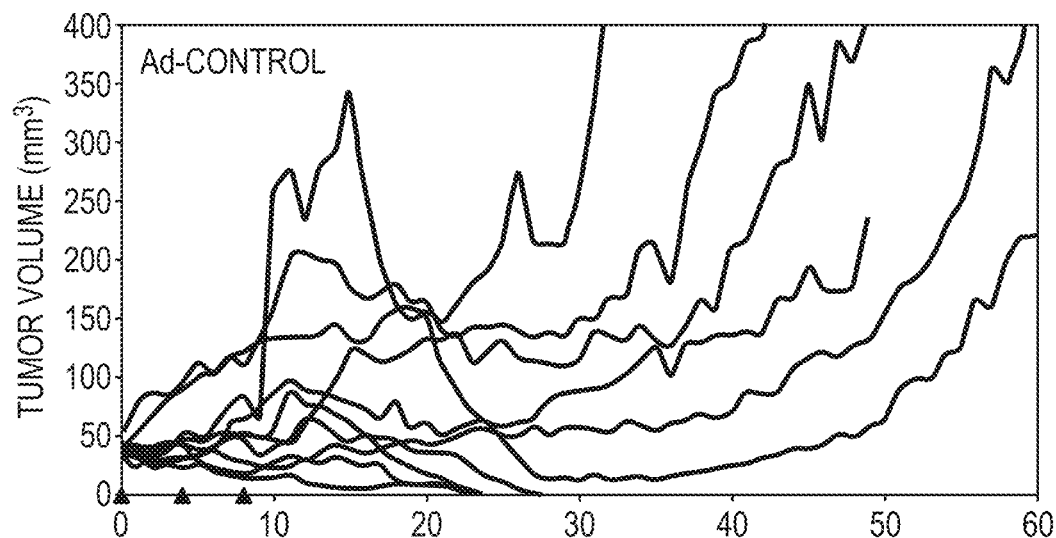
Figure 5C:
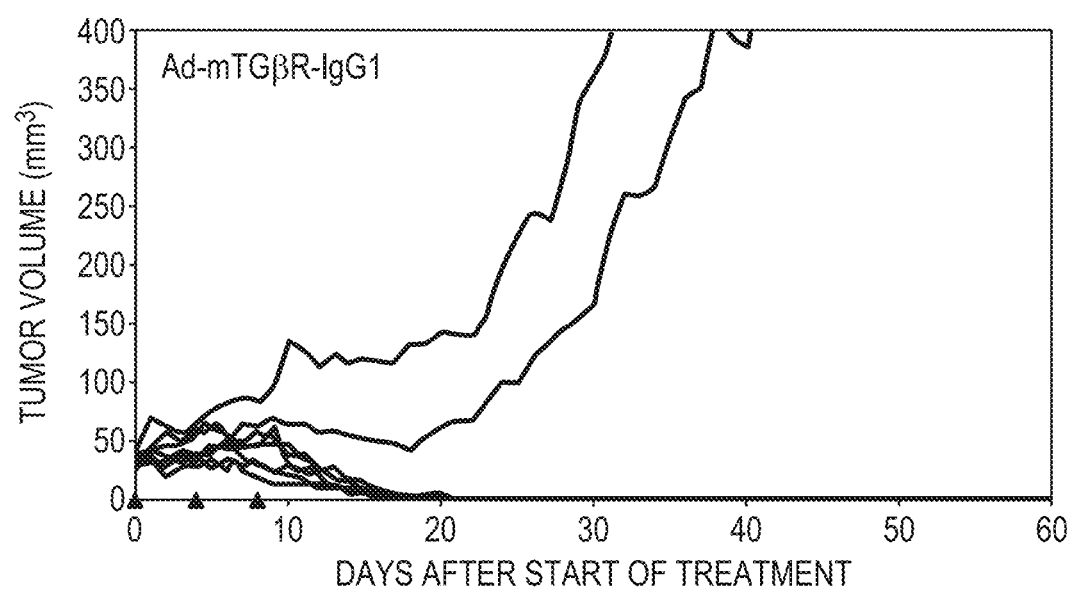

As shown in FIGS. 5A-5C, all tumors treated with intratumoral injections of buffer alone progressed. Four out of ten tumors treated with the "unarmed" Ad-Control virus completely regressed, indicative of oncolytic activity in the absence of tumor-specific TGFβ trap transgene expression. By contrast, eight out of ten tumors treated with Ad-mTGFβR-IgG1 completely regressed, demonstrating improved tumor kill with the transgene.

In summary, an oncolytic virus expressing a novel TGFβ trap disclosed herein showed significantly enhanced antitumor effects.

Example 4: Inhibition of TGFβ Signaling in Cancer Cell Lines

Figure 6A:
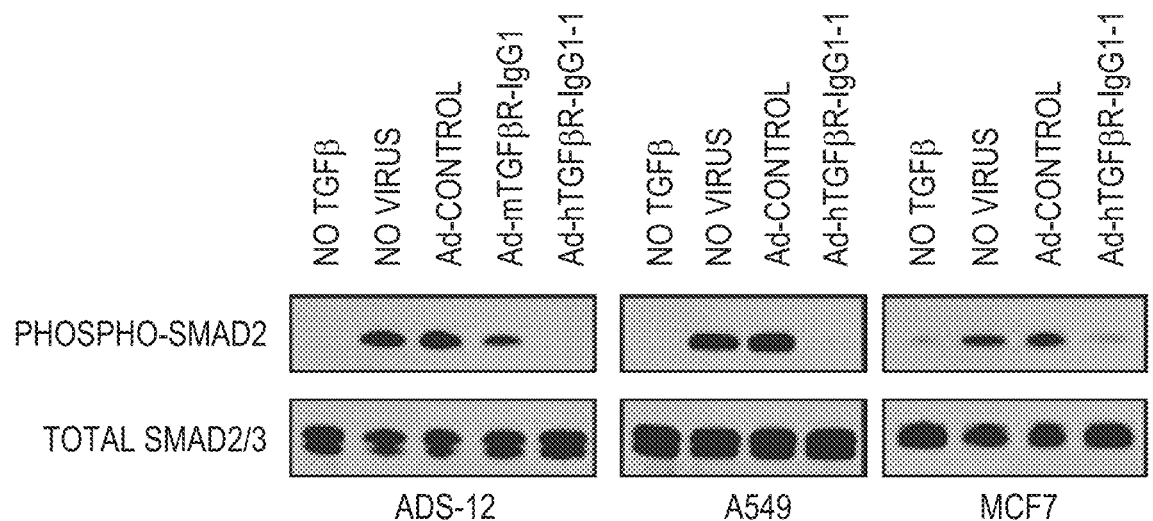
FIGS. 6A-6B depict Western blots for phosphorylated Smad2 following treatment of the indicated cell lines with TGFβ and/or the indicated virus. Total Smad2 and Smad3 were used as a loading control.
Figure 6B:
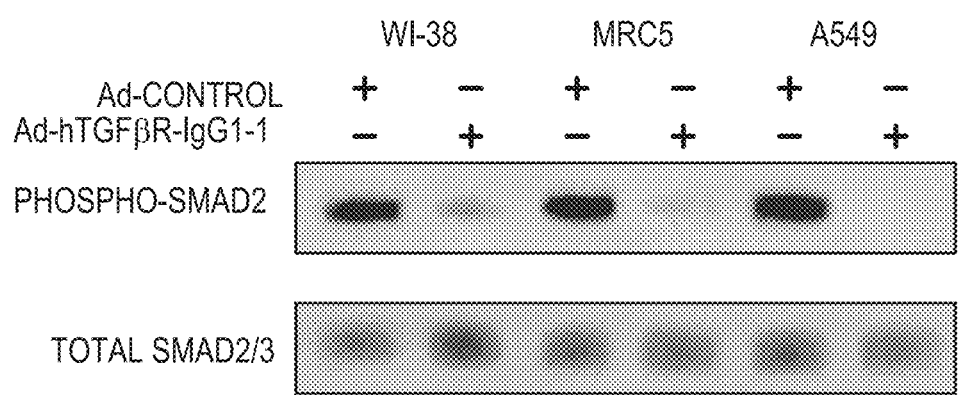

Assays on TGFβ inhibition were carried out in human cell lines using the Ad-hTGFβR-IgG1-1, Ad-mTGFβR-IgG1, and Ad-Control viruses. The viruses were prepared as described in Example 1 and the key features of the viruses are shown schematically in TABLE 4 above. Effects of virus were tested in normal (WI-38 and MRC5) and cancerous (ADS-12, A549, and MCF7) cells. Conditioned media from cells infected with the indicated virus was overlaid on fresh reporter cells and TGFβ added as described in Example 2. As seen in FIGS. 6A-6B, TGFβ induction of Smad2 phosphorylation was diminished in conditioned media from all cell lines infected with Ad-hTGFβR-IgG1-1. In summary, Ad-hTGFβR-IgG1-1 induced robust blockade of TGFβ in cancerous cells and even blunted TGFβ activity in infected normal cells.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. An isolated nucleic acid comprising a nucleotide sequence encoding a fusion protein, wherein the fusion protein comprises an amino acid sequence selected from SEQ ID NO: 22, SEQ ID NO: 62, and SEQ ID NO: 63.

2. An expression vector comprising the nucleic acid of claim 1.

3. The expression vector of claim 2, wherein the expression vector is an oncolytic virus.

4. A host cell comprising the expression vector of claim 2.

5. A pharmaceutical composition comprising: (i) the expression vector of claim 2; and (ii) at least one pharmaceutically acceptable carrier or diluent.

6. The isolated nucleic acid of claim 1, wherein the fusion protein comprises the amino acid sequence of SEQ ID NO: 22.

7. The isolated nucleic acid of claim 1, wherein the fusion protein comprises the amino acid sequence of SEQ ID NO: 62.

8. The isolated nucleic acid of claim 1, wherein the fusion protein comprises the amino acid sequence of SEQ ID NO: 63.

* * * * *